United States Patent
Pavlin

(10) Patent No.: US 7,329,719 B2
(45) Date of Patent: Feb. 12, 2008

(54) ESTER-TERMINATED POLY(ESTER-AMIDE) IN PERSONAL CARE PRODUCTS

(75) Inventor: Mark S Pavlin, Savannah, GA (US)

(73) Assignee: Arizona Chemical Company, Jacksonville, FL (US)

( * ) Notice: Subject to any disclaimer, the term of this patent is extended or adjusted under 35 U.S.C. 154(b) by 75 days.

(21) Appl. No.: 11/433,271

(22) Filed: May 12, 2006

(65) Prior Publication Data

US 2006/0204461 A1    Sep. 14, 2006

Related U.S. Application Data

(63) Continuation of application No. 11/005,320, filed on Dec. 6, 2004, now Pat. No. 7,253,249, which is a continuation of application No. 10/421,624, filed on Apr. 22, 2003, now Pat. No. 6,875,245.

(51) Int. Cl.
*C08G 63/02* (2006.01)

(52) U.S. Cl. .......... 528/272; 44/275; 424/401; 424/457; D28/85; 528/289; 528/295.5; 528/300; 528/308; 528/335; 528/339.5; 528/347

(58) Field of Classification Search .......... 44/275; 424/401, 457; D28/85; 528/300, 308, 339.5, 528/347
See application file for complete search history.

(56) References Cited

U.S. PATENT DOCUMENTS

| | | |
|---|---|---|
| 3,141,787 A | 7/1964 | Goetze et al. |
| 3,148,125 A | 9/1964 | Strianse et al. |
| 3,157,681 A | 11/1964 | Fischer |
| 3,255,082 A | 6/1966 | Barton |
| 3,615,289 A | 10/1971 | Felton |
| 3,645,705 A | 2/1972 | Miller et al. |
| 4,049,792 A | 9/1977 | Elsnau |
| 4,137,306 A | 1/1979 | Rubino et al. |
| 4,275,054 A | 6/1981 | Sebag et al. |
| 4,279,658 A | 7/1981 | Harvey et al. |
| 4,659,562 A | 4/1987 | Arraudeau et al. |
| 4,937,069 A | 6/1990 | Shin |
| 5,069,897 A | 12/1991 | Orr |
| 5,102,656 A | 4/1992 | Kasat |
| 5,266,321 A | 11/1993 | Shukuzaki et al. |
| 5,498,407 A | 3/1996 | Atlas |
| 5,500,209 A | 3/1996 | Mendolia et al. |
| 5,538,718 A | 7/1996 | Aul et al. |
| 5,851,517 A | 12/1998 | Mougin et al. |
| 5,911,974 A | 6/1999 | Brieva et al. |
| 5,945,095 A | 8/1999 | Mougin et al. |
| 5,959,009 A | 9/1999 | Konik et al. |
| 5,965,112 A | 10/1999 | Brieva et al. |
| 6,074,654 A | 6/2000 | Drechsler et al. |
| 6,111,055 A | 8/2000 | Berger et al. |
| 6,129,771 A | 10/2000 | Ficke et al. |
| 6,214,063 B1 | 4/2001 | DeStefano et al. |
| 6,254,877 B1 | 7/2001 | De La Poterie et al. |
| 6,402,408 B1 | 6/2002 | Ferrari |
| 6,682,748 B1 | 1/2004 | De La Poterie et al. |
| 6,960,339 B1 | 11/2005 | Ferrari |

FOREIGN PATENT DOCUMENTS

| | | |
|---|---|---|
| EP | 0106762 A1 | 4/1984 |
| EP | 0106762 B1 | 4/1984 |
| EP | 0295886 | 1/1992 |
| EP | 0291334 | 9/1993 |
| EP | 0749746 | 12/1996 |
| EP | 0749747 | 12/1998 |
| EP | 0923928 A1 | 6/1999 |
| EP | 0923928 B1 | 6/1999 |
| EP | 1068855 | 1/2001 |
| EP | 1068856 | 1/2001 |
| EP | 0930060 | 6/2001 |
| EP | 0921217 | 12/2003 |
| FR | 1529329 | 6/1967 |
| JP | 57/158714 | 9/1982 |
| JP | 3153613 | 1/1993 |
| JP | 7/196440 | 2/1997 |
| WO | WO 98/42298 | 10/1998 |
| WO | WO 00/78878 | 12/2000 |
| WO | WO 02/055030 | 7/2002 |

*Primary Examiner*—Terressa Boykin
(74) *Attorney, Agent, or Firm*—Joseph W. Segers, III; J. Mark Gilbreth; Deborah Segers

(57) ABSTRACT

A resin composition is prepared by reacting components comprising dibasic acid, diamine, polyol and monoalcohol, wherein (a) at least 50 equivalent percent of the dibasic acid comprises polymerized fatty acid; (b) at least 50 equivalent percent of the diamine comprises ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol. This resin composition may be formulated into, for example, personal care products, fragrance releasing products and candles.

25 Claims, No Drawings

ESTER-TERMINATED POLY(ESTER-AMIDE) IN PERSONAL CARE PRODUCTS

This application is a Continuation Application of U.S. patent application Ser. No. 11/005,320 now U.S. Pat. No. 7,253,249, "ESTER-TERMINATED POLY(ESTER AMIDES) IN PERSONAL CARE PRODUCTS", which was filed on Dec. 6, 2004, which is a Continuation Application of U.S. patent application Ser. No. 10/421,624, entitled "ESTER-TERMINATED POLY(ESTER AMIDES) IN PERSONAL CARE PRODUCTS", which was filed on Apr. 22, 2003, now U.S. Pat. No. 6,875,245, issued Apr. 5, 2005, all of which are hereby incorporated, in their entirety, herein by reference.

TECHNICAL FIELD

The invention relates to gelling agents, and in particular to gellants for low polarity liquids such as hydrocarbons, and the use thereof in commercial products, e.g., personal care products.

BACKGROUND OF THE INVENTION

Personal care products generally contain one or more active ingredients within a carrier formulation. While the active ingredient(s) determine the ultimate performance properties of the product, the carrier formulation is equally critical to the commercial success of the product. The rheology of the carrier (also referred to as the "base") largely determines the flow properties of the product, and the flow properties largely determine the manner in which the consumer will apply or use the product.

For example, aluminum chlorohydrate and aluminum-zirconium tetrachlorohydrex-Gly are metal salts that are commonly used as active ingredients in deodorant and antiperspirant products. Consumers have shown a preference for applying deodorant from a stick form. Thus, the carrier in a stick-form deodorant must be a relatively hard substance, and waxy fatty alcohol such as stearyl alcohol has been used as the carrier in these products. As another example, the active ingredient in a lipstick is the colorant. A lipstick should not be as hard as a stick deodorant, but of course must maintain its shape when undisturbed at room temperature. A blend of wax and oil is known to provide a consistency that is well-suited as a carrier for a lipstick. As a final example, shampoo desirably has a viscosity greater than water, and when the active ingredient(s) in a shampoo does not have a sufficiently high viscosity, a somewhat viscous carrier material is desirably included in the shampoo formulation.

From the above examples, it is seen that formulators of personal care products depend upon the availability of materials having various rheological properties, in order to formulate a successful personal care product. Materials which have a gel-like character, in that they maintain their shape when undisturbed but flow upon being rubbed, are often desired for personal care products.

Transparent (i.e., clear) carriers are needed by formulators who develop a personal care product wherein colorant is an active ingredient, because a transparent carrier (as opposed to an opaque carrier) will minimally, if at all, interfere with the appearance of the colorant. However, in recent years consumers have demonstrated an increasing preference for transparent personal care products such as deodorants and shampoos. There is thus an increasing demand for transparent materials which can provide the rheological properties needed for various personal care products, and particularly which can impart gel-like character to a formulation.

Polyamide resin prepared from polymerized fatty acid and diamine is reported to function as a gellant in formulations developed for personal care products. For example, U.S. Pat. No. 3,148,125 is directed to a clear lipstick composition formed from polyamide resin compounded with a lower aliphatic alcohol and a so-called "polyamide solvent." Likewise, U.S. Pat. No. 5,500,209 is directed to forming a gel or stick deodorant, where the composition contains polyamide gelling agent and a solvent system including monohydric or polyhydric alcohols. Thus, the prior art recognizes to blend certain polyamides with alcohols, to thereby form a gel.

Certain modified polyamide resins, e.g., polyamides which are only partly amidated but contain esterified carboxyl groups, have been reported to impart high gel strength and pronounced thixotropic properties to coating compositions that contain alkyd resins or drying oils. See U.S. Pat. No. 3,141,767 to Goetze et al. However, the modified polyamide resins of Goetze et al. are not disclosed as being useful gellants in personal care products, nor useful gellants when a low polarity fluid is used as the vehicle.

Low polarity fluids are desirably included in a personal care formulation because they are often transparent, relatively inexpensive, and non-toxic. Low polarity fluids are also available in a wide variety of viscosities and grades. However, low polarity fluids often do not have the rheological properties that are desired in a carrier, e.g., they do not naturally exhibit gel-like character. There is a need in the art for materials that can be combined with low polarity solvent, such as a hydrocarbon or fatty acid ester, to afford a transparent material which has gel-like character. The gel-like character is preferably of a smooth, silky feeling when the gel is rubbed against the skin.

The present invention provides this and related advantages as described herein.

SUMMARY OF THE INVENTION

In one aspect, the present invention provides a resin composition prepared by reacting components comprising dibasic acid, diamine, polyol and monoalcohol, wherein (a) at least 50 equivalent percent of the dibasic acid comprises polymerized fatty acid; and (b) at least 50 equivalent percent of the diamine comprises ethylene diamine. Preferably, (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol.

In another aspect, the present invention provides a composition comprising (a) a resin composition prepared by reacting together components comprising dibasic acid, diamine, polyol and monoalcohol, wherein at least 50 equivalent percent of the dibasic acid comprises polymerized fatty acid; and at least 50 equivalent percent of the diamine comprises ethylene diamine; and (b) hydrocarbon; the composition having a consistency of a gel. Preferably, 10-60 equivalent percent of the total of the hydroxyl and amine equivalents provided by diamine, polyol and monoalcohol are provided by monoalcohol; and no more than 50 equivalent percent of the total of the hydroxyl and amine equivalents provided by diamine, polyol and monoalcohol are provided by polyol. In one aspect of the invention, some or all of the hydrocarbon is substituted with polydimethylsiloxanes (PDMS) or other silicon-containing material (such as phenylated silicones such as phenyl trimethicones, phenyl dimethicones and phenyl trimethylsiloxy diphenylsiloxanes etc.).

In another aspect, the present invention provides a composition comprising (a) a resin composition prepared by reacting together components comprising dibasic acid, diamine, polyol and monoalcohol, wherein at least 50 equivalent percent of the dibasic acid comprises polymerized fatty acid; and at least 50 equivalent percent of the diamine is ethylene diamine; and (b) an ester compound comprising the chemical group —O—C(=O)—, the composition having the consistency of a gel. Preferably, 10-60 equivalent percent of the total of the hydroxyl and amine equivalents provided by diamine, polyol and monoalcohol are provided by monoalcohol; and no more than 50 equivalent percent of the total of the hydroxyl and amine equivalents provided by diamine, polyol and monoalcohol are provided by polyol.

In another aspect, the present invention provides a composition comprising (a) a resin composition prepared by reacting together components comprising dibasic acid, diamine, polyol and monoalcohol, wherein at least 50 equivalent percent of the dibasic acid comprises polymerized fatty acid; and at least 50 equivalent percent of the diamine is ethylene diamine; and (b) a polyester compound; the composition having a consistency of a gel. Preferably, 10-60 equivalent percent of the total of the hydroxyl and amine equivalents provided by diamine, polyol and monoalcohol are provided by monoalcohol; and no more than 50 equivalent percent of the total of the hydroxyl and amine equivalents provided by diamine, polyol and monoalcohol are provided by polyol.

In another aspect, the present invention provides a method for preparing a resin composition comprising ester-terminated poly(ester-amide), the method comprising reacting w equivalents of hydroxyl from polyol or a reactive equivalent thereof, x equivalents of carboxylic acid from diacid or a reactive equivalent thereof, y equivalents of amine from diamine, and z equivalents of hydroxyl from monoalcohol or a reactive equivalent thereof under reactions conditions to provide a resin composition having an acid number of less than 20 and an amine number of less than 20, wherein at least about 50% of the carboxylic acid equivalents are from polymerized fatty acid, at least about 50% of the amine equivalents are from ethylene diamine, and monoalcohol is substantially the only monofunctional reactant used to form the resin. Preferably, 10-60 equivalent percent of the total of the hydroxyl and amine equivalents provided by diamine, polyol and monoalcohol are provided by monoalcohol; and no more than 50 equivalent percent of the total of the hydroxyl and amine equivalents provided by diamine, polyol and monoalcohol are provided by polyol.

The present invention also provides a personal care product comprising a resin composition prepared by reacting components comprising dibasic acid, diamine, polyol and monoalcohol, wherein (a) at least 50 equivalent percent of the dibasic acid comprises polymerized fatty acid; (b) at least 50 equivalent percent of the diamine comprises ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol.

In another aspect, the present invention provides a controlled release composition comprising a volatile component and a resin composition prepared by reacting components comprising dibasic acid, diamine, polyol and monoalcohol, wherein (a) at least 50 equivalent percent of the dibasic acid comprises polymerized fatty acid; (b) at least 50 equivalent percent of the diamine comprises ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol.

In another aspect, the present invention provides a candle comprising a wick and a resin composition prepared by reacting components comprising dibasic acid, diamine, polyol and monoalcohol, wherein (a) at least 50 equivalent percent of the dibasic acid comprises polymerized fatty acid; (b) at least 50 equivalent percent of the diamine comprises ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol; where the candle further comprises a solvent that is gelled by the resin.

These and other aspects of the present invention are described in further detail below.

DETAILED DESCRIPTION OF THE INVENTION

The present invention is directed to ester-terminated poly(ester-amides) (ETPEA) and a method of preparing a resinous composition (hereinafter, simply "a resin") comprising, in whole or part, EPTEA. A resin comprising ETPEA (an "ETPEA resin") is useful as a gelling agent for hydrocarbons and other low polarity liquids, where the resultant gels are useful components in, for example, personal care products, candles, lubricants, inks, corrosion inhibitors, cosmetic formulations and other products that can benefit from gel-like character.

In one aspect, the present invention provides a resin composition prepared by reacting components comprising dibasic acid, diamine, polyol and monoalcohol, wherein at least 50 equivalent percent of the dibasic acid comprises polymerized fatty acid; and at least 50 equivalent percent of the diamine comprises ethylene diamine. Before further describing this resin, and other aspects of the present invention, the reactants useful in preparing the resin will be described.

The dibasic acid is an organic molecule containing two carboxylic acid groups or reactive equivalents thereof. A preferred dibasic acid is polymerized fatty acid, and in particular the dimer acid component of polymerized fatty acid. Polymerized fatty acid is typically a mixture of structures, including dimer acid and trimer acid, where individual dimer acids may be saturated, unsaturated, cyclic, acyclic, etc. Polymerized fatty acid as used to form the resin of the invention is a well known material of commerce, and thus need not be described in great detail. Polymerized fatty acid is typically formed by heating long-chain unsaturated fatty acids, e.g., $C_{18}$ monocarboxylic acids, to about 200-250° C. in the presence of a clay catalyst in order that the fatty acids polymerize. The product typically comprises dimer acid, i.e., $C_{36}$ dicarboxylic acid formed by dimerization of the fatty acid, and trimer acid, i.e., $C_{54}$ tricarboxylic acid formed by trimerization of the fatty acid. A more detailed discussion of fatty acid polymerization may be found in, e.g., U.S. Pat.

No. 3,157,681 and *Naval Stores—Production, Chemistry and Utilization*, D. F. Zinkel and J. Russell (eds.), Pulp. Chem. Assoc. Inc., 1989, Chapter 23.

Because fatty acid polymerization typically forms much more dimer acid than trimer acid, those skilled in the art may often refer to polymerized fatty acid as dimer acid, even though some trimer acid, and even higher polymerization products, may be present with the dimer acid. It is preferred that the polymerized fatty acid contain less than about 20 weight percent of trimer acid, based on the total weight of the polymerized fatty acid, and that the dimer acid constitute at least about 80 weight percent of the polymerized fatty acid. More preferably, the dimer acid constitutes essentially all of the polymerized fatty acid.

Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is preferred for preparing polymerized fatty acid useful in the invention. While tall oil fatty acid is a preferred source of long-chain fatty acid, the polymerized fatty acid may alternatively be prepared by polymerization of unsaturated fatty acids from other sources, e.g., soybeans or canola. The polymerized fatty acid useful in the invention is a liquid, with an acid number on the order of about 180 to about 200.

The polymerized fatty acid of the invention may be hydrogenated prior to being used in the resin-forming reaction of the invention. Hydrogenation tends to provide for a slightly higher melting point for the inventive resin, as well as provide the resin with greater oxidative and color stability. Hydrogenated polymerized fatty acid tends to provide for a lighter colored resin, and is a preferred polymerized fatty acid for use in the practice of the present invention.

Polymerized fatty acid, dimer acid, and hydrogenated versions thereof may be obtained from a number of commercial suppliers. For example, Arizona Chemical (Jacksonville, Fla.) sells polymerized fatty acid under their UNIDYME® trademark.

In addition to polymerized fatty acid, or reactive equivalents thereof, the dibasic acid may comprise dibasic acid of the formula HOOC—$R^1$—COOH or reactive equivalents thereof, which may be referred to herein as co-diacid. In one aspect, $R^1$ contains 4 to 19, preferably about 4 to 12, and more preferably about 4 to 8 carbon atoms. The carbon atoms may be arranged in a linear, branched or cyclic fashion, and unsaturation may be present between any two carbon atoms. Thus, $R^1$ may be aliphatic or aromatic. When present, these lower carbon-number $R^1$ groups are preferably formed entirely of carbon and hydrogen, i.e., are hydrocarbon groups.

An exemplary co-diacid is a so-called "linear" diacid of the formula HOOC—$R^1$—COOH wherein $R^1$ is a linear $C_{4-12}$ hydrocarbon group, and more preferably is a linear $C_{6-8}$ hydrocarbon group. Linear co-diacids suitable for the present invention include 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedoic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid for use in the present invention is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_{21}$ diacid is commercially available from Westvaco Corporation, Chemical Division, Charleston Heights, S.C., as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR)) and at least one aromatic ring ("Ar"). Phthalic acids, e.g., isophthalic acid and terephthalic acid, are exemplary aromatic diacids. The aromatic diacid may contain aliphatic carbons bonded to the aromatic ring(s), as in HOOC—$CH_2$—Ar—$CH_2$—COOH and the like. The aromatic diacid may contain two aromatic rings, which may be joined together through one or more carbon bonds, (e.g., biphenyl with carboxylic acid substitution) or which may be fused (e.g., naphthalene with carboxylic acid substitution).

In one aspect, the resin is prepared with co-diacid and the co-diacid is selected from 1,4-cyclohexane dicarboxylic acid, isophthalic acid, adipic acid, azeleic acid, sebacic acid, and dodecandioic acid.

The diamine reactant has two amine groups, both of which are preferably primary amines, and is represented by the formula HN($R^{2a}$)—$R^2$—N($R^{2a}$)H. $R^{2a}$ is preferably hydrogen, but may also be an alkyl group or may also join together with $R^2$ or another $R^{2a}$ to form a heterocyclic structure. A preferred diamine is ethylene diamine, i.e., a diamine wherein $R^{2a}$ is hydrogen and $R^2$ is —$CH_2CH_2$—.

Diamines other than ethylene diamine may be referred to herein as co-diamines. When present, co-diamines are preferably used in a minor amount compared to the ethylene diamine. In a co-diamine, $R^2$ may be a hydrocarbon group having at least three carbon atoms, where the carbon atoms may be arranged in a linear, branched or cyclic fashion, and the group may be saturated or contain unsaturation. Thus, $R^2$ may be aliphatic or aromatic. Preferred $R^2$ hydrocarbon groups in the co-diamine have 2 to 36 carbon atoms, more preferred $R^2$ hydrocarbon groups have 2 to 12 carbon atoms, and still more preferred hydrocarbon groups have 2 to 6 carbon atoms.

Exemplary co-diamines having hydrocarbon $R^2$ groups include, without limitation, 1,2-diaminopropane, 1,3-diaminopropane, 1,4-diaminobutane, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,2; 1,3 and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminonaphthalene (all isomers, including 1,5; 1,8; and 2,3) and 4-amino-2,2,6,6-tetramethylpiperidine.

Suitable aromatic co-diamines (by which is meant molecules having two reactive, preferably primary amine groups (—$NH_2$) and at least one aromatic ring ("Ar") include xylene diamine and naphthalene diamine (all isomers).

The $R^2$ group of the co-diamine may contain oxygen atoms in the form of a polyalkylene oxide group. Exemplary polyalkylene oxide-based co-diamines include, without limitation, the JEFFAMINE™ diamines, i.e., poly(alkyleneoxy)diamines from Huntsman Chemical (Salt Lake City, Utah), also known as polyether diamines. Preferred polyalkylene oxide-containing co-diamines are the JEFFAMINE® ED, XTJ and D series diamines. Ether-containing $R^2$ groups are not preferred, as they tend to lower the melting point of the resin to an undesirable extent. However, small amounts of a polyalkylene oxide-based co-diamine with a major amount of ethylene diamine are suitable for use in the invention The $R^2$ group of the co-diamine may contain nitrogen atoms, where these nitrogen atoms are preferably secondary or tertiary nitrogen atoms. A typical nitrogen atom-containing $R^2$ group having secondary nitrogen atoms is a polyalkylene amine, i.e., a group containing alternating alkylene groups and amine groups (i.e., —NH— groups). The alkylene group is preferably ethylene, i.e., —$CH_2CH_2$—, and the polyalkylene amine may be represented by the formula $NH_2$—$(CH_2CH_2NH)_m CH_2CH_2$—$NH_2$ wherein m is an integer from 1 to about 5. Diethylenetriamine (DETA) and triethylenetetraamine (TETA) are representative examples. When the diamine contains two primary amines in addition to secondary amines, the EPTEA-forming reaction is preferably conducted at relatively low temperature, so that the primary amines (in preference to the secondary amines) react with the diacid component.

However, the nitrogen atoms in the nitrogen-containing $R^2$ group may also be present as tertiary nitrogen atoms, e.g., they may be present in a heterocycle of the formula:

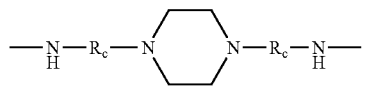

wherein $R_c$ is a $C_{1-3}$ alkyl group. Bis(aminoethyl)-N,N'-piperazine and bis(aminopropyl)-N,N'-piperazine may be used to introduce these $R^2$ groups into an ETPEA molecule, and these are such co-diamines according to the invention. In addition, the co-diamine may have one primary amine group and one secondary amine group (e.g., N-ethylethylenediamine or 1-(2-aminoethyl)piperazine). Generally, it is preferred that amine compounds having secondary amines not be present in the reaction mixture to any great extent, because their incorporation into an ester terminated polyamide tends to provide for poorer gelling ability of the ester-terminated polyamide.

In general, the diamine reactant may have the formula $HN(R^{2a})$—$R^2$—$NH(R^{2a})$ wherein $R^{2a}$ is preferably hydrogen, but may also be $C_{1-10}$alkyl, preferably $C_{1-5}$alkyl, and more preferably $C_{1-3}$alkyl. In addition, $R^{2a}$ may join together with $R^2$ or another $R^{2a}$ group to form a heterocyclic structure. For example, when piperazine is used as a co-diamine, the two $R^{2a}$ groups in the $HN(R^{2a})$—$R^2$—$NH(R^{2a})$ structure have joined together to form an ethylene bridge.

In one aspect, the ETPEA resin of the invention is prepared from co-diamine, where the co-diamine is selected from 1,6-hexanediamine, xylenediamine, 1,2-propanediamine, 2-methylpentamethylenediamine, and 1,12-dodecanediamine. Suitable diamines of the present invention are available from a number of commercial sources including Aldrich (Milwaukee, Wis.; http://www.aldrich.sial.com); EM Industries, Inc. (Hawthorne, N.Y.; http://www.em-science.com); Lancaster Synthesis, Inc. (Windham, N.H.; http://www.lancaster.co.uk); Spectrum Quality Product, Inc. (New Brunswick, N.J.; http://www.spectrumchemical.com).

The monoalcohol may be represented by the formula $R^3$—OH, wherein $R^3$ is preferably a hydrocarbon group having at least ten carbon atoms. Thus, the monoalcohol can also be described as a monohydric alcohol. In one aspect, $R^3$ is a $C_{10-30}$ hydrocarbon, preferably a $C_{12-24}$ hydrocarbon, still more preferably is a $C_{16-22}$ hydrocarbon, and yet still more preferably is a $C_{18}$ hydrocarbon. As used herein, the term $C_{10-30}$ hydrocarbon refers to a hydrocarbon group having at least 10, but not more than 30 carbon atoms, and similar terms have an analogous meaning. The carbon atoms of the hydrocarbon group may be arranged in a linear, branched or cyclic fashion, and the group may be saturated or unsaturated. However, in one aspect of the present invention, $R^3$ is linear, with the hydroxyl group located on a terminal carbon atom, i.e., the monoalcohol is a primary monoalcohol. Thus, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol) are preferred monoalcohols for preparing resins of the invention, where names in parentheses are common or trivial names by which these monoalcohols are known. While the monoalcohol has been exemplified with saturated alkyl groups, the monoalcohol may alternatively contain an alkenyl group, i.e., an alkyl group having unsaturation between at least any two adjacent carbon atoms. One or a mixture of these alcohols may be used to prepare a resin of the invention.

Another monoalcohol reactant suited for the invention is a so-called Guerbet alcohol. Guerbet alcohols have the general formula H—C(Ra)(Rb)-$CH_2$—OH wherein Ra and Rb may be the same or different and preferably represent a $C_{6-12}$ hydrocarbon group. Further discussion of Guerbet alcohols may be found in, e.g., "Dictionary For Auxiliaries For Pharmacy, Cosmetics And Related Fields," H. P. Fiedler, $3^{rd}$ Ed., 1989, Cantor Aulendorf. 2-Hexadecyloctadecanol, which has 24 carbon atoms, is a preferred Guerbet alcohol for use in the present invention.

Another suitable monoalcohol reactant is a linear wax alcohol. Suitable linear wax alcohols are commercially available from, e.g., Petrolite Corporation (Tulsa, Okla.) under their UNILIN® trademark. These wax alcohols are typically a blend of linear alcohols having at least about 20 carbon atoms, and more typically at least about 24 carbon atoms. Vapor pressure osmometry (VPO), among many other techniques, may be used to characterize the number average molecular weight of a blend of alcohols. In one aspect, the mixture of monohydric linear wax alcohols has a number average molecular weights by VPO of about 200 to about 800, preferably about 300 to about 600. Pure $C_{22}$ monohydric linear alcohol has a molecular weight of 326 by VPO.

The monohydric alcohol, whether present as an essentially pure alcohol or in a mixture of monohydric alcohols, preferably has a straight chain alkyl group. Exemplary alcohols useful in the invention include 1-eicosanol ($C_{20}$), 1-docosanol ($C_{22}$, also known as behenyl alcohol), dotriacontanol ($C_{32}$), tetratriacontanol ($C_{34}$), pentatriacontanol ($C_{35}$), tetracontanol ($C_{40}$), tetraacontanol ($C_{44}$), dopentaacontanol ($C_{54}$), tetrahexaacontanol ($C_{64}$), dohexaacontanol ($C_{72}$), etc.

A final ingredient necessary in preparing an ETPEA resin of the present invention is polyol, which may also be referred to as polyhydric alcohol. The polyol is of the formula $R^4(OH)_n$ wherein $R^4$ is an n-valent organic group. For instance, $R^4$ may be a $C_2$-$C_{20}$ organic group without hydroxyl substitution. As another example, $R^4$ may be a hydrocarbon. Typically, n is selected from 2, 3, 4, 5 and 6. Suitable polyols for use in preparing an ETPEA resin of the present invention include ethylene glycol, propylene glycol, butylene glycol, glycerol, trimethylolpropane, pentaerythritol, neopentyl glycol, tris(hydroxylmethyl)methanol, di-pentaerythritol, and tri-pentaerthyritol.

Reactive equivalents of diacids and/or diamines may be used in the invention. For example, diesters may be substituted for some or all of the diacid, where "diesters" refer to the esterification product of diacid with hydroxyl-containing molecules. However, such diesters are preferably prepared from relatively volatile hydroxyl-containing molecules, in order that the hydroxyl-containing molecule may be easily removed from the reaction vessel subsequent to monoalcohol and/or diamine (both as defined herein) reacting with the diester. A lower alkyl diester, e.g., the esterification or diesterification product of diacid as defined herein and a $C_{1-4}$ monohydic alcohol (e.g., methanol, ethanol, propanol and butanol), may be used in place of some or all of the diacid in the ETPEA-resin forming reaction of the invention. The acid halide of the diacid may likewise be employed in place of some or all of the diacid, however such a material is typically much more expensive and difficult to handle compared to the diacid, and thus the diacid is preferred. Likewise, the monoalcohol may be esterified with a volatile acid, e.g., acetic acid, prior to being employed in the ETPEA resin-forming reaction of the invention. While such reactive equivalents may be employed in the reaction, their presence is not preferred because such equivalents introduce undesired reactive groups into the reaction vessel.

In preparing a resin of the invention, the above-described reactants may be combined in any order. Preferably, the reactants are simply mixed together and heated for a time and at a temperature sufficient to achieve essentially complete reaction, to thereby form the inventive resin. The terms "complete reaction" and "reaction equilibrium" as used herein have essentially the same meaning, namely that further heating of the product resin does not result in any appreciable change in the performance characteristics of the product resin, where the most relevant performance characteristic is the ability of the product resin to form a clear, firm gel upon being combined with a solvent (as mentioned above and discussed further below).

Thus, the ETPEA resin may be formed in a one-step procedure, wherein all of the dibasic acid, diamine, polyol and monoalcohol (including co-diacid and co-diamine, if present) are combined and then heated to about 200-250° C. for a few hours, typically 2-8 hours. As one or more of the reactants may be a solid at room temperature, it may be convenient to combine each of the ingredients at a slightly elevated temperature, and then form a homogeneous mixture prior to heating the reaction mixture to a temperature sufficient to cause reaction between the dibasic acid, diamine, polyol and monoalcohol. Alternatively, although less preferably, two or three of the reactants may be combined and reacted together, and then the remaining reactant(s) is/are added followed by further heating the desired product is obtained. Reaction progress may be conveniently monitored by periodically measuring the acid and/or amine number of the product mixture.

Any catalyst that may accelerate amide formation between carboxylic acid and amine groups, and/or ester formation between carboxylic acid and hydroxyl groups, may be present in the reaction mixture described above. Thus, mineral acid such as phosphoric acid, or tin salts such as dibutyltin oxide, may be present during the reaction. In addition, it is preferred to remove water from the reaction mixture as it is formed upon amide and ester formation. This is preferably accomplished by maintaining a vacuum on the reacting mixture.

It is important to control the stoichiometry of the reactants in order to prepare ester-terminated poly(ester-amides) according to the invention. In the following discussion regarding reactant stoichiometry, the terms "equivalent(s)" and "equivalent percent" will be used, and are intended to have their standard meanings as employed in the art. However, for additional clarity, it is noted that equivalents refer to the number of reactive groups present in a molar quantity of a molecule, such that a mole of a dibasic acid (e.g., sebacic acid) has two equivalents of carboxylic acid, while a mole of monoalcohol has one equivalent of hydroxyl. Furthermore, it is emphasized that the dibasic acid has only two reactive groups (both carboxylic acids), the monoalcohol has only one reactive group (a hydroxyl group), the diamine has only two reactive groups (preferably both primary amines), and the polyol has at least two reactive groups (i.e., at least two reactive hydroxyl groups) and these are preferably, although not necessarily, the only reactive materials present in the reaction mixture.

According to the invention, is it preferred that the equivalents of carboxylic acid are substantially equal to the combined equivalents of hydroxyl contributed by monoalcohol and polyol, and amine contributed by diamine. In other words, if the reaction mixture used to form an ETPEA resin has "x" equivalents of carboxylic acid, "y" equivalents of amine and "z" equivalents of hydroxyl (from the combination of monoalcohol and polyol), then $0.9 \leq \{x/(y+z)\} \leq 1.1$, and preferably $\{x/(y+z)\}$ is substantially 1.0. Under these conditions, substantially all of the carboxylic acid groups will react with substantially all of the hydroxyl and amine groups, so that the final product contains very little unreacted carboxylic acid, hydroxyl or amine groups. In other words, each of the acid and amine numbers of a resin of the invention is preferably less than about 25, is more preferably less than about 15, and is more preferably less than about 10, and is still more preferably less than about 5.

When co-diacid is employed to prepare an ETPEA resin, the co-diacid preferably contributes no more than about 50% of the equivalents of carboxylic acid present in the reaction mixture. Stated another way, the co-diacid contributes from 0-50 equivalent percent of the acid equivalents in the reaction mixture. Preferably, the co-diacid contributes 0-25 equivalent percent, and more preferably contributes 0-10 equivalent percent of the acid equivalents in the reaction mixture.

When co-diamine is employed to prepare an ETPEA resin, the co-diamine present in the reaction mixture preferably contributes no more than about 50% of the equivalents of amine present in the reaction mixture Stated another way, the co-diamine contributes from 0-50 equivalent percent of the amine equivalents in the reaction mixture. Preferably, the co-diamine contributes 0-25 equivalent percent, and more preferably contributes 0-10 equivalent percent of the amine equivalents in the reaction mixture.

The stoichiometry of the reactants will have a significant impact on the composition and properties of the ETPEA resin. For example, ETPEA resins made with increasing amounts of monoalcohol will tend to have lower average molecular weights. In other words, as more monofunctional reactant is used, the number of amide pairs in an average ETPEA molecule of the resin will tend to decrease. On the other hand, as less monoalcohol is used, the average molecular weight of the ETPEA in the resulting resin will increase. In general, increasing the average molecular weight for the ETPEAs in a resin will tend to increase the melting point and melt viscosity of the resin, which tends to provide a firmer gel when the ETPEA resin is combined with a low polarity liquid. However, when the average molecular weight of the ETPEA increases to a certain point, the EPTEA resins become insoluble in low polarity solvents, and therefore do not form desirable gels. Therefore, in a preferred aspect of the invention, the monoalcohol level in the reactants should be such that at least 10 equivalent percent of the total amine and hydroxyl equivalents should be derived from monoalcohol.

The amount of polyol used in the reactant formulation will also have an impact on the properties of the ETPEA resin. Increasing the level of polyol relative to the other reactants tends to decrease the softening point of the ETPEA resin. When the polyol contributes greater than about 50 equivalent percent of the total equivalents of hydroxyl and amine groups present in the ETPEA-forming reaction mixture, then the resulting ETPEA resin becomes undesirably "soft" and mixtures of this soft resin with a low polarity fluid tends to form more of a viscous oil than a gel. Accordingly, in one aspect of the invention, the hydroxyl equivalents from polyol are less than or equal to 50% of the total hydroxyl and amine equivalents contributed by the total of the polyol, monoalcohol and diamine reactants. In other aspects, the hydroxyl equivalents from polyol are less than or equal to 40%, or 30% or 20%, of the total hydroxyl and amine equivalents contributed by the total of the polyol, monoalcohol and diamine reactants.

In one aspect of the invention, the amine equivalents from diamine equal 0.3 to 0.75 of the total amine and hydroxyl equivalents provided by diamine, polyol and monoalcohol. In another aspect, the hydroxyl equivalents from polyol equals 0.05 to 0.45 of the total amine and hydroxyl equivalents provided by diamine, polyol and monoalcohol. In another aspect, the hydroxyl equivalents from monoalcohol equals 0.20 to 0.45 of the total amine and hydroxyl equivalents provided by diamine, polyol and monoalcohol.

For example, in one aspect the invention provides a resin prepared as described herein where the amine equivalents from diamine equals 0.30 to 0.75 of the total amine and hydroxyl equivalents provided by diamine, polyol and monoalcohol; the hydroxyl equivalents from polyol equals 0.05 to 0.45 of the total amine and hydroxyl equivalents provided by diamine, polyol and monoalcohol; and the hydroxyl equivalents from monoalcohol equals 0.20 to 0.45 of the total amine and hydroxyl equivalents provided by diamine, polyol and monoalcohol. As another example, the present invention provides a resin prepared by reacting dibasic acid, diamine, polyol and monoalcohol where polymerized fatty acid constitutes at least 60 equivalent percent of the acid equivalents of the dibasic acid, ethylene diamine constitutes at least 75 equivalent percent of the amine equivalents of the amine; the amine equivalents from diamine equals 0.30 to 0.75 of the total amine and hydroxyl equivalents provided by diamine, polyol and monoalcohol; the hydroxyl equivalents from polyol equals 0.05 to 0.45 of the total amine and hydroxyl equivalents provided by diamine, polyol and monoalcohol; and the hydroxyl equivalents from monoalcohol equals 0.20 to 0.45 of the total amine and hydroxyl equivalents provided by diamine, polyol and monoalcohol.

In one aspect, the present invention provides a method for preparing a resin composition comprising ester-terminated poly(ester-amide), the method comprising reacting w equivalents of hydroxyl from polyol or a reactive equivalent thereof, x equivalents of carboxylic acid from diacid or a reactive equivalent thereof, y equivalents of amine from diamine, and z equivalents of hydroxyl from monoalcohol or a reactive equivalent thereof under reactions conditions to provide a resin composition having an acid number of less than 20 and an amine number of less than 20, wherein at least about 60% of the carboxylic acid equivalents are from polymerized fatty acid, at least about 60% of the amine equivalents are from ethylene diamine, and monoalcohol is substantially the only monofunctional reactant used to form the resin. In a preferred embodiment, $w/(w+y+z)$ is within the range of about 0.05 to 0.60; $y/(w+y+z)$ is within the range of about 0.20 to 0.75; and $z/(w+y+z)$ is within the range of 0.20 to 0.50.

As stated above, the ester-terminated poly(ester-amides) described herein are useful in forming gels with solvents at room temperature, and accordingly preferably have a softening point greater than room temperature. A precise definition of "gel" is not easy to give, although most if not all researchers recognize a "gel." Generally, a gel is more viscous than a liquid or paste, and retains its shape when left undisturbed, i.e., is self-supporting. However, a gel is not as hard or firm as a stick or wax. Gels may be penetrated more easily than a wax-like solid, where "hard" gels are relatively more resistant to penetration than "soft" gels.

Almdale et al. (*Polymer Gels and Networks*, Vol. 1, No. 5 (1993)) list two criteria for defining a system as a gel: (1) a gel consists of two or more components, one of which is a liquid, present in substantial quantities; and (2) a gel is a soft material which is solid or solid-like. This latter requirement can be described more accurately through rheological measurement. Typically, gels possess a storage modulus $G'(w)$ which exhibits a pronounced plateau at higher frequencies (on the order of 1-100 radians/second), and a loss modulus $G''(w)$ which is considerably smaller than the storage modulus in the plateau region. In a strict sense, the term "gel" applies to systems having a value $G'(w)$ that is higher than its value of $G''(w)$ at low frequencies. Many of the compositions according to the present invention are gels by one or both of the above definitions. A gel is free-standing or self-supporting in that its yield value is greater than the sheer stress imposed by gravity.

Accordingly, another aspect of the invention is a gel formed between ingredients comprising ester-terminated poly(ester-amide) as described above and a non-aqueous liquid, preferably a low-polarity liquid. A preferred low polarity liquid is a hydrocarbon, with preferred hydrocarbons being solvents and oils. Solvents and oils may be distinguished in that defatting occurs when solvents are rubbed on human skin, leading to drying and irritation. However, defatting does not occur when oils are rubbed on human skin. Oils are more preferred than solvents in most personal-care formulations, and thus are preferred in forming the gels of the present invention. Preferably, the hydrocarbon has a relatively high number of carbon atoms, e.g., 10 to 30 carbon atoms, and thus is not a volatile hydrocarbon.

A preferred oil is mineral oil, also sometimes referred to as medicinal oil. Mineral oil is a highly refined, colorless, tasteless, and odorless petroleum oil (i.e., derived by processing petroleum/crude oil) used medicinally as an internal lubricant and for the manufacture of salves and ointments. Such mineral oils are highly refined in having substantially all volatile hydrocarbons removed therefrom, and in being hydrogenated (also called hydrotreated) in order to remove substantially all unsaturation, e.g., aromatic groups have been reduced to the fully saturated analog. A preferred mineral oil to prepare a gel of the invention is so-called "white" mineral oil, which is water-white (i.e., colorless and transparent) and is generally recognized as safe for contact with human skin. Mineral oil may also be characterized in terms of its viscosity, where light mineral oil is relatively less viscous than heavy mineral oil, and these terms are defined more specifically in the U.S. Pharmacopoeia, $22^{nd}$ revision, p. 899 (1990). Any mineral oil may be used in the invention to form a gel.

Other hydrocarbons that may be used in the invention include relatively lower molecular weight hydrocarbons including linear saturated hydrocarbons such a tetradecane, hexadecane, octadecane, etc. Cyclic hydrocarbons such as decahydronaphthalene (DECALIN), fuel grade hydrocarbons, branched chain hydrocarbons such as PERMETHYL from Permethyl Corporation and ISOPAR from Exxon Corp., and hydrocarbon mixtures such as product PD-23 from Witco (Greenwich, Conn.) may also be used in preparing gels of the invention. Such hydrocarbons, particularly saturated hydrocarbon oils, are a preferred liquid for preparing a gel of the invention because such hydrocarbons are often less irritating to the skin than liquids containing aromatic, ketone and other functional groups.

Another class of suitable low polarity liquids are esters, and particularly esters of fatty acids. Such esters may be monofunctional esters (i.e., have a single ester moiety) or may be polyfunctional (i.e., have more than one ester group). Suitable esters include, but are not limited to, the reaction products of $C_{1-24}$ monoalcohols with $C_{1-22}$ monocarboxylic acids, where the carbon atoms may be arranged in a linear, branched and/or cyclic fashion, and unsaturation may optionally be present between carbon atoms. Preferably, the ester has at least about 18 carbon atoms. Examples include, but are not limited to, fatty acid esters such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate and tetratriacontanyl stearate; salicylates, e.g., $C_{1-10}$ salicylates such as octyl salicylate, and benzoate esters including $C_{12-15}$ alkyl benzoate, isostearyl benzoate and benzyl benzoate.

Suitable esters are those commonly employed in the cosmetics industry for the formulation of lipstick and make-up, e.g., the fatty acid esters mentioned above, and are often denoted as "cosmetic esters." Other cosmetic esters include glycerol and propylene glycol esters of fatty acids, including the so-called polyglycerol fatty acid esters and triglycerides. Exemplary cosmetic esters include, without limitation, propylene glycol monolaurate, polyethylene glycol (400) monolaurate, castor oil, triglyceryl diisostearate and lauryl lactate. Thus, the liquid may have more than one of ester, hydroxyl and ether functionality. For example, $C_{10-15}$ alkyl lactate may be used in a gel of the invention. In addition, esterified polyols such as the polymers and/or copolymers of ethylene oxide, propylene oxide and butylene oxide reacted with $C_{1-22}$ monocarboxylic acids are useful. The carbon atoms of the $C_{1-22}$ monocarboxylic acids may be arranged in a linear, branched and/or cyclic fashion, and unsaturation may be present between the carbon atoms. Preferred esters are the reaction product of an alcohol and a fatty acid, where the alcohol is selected from $C_{1-10}$ monohydric alcohol, $C_{2-10}$ dihydric alcohol and $C_{3-10}$ trihydric alcohol, and the fatty acid is selected from a $C_{8-24}$ fatty acid.

The gels of the invention preferably do not contain substantial amounts of unreacted monoalcohol, i.e., monohydric alcohols having a single hydroxyl and their only functional group. Thus, the gels of the invention preferably contain less than 25 weight percent, more preferably less than 10 weight percent, and still more preferably less than 5 weight percent of unreacted monoalcohol.

The gels of the invention are preferably self-supporting, in that they retain their shape at room temperature and in the absence of shear. Also, the inventive gels are preferably clear or translucent. The terms clear, transparent and clarity are intended to have their ordinary dictionary definitions; thus, a clear gel allows ready viewing of objects behind it. By contrast, a translucent gel, although allowing light to pass through, causes the light to be so scattered that it will be impossible to see clearly objects behind the translucent stick. As used herein, a gel is transparent or clear if the maximum transmittance of light of any wavelength in the range 400 to 800 nm through a sample 1 cm thick is at least 35%, preferably at least 50% (see, e.g., European Patent Publication No. 291,334 A4). The gel is translucent if the maximum transmittance of such light through the sample is between 2% and less than 35%. The transmittance can be measured by placing a sample of the aforementioned thickness into a light beam of a spectrophotometer whose working range includes the visible spectrum, such as a Bausch & Lomb Spectronic 88 Spectrophotometer.

The gels of the invention preferably do not display syneresis. As defined in the McGraw-Hill Dictionary of Scientific and Technical Terms ($3^{rd}$ Edition), syneresis is the spontaneous separation of a liquid from a gel or colloidal suspension due to contraction of the gel. Typically, syneresis is observed as the separation of liquid from a gel, and is sometimes referred to as "bleeding," in that wetness is seen along the surfaces of a gel that displays syneresis. From a commercial point of view, syneresis is typically an undesirable property, and the gels of the present invention desirably, and surprisingly do not exhibit syneresis.

To prepare a gel of the invention, an ester-terminated poly(ester-amide) resin is combined with a liquid. The two ingredients are taken to elevated temperature, e.g., up to about 80-150° C., until the resin completely dissolves in the liquid. A lower temperature may be used if a solution can be prepared at the lower temperature. Upon cooling, the mixture forms the gel of the invention. Preferably, the liquid is a low-polarity liquid as described above, and more preferably the liquid is a hydrocarbon. The liquid may contain more than one component, e.g., hydrocarbon as well as ester-containing material. In any event, the ester-terminated poly(ester-amide) is combined with the liquid such that the weight percent of ETPEA in the ETPEA+solvent mixture is about 5-50%, and preferably is about 10-45%. Such gels may be transparent, translucent or opaque, depending on the precise identities of the ester-terminated poly(ester-amide) and liquid, as well as the concentration of ETPEA in the mixture.

A commercially desirable aspect of the invention is that the gel may be (although need not be) essentially transparent. Thus, the gels are desirably combined with colorants, as well as other ingredients, to form lipstick and other cosmetic products. The advantage of a clear gel in these applications is that the gel imparts little if any undesirable color to the lipstick or cosmetic. The gels may be combined with aluminum zirconium salts, as well as other ingredients, to form colorless underarm deodorant/antiperspirant, which is currently quite popular. The gels of the invention are also useful in other personal care products, e.g., cosmetics such as eye make-up, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, and suppositories. In addition, the gels may be used in household products such as automobile wax/polish, candles, furniture polish, metal cleaners/polishes, household cleaners, paint strippers and insecticide carriers.

The gels may also be used in industrial products such as fuels (sterno, lighters), toilet bowl rings, lubricants/greases, wire rope lubricant, joint and cable fillers, soldering flux, buffing compounds, crayons and markers, modeling clay, rust preventatives, printing inks, protective/removable coatings, and jet inks. For example, a hydrocarbon oil gelled with an ETPEA resin of the invention may be used as a heat source in, e.g., a cooking apparatus used in camping and hiking. Such a composition will not flow if tilted, and thus may be safer and neater than similar products made from flowing materials.

Formulations to prepare such materials are well known in the art. For example, U.S. Pat. Nos. 3,615,289, 3,645,705, 6,111,055, 6,129,771 and 6,214,063 describe the formulation of candles and pigmented objects embedded in candles referred in the art as "icons." U.S. Pat. Nos. 3,148,125 and 5,538,718 describe the formulation of lipstick and other cosmetic sticks. U.S. Pat. Nos. 4,275,054, 4,937,069, 5,069,897, 5,102,656 and 5,500,209 each describe the formulation of deodorant and/or antiperspirant. Each of these U.S. patents is hereby incorporated herein by reference.

The ETPEA resin of the invention may be incorporated into commercial products such as those listed above by blending the ETPEA resin with the other components of the product. Typically, the ETPEA resin will be present at a concentration of about 1% to about 50% of the composition, based on the total weight of the composition. It is a routine matter to optimize the amount of ETPEA resin to have present in a composition, and indeed the amount will vary depending on the actual product and the desired consistency of the product. In general, as more ETPEA resin is used in a formulation, the product will display a more pronounced gel character.

In one aspect, the present invention provides a composition, in particular a physiologically acceptable composition, comprising at least one liquid fatty phase structured with ETPEA, combined with at least one amphiphilic compound with a hydrophilic/lipophilic balance (HLB) value of, in various embodiments of the invention, less than 16, less than 14, less than 12, less than 10, less than 9, less than 8, less than 7, less than 6. This composition can be in the form of, e.g., a stick of lipstick. Wax is optionally present in the composition: in one aspect wax is present, while in another aspect wax is absent. The composition demonstrates good impact strength and, when applied to a surface, provides a glossy, non-migrating deposit.

For example, the present invention provides a structured composition comprising: (a) at least one liquid fatty phase comprising: (i) ETPEA; and (ii) at least one amphiphilic compound which is liquid at room temperature and which has an HLB value of less than 16, preferably less than 8. One or more of the following features may optionally be used to characterize the composition and/or components thereof:

(a) the at least one amphiphilic compound comprises at least one lipophilic part bonded to at least one polar part; where optionally
  i) the at least one lipophilic part comprises a carbon-based chain comprising at least 8 carbon atoms; or
  ii) the at least one lipophilic part comprises from 16 to 32 carbon atoms; or
  iii) the at least one lipophilic part comprises from 18 to 28 carbon atoms;
  iv) the at least one polar part is chosen from compounds derived from alcohols comprising from 1 to 12 hydroxyl groups, polyol groups comprising from 2 to 12 hydroxyl groups, and polyoxyalkylene groups comprising at least 2 oxyalkylene units; where optionally the polyoxyalkylene groups are chosen from polyoxyalkylene groups which comprise from 0 to 20 oxypropylene units and from 0 to 20 oxyethylene units.

(b) the at least one amphiphilic compound is chosen from esters where optionally
  the esters are chosen from hydroxystearates of glycerol, oleates of glycerol, isostearates of glycerol, hydroxystearates of sorbitan, oleates of sorbitan, isostearates of sorbitan, hydroxystearates of methylglucose, oleates of methylglucose, isostearates of methylglucose, hydroxystearates of branched $C_{12}$ to $C_{26}$ fatty alcohols, oleates of branched $C_{12}$ to $C_{26}$ fatty alcohols and isostearates of branched $C_{12}$ to $C_{26}$ fatty alcohols; where optionally the branched $C_{12}$ to $C_{26}$ fatty alcohols are chosen from octyldodecanols.
  the esters are chosen from monoesters and diesters.

(c) the at least one amphiphilic compound is present in a concentration ranging from 0.1% to 35% by weight of the total weight of said composition, or is present in a concentration ranging from 2% to 15% by weight of the total weight of said composition.

(d) the at least one structuring polymer is present in a concentration ranging from 0.5% to 80% by weight of the total weight of the composition, or is present in a concentration ranging from 5% to 40% by weight of the total weight of said composition.

(e) the at least one liquid fatty phase comprises greater than 40% by weight of the total weight of said at least one liquid fatty phase of at least one apolar oil; or optionally the at least one liquid fatty phase comprises greater than 50% by weight of the total weight of said at least one liquid fatty phase of at least one apolar oil.

(f) the at least one liquid fatty phase comprises at least one oil, where optionally the at least one oil is chosen hydrocarbon-based oils of mineral origin and hydrocarbon-based oils of synthetic origin.

(g) the at least one liquid fatty phase comprises at least one apolar oil, where optionally the at least one apolar oil is chosen from parleam oil, isoparaffins and squalane.

(h) the at least one liquid fatty phase is present in a concentration ranging from 5% to 99% by weight of the total weight of said composition, or optionally the at least one liquid fatty phase is present in a concentration ranging from 20% to 75% by weight of the total weight of said composition.

(i) the composition further comprises at least one suitable additive chosen from water optionally thickened or gelled with an aqueous-phase thickener or gelling agent, antioxidants, essential oils, preserving agents, fragrances, neutralizing agents, liposoluble polymers, cosmetically active agents, dermatologically active agents and waxes.

(j) the composition is in a form chosen from a paste, a solid, a cream, an oil-in-water emulsion, a water-in-oil emulsion and an anhydrous gel, optionally translucent or transparent.

(k) the composition further comprises at least one pigment.

(l) the at least one amphiphilic compound has an HLB value ranging from 1 to 16, or ranging from 1 to 10, or ranging from 1 to 7, or ranging from 1 to 5, or ranging from 3 to 12, or ranging from 3 to 5.

(m) the at least one structuring polymer further comprises a polymer resulting from at least one polycondensation reaction between at least one dicarboxylic acid comprising at least 32 carbon atoms and at least one diamine comprising at least 2 carbon atoms, where, in further optional embodiments:
  i) the at least one dicarboxylic acid comprises from 32 to 44 carbon atoms; and/or
  ii) the said at least one diamine comprises from 2 to 36 carbon atoms; and/or
  iii) the at least one dicarboxylic acid is chosen from dimers of at least one fatty acid comprising at least 16 carbon atoms; and/or
  iv) the at least one fatty acid is chosen from oleic acid, linoleic acid and linolenic acid; and/or
  v) the at least one diamine is chosen from ethylenediamine, hexylenediamine, hexamethylenediamine, phenylenediamine and ethylenetriamine; and/or
  vi) the at least one structuring polymer comprises a polymer comprising one or two terminal carboxylic acid groups, where these terminal groups are optionally esterified with at least one alcohol chosen from monoalcohols comprising at least 4 carbon atoms (e.g., at least one alcohol is chosen from monoalcohols comprising from 10 to 36 carbon atoms, or at least one alcohol is chosen from monoalcohols comprising from 12 to 24 carbon atoms, or at least one alcohol is chosen from monoalcohols comprising from 16 to 24 carbon atoms).
  (n) the ETPEA has a softening point of greater than 70° C., for example, has a softening point of 70° C. to 190° C., or has a softening point of 80° C. to 130° C., or has a softening point of 80° C. to 105° C.
  (o) the composition has a hardness ranging from 20 g to 2000 g, for example, has a hardness ranging from 20 g to 900 g, or has a hardness ranging from 20 g to 600 g.

As another example, the present invention also provides a composition comprising: (a) at least one liquid fatty phase comprising: (i) at least one structuring polymer comprising a polyamide skeleton which comprises at least one end group with at least one chain chosen from alkyl chains comprising at least four carbon atoms and alkenyl chains comprising at least four carbon atoms, bonded to the skeleton via at least one ester group; and (ii) at least one amphiphilic compound which is liquid at room temperature and which has an HLB value of less than 16, preferably less than 8. This composition may be used, for example, to care for at least one keratin material, or for treating at least one keratin material, or may be present in a make-up composition for at least one keratin material.

As another example, the present invention provides a mascara product, an eyeliner product, a foundation product, a lipstick product, a deodorant product, a make-up product for the body, a make-up-removing product, an eyeshadow product, a face powder product, a concealer product, a treating shampoo product, a hair conditioning product, an antisun product or a care product for the face or the body comprising: (a) at least one liquid fatty phase comprising: (i) EPTEA; and (ii) at least one amphiphilic compound which is liquid at room temperature and which has an HLB value of less than 16, preferably less than 8.

As another example, the present invention provides a structured composition comprising a cosmetically acceptable medium and further comprising: (a) at least one liquid fatty phase comprising at least one structuring polymer which comprises ETPEA; and (b) at least one amphiphilic compound which is liquid at room temperature, with an HLB value of less than 16, preferably less than 8. Optionally, the composition is in cast form, and also optionally the composition is in the form of a mascara product, an eyeliner product, a foundation product, a lipstick product, a deodorant product, a make-up product for the body, a make-up-removing product, an eyeshadow product, a face powder product, a concealer product, a treating shampoo product, a hair conditioning product, an antisun product or a care product for the face or the body.

One or more of the following features may optionally be used to characterize the composition and/or components thereof: the composition may further comprise at least one dyestuff, where optionally: i) the at least one dyestuff is chosen from lipophilic dyes, hydrophilic dyes, pigments and nacres, or ii) the at least one dyestuff is present in a concentration ranging from 0.01% to 40% by weight relative to the total weight of said composition, or the at least one dyestuff is present in a concentration ranging from 5% to 25% by weight relative to the total weight of said composition.

The present invention also provides a cosmetic process for caring for, making up or treating a keratin material comprising the application to at least one keratinous material of a cosmetic composition comprising: (a) at least one liquid fatty phase comprising: (i) at least one structuring polymer comprising ETPEA; and (ii) at least one amphiphilic compound which is liquid at room temperature and which has an HLB value of less than 16, preferably less than 8.

The present invention also provides a process of structuring a liquid fatty phase in the form of a self-supporting solid comprising including in said at least one liquid fatty phase a sufficient amount of (i) at least one structuring polymer comprising ETPEA, and (ii) at least one amphiphilic compound which is liquid at room temperature having an HLB value of less than 16, preferably less than 8; and wherein said self-supporting solid is obtained. In optional embodiments, the self-supporting solid has a hardness ranging from 20 g to 2000 g, e.g., has a hardness ranging from 20 g to 900 g, or has a hardness ranging from 20 g to 600 g.

The present invention also provides a process of structuring at least one liquid fatty phase in the form of a glossy and/or non-migrating solid comprising combining with said at least one liquid fatty phase a sufficient amount of (i) at least one structuring polymer comprising ETPEA, and (ii) at least one amphiphilic compound which is liquid at room temperature having an HLB value of less than 16, preferably less than 8; wherein said glossy and/or non-migrating solid is obtained.

The present invention also provides a process of structuring a cosmetic composition in the form of a physiologically acceptable composition which is glossy and/or non-migrating comprising including in said composition at least one liquid fatty phase, said at least one liquid fatty phase being structured with at least one structuring polymer comprising ETPEA and (ii) at least one amphiphilic compound having an HLB value of less than 16, preferably less than 8; wherein said glossy and/or non-migrating cosmetic composition is obtained.

The present invention also provides a process of making a cosmetic composition in the form of a physiologically acceptable composition which is glossy and/or non-migrating comprising including in said composition at least one liquid fatty phase, said at least one liquid fatty phase being structured with at least one structuring polymer comprising ETPEA and (ii) at least one amphiphilic compound having an HLB value of less than 16, preferably less than 8; wherein said glossy and/or non-migrating cosmetic composition is obtained.

In one aspect, the present invention provides a composition comprising, in a physiologically acceptable medium, at least one first polymer with a weight-average molecular mass of less than 100,000 (optionally less than 50,000, optionally less than 30,000, optionally 2,000-20,000, optionally 2,000-10,000) comprising ETPEA, and a dispersion of particles of a second film-forming polymer that is insoluble in said medium.

The second film-forming polymer, which is different from the first polymer comprising EPTEA, is in the form of solid particles dispersed in the physiologically acceptable medium. These particles may be dispersed in an aqueous phase or in a liquid fatty phase. The composition can comprise a mixture of these second polymers. The second film-forming polymer is insoluble in the medium of the composition, that is to say that it remains in the form of particles in the mixture of the ingredients of the composition forming the physiologically acceptable medium. Thus, the expression "polymer that is insoluble in the physiologically acceptable medium" should be understood as meaning a polymer whose solubility in this medium is less than 1% by weight. The second film-forming polymer may be present in the composition according to the invention in a solids content ranging from 0.1% to 60% by weight relative to the total weight of the composition, preferably from 0.5% to 40% by weight and better still from 1% to 30% by weight. The expression "film-forming polymer" means a polymer, which is capable, by itself or in the presence of an auxiliary film-forming agent, of forming a continuous and adherent film on a support, in particular on keratin materials. A film-forming polymer capable of forming a hydrophobic film, i.e., a polymer whose film has a water-solubility at 25° C. of less than 1% by weight, is preferably used.

Among the film-forming polymers, which may be used in the composition of the present invention, mention may be made of synthetic polymers, of radical-mediated type or of polycondensate type, and polymers of natural origin, and mixtures thereof. The expression "radical-mediated film-forming polymer" means a polymer obtained by polymerization of monomers containing unsaturation, in particular ethylenic unsaturation, each monomer being capable of homopolymerizing (unlike polycondensates). The film-forming polymers of radical-mediated type may be, in particular, vinyl polymers or copolymers, in particular acrylic polymers. The vinyl film-forming polymers can result from the polymerization of monomers containing ethylenic unsaturation and containing at least one acidic group and/or esters of these acidic monomers and/or amides of these acidic monomers. Monomers bearing an acidic group that may be used include α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid. The esters of acidic monomers are advantageously chosen from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl. Among the alkyl(meth)acrylates which may be mentioned are methyl methacrylate, ethyl methacrylate, butyl methacrylate, isobutyl methacrylate, 2-ethylhexyl methacrylate, lauryl methacrylate and cyclohexyl methacrylate. Among the hydroxyalkyl (meth)acrylates which may be mentioned are hydroxyethyl acrylate, 2-hydroxypropyl acrylate, hydroxyethyl methacrylate and 2-hydroxypropyl methacrylate. Among the aryl (meth)acrylates which may be mentioned are benzyl acrylate and phenyl acrylate. The (meth)acrylic acid esters that are particularly preferred are the alkyl(meth)acrylates. The alkyl group of the esters may be either fluorinated or perfluorinated, i.e., some or all of the hydrogen atoms of the alkyl group are substituted with fluorine atoms. As amides of the acidic monomers, mention may be made, for example, of (meth)acrylamides, and especially N-alkyl(meth)acrylamides, in particular of a $C_2$-$C_{12}$ alkyl. Among the N-alkyl(meth)acrylamides which may be mentioned are N-ethylacrylamide, N-t-butylacrylamide, N-t-octylacrylamide and N-undecylacrylamide. The vinyl film-forming polymers can also result from the homopolymerization or copolymerization of monomers chosen from vinyl esters and styrene monomers. In particular, these monomers may be polymerized with acidic monomers and/or esters thereof and/or amides thereof, such as those mentioned above. Examples of vinyl esters which may be mentioned are vinyl acetate, vinyl neodecanoate, vinyl pivalate, vinyl benzoate and vinyl t-butylbenzoate. Styrene monomers which may be mentioned are styrene and α-methylstyrene. It is possible to use any monomer known to those skilled in the art which falls within the categories of acrylic and vinyl monomers (including monomers modified with a silicone chain). Among the film-forming polycondensates which may be mentioned are polyurethanes, polyesters, polyesteramides, polyamides, epoxy ester resins and polyureas. The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea-polyurethanes, and mixtures thereof. The polyesters may be obtained, in a known manner, by polycondensation of dicarboxylic acids with polyols, in particular diols. The dicarboxylic acid may be aliphatic, alicyclic or aromatic. Examples of such acids which may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norboranedicarboxylic acid, diglycolic acid, thiodipropionic acid, 2,5-naphthalenedicarboxylic acid and 2,6-naphthalenedicarboxylic acid. These dicarboxylic acid monomers may be used alone or in combination with at least two dicarboxylic acid monomers. Among these monomers, the ones preferably chosen are phthalic acid, isophthalic acid and terephthalic acid. The diol may be chosen from aliphatic, alicyclic and aromatic diols. The diol preferably used is one chosen from: ethylene glycol, diethylene glycol, triethylene glycol, 1,3-propanediol, cyclohexanedimethanol, 4-butanediol. Other polyols which may be used are glycerol, pentaerythritol, sorbitol and trimethylolpropane. The polyesteramides may be obtained in a manner analogous to that of the polyesters, by polycondensation of diacids with diamines or amino alcohols. Diamines which may be used are ethylenediamine, hexamethylenediamine and meta- or para-phenylenediamine. An aminoalcohol which may be used is monoethanolamine. The polyester may also comprise at least one monomer bearing at least one group —$SO_3M$, with M representing a hydrogen atom, an ammonium ion $NH_4+$ or a metal ion such as, for example, an $Na+$, $Li+$, $K+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may be used in particular. The aromatic nucleus of the difunctional aromatic monomer also bearing a group —$SO_3M$ as described above may be chosen, for example, from benzene, naphthalene, anthracene, biphenyl, oxybiphenyl, sulfonylbiphenyl and methylenebiphenyl nuclei. As examples of difunctional aromatic monomers also bearing a group —SO$_3$M, mention may be made of: sulfoisophthalic acid, sulfoterephthalic acid, sulfophthalic acid, 4-sulfonaphthalene-2,7-dicarboxylic acid. The copolymers preferably used are those based on isophthalate/sulfoisophthalate, and more particularly copolymers obtained by condensation of diethylene glycol, cyclohexanedimethanol, isophthalic acid and sulfoisophthalic acid. Such polymers are sold, for example, under the brand name Eastman AQ® by the company Eastman Chemical Products. The polymers of natural origin, optionally modified, may be chosen from shellac resin, sandarac gum, dammar resins, elemi gums, copal resins and cellulose polymers, and mixtures thereof.

According to a first embodiment of the composition according to the invention, the second film-forming polymer may be present in the form of particles in dispersion in an aqueous phase, which is generally known as a latex or pseudolatex. The techniques for preparing these dispersions are well known to those skilled in the art. Aqueous dispersions of film-forming polymers which may be used are the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins; Dow Latex 432® by the company Dow Chemical; Daitosol 5000 AD® by the company Daito Kasey Kogyo; or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich; Impranil 85® by the company Bayer; and Aquamere H-1511® by the company Hydromer. Aqueous dispersions of film-forming polymers which may also be used are the polymer dispersions resulting from the radical-mediated polymerization of one or more radical-mediated monomers within and/or partially at the surface of pre-existing particles of at least one polymer chosen from the group consisting of polyurethanes, polyureas, polyesters, polyesteramides and/or alkyds. These polymers are generally referred to as hybrid polymers.

One or more of the following features may optionally be used to describe the composition of the present invention:

(a) the first polymer is present in a content ranging from 0.01% to 10% by weight, relative to the total weight of the composition, preferably ranging from 0.05% to 5% by weight and better still ranging from 0.1% to 3% by weight.

(b) the second film-forming polymer is chosen from the group formed by free-radical polymers, polycondensates and polymers of natural origin, and blends thereof.

(c) the second film-forming polymer is chosen from the group formed by vinyl polymers, polyurethanes, polyesters and cellulose polymers.

(d) the composition comprises an aqueous phase, optionally:
  i) the aqueous phase comprises water and a water-miscible organic solvent, where the water-miscible organic solvent is optionally chosen from the group formed by lower monoalcohols containing from 1 to 5 carbon atoms, glycols containing from 2 to 8 carbon atoms, $C_3$-$C_4$ ketones and $C_2$-$C_4$ aldehydes.
  ii) the composition comprises a water-miscible organic solvent chosen from the group ethanol, isopropanol, propylene glycol, ethylene glycol, 1,3-butylene glycol and dipropylene glycol.
  iii) the composition comprises water in a content ranging from 5% to 90% by weight relative to the total weight of the composition.

(e) the second film-forming polymer is present in the form of particles dispersed in an aqueous phase.

(f) the composition comprises an aqueous phase that comprises an additional water-soluble film-forming polymer. Examples of water-soluble film-forming polymers which may be mentioned are: proteins, for instance proteins of plant origin such as wheat proteins and soybean proteins; proteins of animal origin such as keratins, for example keratin hydrolysates and sulfonic keratins; anionic, cationic, amphoteric or nonionic chitin or chitosan polymers; polymers of celluloses such as hydroxyethylcellulose, hydroxypropylcellulose, methylcellulose, ethylhydroxyethylcellulose and carboxymethylcellulose, and quaternized cellulose derivatives; acrylic polymers or copolymers, such as polyacrylates or polymethacrylates; vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol; polymers of natural origin, which are optionally modified, such as: (a) gum arabics, guar gum, xanthan derivatives, karaya gum; (b) alginates and carrageenans; (c) glycoaminoglycans, hyaluronic acid and derivatives thereof; (d) shellac resin, sandarac gum, dammar resins, elemi gums and copal resins; (e) deoxyribonucleic acid; (f) mucopolysaccharides such as hyaluronic acid and chondroitin sulfate, and mixtures thereof.

(g) the composition comprises a liquid fatty phase, where optionally
  i) the liquid fatty phase comprises an oil chosen from the group formed by oils of mineral, animal, plant or synthetic origin, that are hydrocarbon-based, fluorinated and/or silicone-based, alone or as a mixture.
  ii) the composition comprises an oil that is volatile at room temperature, optionally chosen from hydrocarbon-based volatile oils containing from 8 to 16 carbon atoms, where the volatile oil is optionally present in a content ranging from 0.1% to 98% and preferably ranging from 1% to 65% by weight, relative to the total weight of the composition.
  iii) the liquid fatty phase is present in a content ranging from 2% to 98% by weight and preferably ranging from 5% to 85% by weight, relative to the total weight of the composition.

(h) the second film-forming polymer is present in the form of particles dispersed in a liquid fatty phase and surface-stabilized, where optionally:
  i) the polymer particles are stabilized with a stabilizer chosen from block polymers, grafted polymers and random polymers, and blends thereof.
  ii) the stabilizer is a grafted-block or block polymer, comprising at least one block resulting from the polymerization of ethylenic monomers comprising one or more optionally conjugated ethylenic bonds, and at least one block of a styrene polymer.

(i) the second film-forming polymer is present in a content ranging from 0.1% to 60% by weight and preferably from 10% to 45% by weight, relative to the total weight of the composition.

(j) the size of the particles of the second film-forming polymer ranges from 5 nm to 600 nm and preferably from 20 nm to 300 nm.

(k) the composition comprises at least one wax, where optionally:
  i) at least one wax has a melting point of greater than 30° C., and less than about 120° C.; and/or
  ii) the wax is chosen from the group formed by beeswax, lanolin wax, Chinese insect waxes, rice wax, carnauba wax, candelilla wax, ouricury wax, cork fiber wax, sugar cane wax, Japan wax, sumach wax, montan wax, microcrystalline waxes, paraffin waxes, ozokerites, ceresin wax, lignite wax, polyethylene waxes and the waxes obtained by Fisher-Tropsch synthesis, fatty acid esters of glycerides that are solid at 40° C., waxes obtained by catalytic hydrogenation of animal or plant oils containing linear or branched $C_8$-$C_{32}$ fatty chains, silicone waxes and fluoro waxes, and mixtures thereof; and/or
  iii) the wax is present in a content ranging from 0.1% to 50% by weight, relative to the total weight of the composition, preferably from 0.5% to 30% by weight and better still from 1% to 20% by weight.

(l) the composition comprises at least one dyestuff, for example, a dyestuff chosen from pigments, nacres, liposoluble dyes and water-soluble dyes, and mixtures thereof. Optionally, the dyestuff is present in a proportion of from 0.01% to 50% relative to the total weight of the composition, preferably ranging from 0.01% to 30% by weight.

(m) The composition is formulated as a personal care composition or make-up composition for keratin materials.

(n) The composition comprises at least one additive chosen from antioxidants, fillers, preserving agents, fragrances, neutralizing agents, thickeners and cosmetic or dermatological active agents, and mixtures thereof.

(o) The composition is formulated as a mascara, an eyeliner, a product for the eyebrows, a product for the lips, a face powder, an eyeshadow, a foundation, a make-up product for the body, a concealer product, a nail varnish, a skincare product or a hair care product.

(p) These compositions of the present invention may be used for the making up or caring for the keratin materials of human beings. For instance, they may be used to obtain a deposit which adheres to keratin materials and/or a quick make-up result on keratin materials. When formulated as a mascara, the composition may thicken quickly when applied to eyelashes, and/or may be used to lengthen the eyelashes.

In one aspect, the present invention provides a colored transparent or translucent cosmetic compositions exhibiting a turbidity of less than 800 NTU and comprising, in a transparent or translucent cosmetic base, an amount of less than 0.5% by weight, with respect to the final cosmetic composition, of at least one colored pigment which is insoluble in the cosmetic base and which has a mean particle size of greater than 100 nm. Optionally, one or more of the following criteria may be used to characterize these compositions of the present invention:

(a) the composition contains pigment or pigments having a mean particle-size of greater than 200 nm; and/or (b) the composition contains pigment and the concentration of the colored pigment or pigments is less than 0.01% by weight with respect to the final cosmetic composition, optionally the concentration of the colored pigment or pigments is at most equal to 0.001% by weight with respect to the final cosmetic composition; and/or (c) the composition exhibits a turbidity of less than 500 NTU.

(d) the transparent or translucent cosmetic base is chosen from aqueous or oily gels, in particular in the form of sticks.

(e) the transparent or translucent cosmetic base is an anhydrous lipophilic cosmetic base.

(f) the transparent or translucent cosmetic base is an anhydrous gel formed of a fatty phase which is liquid at ambient temperature comprising polar and/or nonpolar oils, which fatty phase is structured by a gelling agent for fatty phases comprising ETPEA and optionally one or more other gellants chosen from hydrophobic pyrogenic silicas, gelling polyamides, hydrophobic galactomannans, and their mixtures.

(g) the composition additionally comprises physiologically acceptable additives chosen from dispersing agents, fragrances, sunscreen agents, preservatives, antioxidants and cosmetic active principles.

In one aspect, the present invention provides a structured nail polish composition comprising at least one liquid organic phase comprising at least one volatile organic solvent, the liquid organic phase being structured by at least one first polymer comprising ETPEA. The ETPEA preferably has a weight-average molecular mass of less than or equal to 100 000. In a related aspect, the present invention provides a stick nail polish composition comprising at least one liquid organic phase comprising at least one volatile organic solvent, the liquid organic phase being structured by at least one first polymer comprising ETPEA. The ETPEA preferably has a weight-average molecular mass of less than or equal to 100 000. In a related aspect, the present invention provides a cosmetic composition comprising an organic phase, a first polymer comprising ETPEA and a second additional film-forming polymer, the organic phase comprising at least one volatile organic solvent or a mixture of volatile organic solvents exhibiting mean Hansen solubility parameters dD, dP and dH at 25° C. which satisfy the following conditions: $15\ (J/cm^3)^{1/2} \leq dD \leq 19\ (J/cm^3)^{1/2}$; $dP \leq 10\ (J/cm^3)^{1/2}$; $dH \leq 10\ (J/cm^3)^{1/2}$. In a related aspect, the present invention provides a nail polish composition comprising a liquid organic phase, a first polymer comprising ETPEA and a second additional film-forming polymer, the organic phase comprising at least one volatile organic solvent or a mixture of volatile organic solvents exhibiting mean Hansen solubility parameters dD, dP and dH at 25° C. which satisfy the following conditions: $15\ (J/cm^3)^{1/2} \leq dD \leq 19\ (J/cm^3)^{1/2}$; $dP \leq 10\ (J/cm^3)^{1/2}$; $dH \leq 10\ (J/cm^3)^{1/2}$. Otionally, in each of these four aspects, the composition or a component thereof may be further characterized or defined by reference to one or more of the following criteria:

(a) the volatile organic solvent is chosen from volatile organic solvents or mixtures of volatile organic solvents exhibiting mean Hansen solubility parameters dD, dP and dH at 25° C. which satisfy the following conditions: $15\ (J/cm^3)^{1/2} \leq dD \leq 19\ (J/cm^3)^{1/2}$; $dP \leq 10\ (J/cm^3)^{1/2}$; $dH < 10\ (J/cm^3)^{1/2}$.

(b) $dP \leq 5\ (J/cm^3)^{1/2}$.

(c) $dH \leq 9\ (J/cm^3)^{1/2}$.

(d) The square root of $(4(17-dD)^2 + dP^2 + dH^2)$ is less than L, where L is equal to $10\ (J/cm^3)^{1/2}$ and better still L is $9\ (J/cm^3)^{1/2}$.

(e) The volatile organic solvent is chosen from the group formed by esters having from 4 to 8 carbon atoms and alkanes having from 6 to 10 carbon atoms.

(f). The volatile organic solvent is chosen from the group formed by ethyl acetate, n-propyl acetate, isobutyl acetate, n-butyl acetate and heptane.

(g) The volatile organic solvent is chosen from branched C8-C16 alkanes, branched C8-C16 esters and mixtures thereof.

(h) The volatile organic solvent is chosen from C8-C16 isoparaffins, isododecane and their mixtures.

(i) The volatile organic solvent is present in a content ranging from 20% to 98% by weight with respect to the total weight of the composition, preferably from 30% to 90% by weight and better still from 40% to 85% by weight.

(j) The liquid organic phase additionally comprises at least one nonvolatile oil.

(k) The liquid organic phase represents from 5 to 99% of the total weight of the composition, preferably from 20 to 75%.

(l) The composition further comprises a second film-forming polymer, where optionally:
  i) the second film-forming polymer is chosen from the group formed by cellulose polymers, polyurethanes, acrylic polymers, vinyl polymers, polyvinylbutyrals, alkyd resins, resins resulting from aldehyde condensation products, and arylsulfonamide-epoxy resins; and/or
  ii) the second film-forming polymer is present in a content ranging from 0.1% to 60% by weight with respect to the total weight of the composition, preferably ranging from 2% to 40% by weight and better still from 5% to 25% by weight.

(m) The composition further comprises at least one additive chosen from coloring materials, antioxidants, preservatives, fragrances, fillers, waxes, neutralizing agents, cosmetic or dermatological active principles, dispersing agents, spreading agents, sunscreens, and their mixtures.

(n) The composition is provided in the form of a stiff gel and in particular of an anhydrous stick.

(o) The composition has a hardness ranging from 30 to 300 g, measured by the "cheesewire" method described herein.

In one aspect, the present invention provides a composition, preferably a transfer resistant composition, which may also be pliable and comfortable to wear upon application to skin or other substrate. The compositions comprise at least one structuring polymer including ETPEA and at least one film-forming silicone resin. The compositions are optionally anhydrous.

Optional components of the compositions include, without limitation, at least one liquid fatty phase, the phase optionally comprising an oil (e.g., a polar oil, an apolar oil) having affinity for the ETPEA, non-volatile oil, silicone oil, a second fatty material (e.g., gum, fatty materials pasty), fatty alcohol (e.g., myristyl alcohol, cetyl alcohol, stearyl alcohol, behenyl alcohol), oil-soluble polymer (e.g., alkylated guar gum, alkyl cellulose), oil-soluble cationic surfactant (e.g., quaternary ammonium compounds, fatty amines, salts of fatty amines), wax (e.g., carnauba wax, candelilla wax, ouricury wax, microcrystalline waxes, lanolin wax, silicon wax, jojoba oil, etc.), fatty acid (e.g., oleic acid, linoleic acid, linolenic acid), siloxysilicate, and silsesquioxanes.

In one aspect the present invention provides compositions and methods wherein ETPEA is present in a make-up composition comprising a physiologically acceptable medium containing a fatty phase, as an agent for increasing the speed of achieving a make-up result on keratin materials and/or for increasing the adhesion to said keratin materials and/or for rapidly increasing the amount of make-up deposited on the keratin materials. In a related aspect, the present invention provides compositions and methods wherein ETPEA is present in a composition for express make-up and/or with good adhesion to and/or that loads quickly onto keratin materials, said composition comprising a physiologically acceptable medium containing a fatty phase. Optionally, one or more of the following criteria may further define these compositions and methods:

(a) the fatty phase contains at least one wax, e.g., a wax chosen from the group formed by beeswax, lanolin wax, Chinese insect waxes, rice wax, carnauba wax, candelilla wax, ouricury wax, cork fiber wax, sugar cane wax, Japan wax, sumach wax, montan wax, microcrystalline waxes, paraffin waxes, ozokerites, ceresin wax, lignite wax, polyethylene waxes and the waxes obtained by Fisher-Tropsch synthesis, fatty acid esters and glycerides that are solid at 40° C., the waxes obtained by catalytic hydrogenation of animal or plant oils containing linear or branched C8-C32 fatty chains, silicone waxes and fluoro waxes, and mixtures thereof, where the wax is optionally present in a content ranging from 0.1% to 50% by weight, relative to the total weight of the composition, preferably from 0.5% to 30% by weight and better still from 1% to 20% by weight.

(b) the fatty phase comprises at least one oil, e.g., an oil chosen from the group formed by oils of mineral, animal, plant or synthetic origin, that are hydrocarbon-based, fluorinated and/or silicone-based, alone or as a mixture. The oil is optionally a volatile oil, e.g., a volatile oil chosen from hydrocarbon-based volatile oils containing from 8 to 16 carbon atoms, where the volatile oil is optionally present in a content ranging from 0.1% to 98% by weight and preferably ranging from 1% to 65% by weight, relative to the total weight of the composition.

(c) the composition comprises an aqueous phase containing water or a mixture comprising water and a water-miscible organic solvent.

(d) The composition comprises a second film-forming polymer that is different than the first polymer. The second film-forming polymer may be chosen from the group formed by vinyl polymers, polyurethanes, polyesters, polyamides, polyureas and cellulose polymers. Optionally, the second film-forming polymer is present in a solids content ranging from 0.1% to 60% by weight, preferably from 0.5% to 40% by weight and better still from 1% to 30% by weight, relative to the total weight of the composition.

(e) The composition contains at least one dyestuff, e.g., a dyestuff chosen from pigments, nacres, water-soluble dyes and liposoluble dyes, and mixtures thereof, where optionally the dyestuff is present in a proportion of from 0.01% to 50% relative to the total weight of the composition, preferably ranging from 0.01% to 30% by weight.

(f) The composition contains at least one additive chosen from surfactants, thickeners, antioxidants, fillers, preserving agents, fragrances, neutralizing agents and cosmetic or dermatological active agents, and mixtures thereof.

(g) The composition is in the form of a mascara, an eyeliner, a product for the eyebrows, a product for the lips, a face powder, an eyeshadow, a foundation, a make-up product for the body, a concealer product, a nail varnish or a hair care product.

The compositions of the present invention may contain one or more apolar oils, where representative apolar oils according to the present invention may be chosen from silicone oils such as volatile and nonvolatile, linear, branched and cyclic polydimethylsiloxanes (PDMSs) that are liquid at room temperature; polydimethylsiloxanes comprising groups chosen from alkyl groups, alkoxy groups and phenyl groups, optionally pendant or terminal, and each comprising from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; linear, branched and cyclic, volatile and nonvolatile hydrocarbons and fluorocarbons of synthetic and mineral origin, such as volatile liquid paraffins (such as isoparaffins and isododecane), nonvolatile liquid paraffins and derivatives thereof, petroleum jelly, polydecenes, hydrogenated polyisobutene such as parleam, and squalane. In one embodiment, the apolar oil is chosen from those of the hydrocarbon-based type chosen from mineral and synthetic origin. In another embodiment, the apolar oil is chosen from parleam oil, isoparaffins, squalane and mixtures thereof.

The compositions of the present invention may contain one or more polar oils. For example, it may be possible to add polar oils to the apolar oils, the apolar oils acting in particular as co-solvent for the polar oils. Representative polar oils of the present invention may be chosen from: hydrocarbon-based plant oils having a high content of triglycerides chosen from fatty acid esters of glycerol in which the fatty acids may have varied chain lengths, these chains may be chosen from linear, branched, cyclic, saturated and unsaturated chains. Non-limiting examples of these oils are wheat germ oil, corn oil, sunflower oil, karite buffer, castor oil, sweet almond oil, macadamia oil, apricot oil, soybean oil, rape seed oil, cotton oil, alfalfa oil, poppy oil, pumpkin oil, sesame oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil, musk rose oil and caprylic/capric acid triglycerides such as those sold by Stearineries Dubois Co. and those sold under the names Miglyol 810, 812 and 818 by Dynamit Nobel Co.

The compositions of the present invention may contain one or more synthetic oils and esters of formula $R_1COOR_2$ in which $R_1$ is chosen from linear and branched higher fatty acid groups comprising from 1 to 40 carbon atoms, such as from 7 to 19 carbon atoms; and $R_2$ is chosen from branched hydrocarbon-based groups comprising from 1 to 40 carbon atoms, such as from 3 to 20 carbon atoms, with the proviso that the total number of carbon atoms in $R_1$ and $R_2$ is greater than or equal to 10, such as, for example, in purcellin oil (cetostearyl octanoate), isononyl isononanoate, $C_{12}$-$C_{15}$ alkyl benzoates, isopropyl myristate, 2-ethylhexyl palmitate, alkyl octanoates, polyalkyl octanoates, decanoates ricinoleates, hydroxylated esters such as isostearyl lactate and diisostearyl malate, and pentaerythritol esters. Optionally, the synthetic ethers comprise from 10 to 40 carbon atoms.

A composition of the present invention may contain emulsifying surfactants. Such surfactants make it possible to obtain an oil-in-water or wax-in-water emulsion. The specific type and amount of such a surfactant may be selected according to routine skill in the art. Typically the surfactant is present in a proportion ranging from 2% to 30% by weight relative to the total weight of the composition, and better still from 5% to 15%. These surfactants may be chosen from, e.g., anionic and nonionic surfactants. Reference may be made to "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of said reference, for the anionic and nonionic surfactants. Exemplary surfactants include, without limitation:

nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated fatty esters of $C_1$-$C_6$ alkyl glucose, and mixtures thereof.

anionic surfactants: $C_{16}$-$C_{30}$ fatty acids neutralized with amines, aqueous ammonia or alkaline salts, and mixtures thereof.

The compositions of the present invention may include a stabilizer, where the stabilizer is useful to, e.g., stabilize polymer particles. Exemplary stabilizers are block polymers, grafted polymers and/or a random polymers, which may be used alone or as a mixture. Dispersions of film-forming polymer in the liquid fatty phase, in the presence of stabilizers, are disclosed in particular in documents EP-A-0 749 746, EP-A-0 923 928 and EP-A-0 930 060, the content of which is incorporated in the present patent application by reference. Among the grafted polymers that may be mentioned are silicone polymers grafted with a hydrocarbon-based chain; hydrocarbon-based polymers grafted with a silicone chain. Grafted copolymers having, for example, an insoluble skeleton of polyacrylic type with soluble grafts of poly(12-hydroxystearic acid) type are also suitable. Grafted-block or block copolymers comprising at least one block of polyorganosiloxane type and at least one block of a free-radical polymer may also be used, for instance grafted copolymers of acrylic/silicone type which may be used especially when the non-aqueous medium is silicone-based. The stabilizer may also be chosen from grafted-block or block copolymers comprising at least one block of polyorganosiloxane type and at least one block of a polyether. The polyorganosiloxane block may especially be a polydimethylsiloxane or a poly(C2-C18)alkylmethylsiloxane; the polyether block may be a C2-C18 polyalkylene, in particular polyoxyethylene and/or polyoxypropylene. In particular, dimethicone copolyols or (C2-C18)alkylmethicone copolyols may be used. It is possible, for example, to use the dimethicone copolyol sold under the name "Dow Corning 3225C" by the company Dow Corning, or the lauryl methicone copolyol sold under the name "Dow Corning Q2-5200" by the company Dow Corning. As grafted-block or block copolymers, use may be made of copolymers comprising at least one block resulting from the polymerization of at least one ethylenic monomer, containing one or more optionally conjugated ethylenic bonds, such as ethylene, butadiene or isoprene, and at least one block of a styrene polymer. When the ethylenic monomer comprises several optionally conjugated ethylenic bonds, the residual ethylenic unsaturations after the polymerization are generally hydrogenated. Thus, in a known manner, the polymerization of isoprene leads, after hydrogenation, to the formation of ethylene-propylene block, and the polymerization of butadiene leads, after hydrogenation, to the formation of ethylene-butylene block. Among these block copolymers, mention may be made of copolymers of "diblock" or "triblock" type, of the type such as polystyrene/polyisoprene, polystyrene/polybutadiene such as those sold under the name "Luvitol HSB" by BASF, of the polystyrene/copoly(ethylene-propylene) type such as those sold under the name "Kraton" by Shell Chemical Co., or alternatively of the polystyrene/copoly(ethylene-butylene) type. As grafted-block or block copolymers comprising at least one block resulting from the polymerization of at least one ethylenic monomer, such as ethylene or isobutylene, and of at least one block of an acrylic polymer such as methyl methacrylate, mention may be made of the poly(methyl methacrylate)/polyisobutylene diblock or triblock copolymers or the grafted copolymers containing a poly(methyl methacrylate) skeleton and polyisobutylene grafts. As grafted-block or block copolymers comprising at least one block resulting from the polymerization of at least one ethylenic monomer and of at least one block of a polyether such as a C2-C18 polyoxyalkylene, in particular polyoxyethylene and/or polyoxypropylene, mention may be made of polyoxyethylene/polybutadiene or polyoxyethylene/polyisobutylene diblock or triblock copolymers. Use may also be made of copolymers of C1-C4 alkyl(meth)acrylates, and of C8-C30 alkyl(meth)acrylates. Mention may be made in particular of the stearyl methacrylate/methyl methacrylate copolymer. When the compositions of the invention include a liquid fatty phase, and silicon oil is present in that phase, the stabilizer is preferably chosen from the group consisting of grafted-block or block copolymers comprising at least one block of polyorganosiloxane type and at least one block of a free-radical polymer or of a polyether or of a polyester, for instance polyoxy(C2-C18)alkylene blocks and especially polyoxypropylene and/or oxyethylene blocks. When the liquid fatty phase does not comprise a silicone oil, the stabilizer is preferably chosen from the group consisting of: (a) grafted-block or block copolymers comprising at least one block of polyorganosiloxane type and at least one block of a free-radical polymer or of a polyether or of a polyester, (b) copolymers of C1-C4 alkyl acrylates or methacrylates and of C8-C30 alkyl acrylates or methacrylates, (c) grafted-block or block copolymers comprising at least one block resulting from the polymerization of at least one ethylenic monomer containing conjugated ethylenic bonds, and at least one block of a vinyl or acrylic polymer or of a polyether or of a polyester, or blends thereof. Diblock polymers may be used as a stabilizer.

The compositions of the present invention may contain one or more pigments. The pigments may be chosen from organic, inorganic or composite pigments. Exemplary inorganic pigments include iron oxides, chromium oxide, chromium hydrate, ultramarines (polysulfides of aluminum silicates), cobalt blue, Prussian blue (ferric ferrocyanide), manganese violet, manganese pyrophosphate and metal powders, such as silver or aluminum powders. Exemplary organic pigments include carbon black, thioindigo and flaming red. Exemplary composite pigments include lakes or salts formed from calcium, barium, aluminum, strontium, zirconium and their mixtures and from organic acid dyes immobilized on an organic or inorganic support, where exemplary lakes include the calcium salt of lithol red B on rosin and barium sulfate (D&C Red No. 7 calcium lake), the aluminum salt of tartrazine on alumina (FD&C Yellow No. 5 aluminum lake), the aluminum salt of eosin on alumina and titanium dioxide (D&C Red No. 21 aluminum lake), the aluminum salt of phloxin B on alumina (D&C Red No. 27 aluminum lake), the aluminum salt of brilliant yellow FCF on alumina (FD&C Yellow No. 6 aluminum lake) and the aluminum salt of brilliant blue on alumina (FD&C Blue No. 1 aluminum lake). Exemplary white pigments include titanium dioxide, zirconium dioxide, cerium dioxide and zinc oxide. The pigment may be coated with materials chosen from silicones, amino acids and fluorinated compounds.

In one aspect, the coloring material according to the invention can be chosen from lipophilic dyes, pigments and pearlescent agents commonly used in cosmetic or dermatological compositions, and their mixtures. The coloring material is generally present in a proportion of 0.01 to 10% of the total weight of the composition, preferably of 0.1 to 8%, if it is present. Fat-soluble dyes are, for example, Sudan red, DC Red 17, DC Green 6, beta-carotene, soybean oil, Sudan brown, DC Yellow 11, DC Violet 2, DC Orange 5 or quinoline yellow. They can typically represent from 0.1 to 10% of the weight of the compositions and better still from 0.1 to 6%. The pigments can be white or colored, inorganic and/or organic and coated or uncoated. Mention may be made, among inorganic pigments, of titanium dioxide, which is optionally surface treated, zirconium or cerium oxides and iron or chromium oxides, manganese violet, ultramarine blue, chromium hydrate and ferric blue. Mention may be made, among organic pigments, of carbon black, pigments of D & C type and lakes based on cochineal carmine or on barium, strontium, calcium or aluminum. The pigments can typically represent from 0.1 to 50% and better still from 2 to 30% of the total weight of the composition, if they are present. The pearlescent pigments can be chosen from white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride. They can typically represent from 0.1 to 20% of the total weight of the composition and better still from 0.1 to 15%, if they are present.

The compositions of the invention may contain a liquid organic phase that comprises at least one volatile organic solvent or a mixture of volatile organic solvents (within the meaning of the final mixture) exhibiting mean Hansen solubility parameters dD, dP and dH at 25° C. which satisfy the following conditions: $15 \, (J/cm^3)^{1/2} \leq dD \leq 19 \, (J/cm^3)^{1/2}$; $dP \leq 10 \, (J/cm^3)^{1/2}$; and $dH < 10 \, (J/cm^3)^{1/2}$. The definition of the solvents the three-dimensional solubility space according to Hansen is described in the article by C. M. Hansen: "The three-dimensional solubility parameters", J. Paint Technol., 39, 105 (1967): dD characterizes the London dispersion forces resulting from the formation of dipoles induced during molecular impacts; dP characterizes the forces of Debye interaction between permanent dipoles and the forces of Keesom interactions between induced dipoles and permanent dipoles; dH characterizes the forces of specific interactions (hydrogen bond, acid/base or donor/acceptor type and the like). The parameters dD, dP and dH are expressed in $(J/cm^3)^{1/2}$.

Suitable volatile organic solvent which may be used in the invention are selected from volatile hydrocarbonaceous oils having from 4 to 16 carbon atoms and their mixtures and in particular linear C6-C10 alkanes, such as n-hexane, n-heptane or n-octane, branched C8-C16 alkanes, C8-C16 isoalkanes (also known as isoparaffins), isododecane, isodecane, isohexadecane and, for example, the oils sold under the tradenames of Isopars or Permethyls, esters having from 4 to 8 carbon atoms, such as ethyl acetate, n-propyl acetate, isobutyl acetate or n-butyl acetate, branched C8-C16 esters, such as isohexyl neopentanoate, and their mixtures. The volatile organic solvent may be chosen from volatile hydrocarbonaceous oils having from 4 to 10 carbon atoms and their mixtures.

Mention may also be made, as to other volatile organic solvents which can be used in the invention, of linear or cyclic silicone oils having a viscosity at ambient temperature of less than 8 centistokes ($8 \times 10^{-6} \, m^2 s$) and having in particular from 2 to 7 silicon atoms, these silicones optionally comprising alkyl or alkoxy groups having from 1 to 10 carbon atoms. Mention may in particular be made, as volatile silicone oil which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

Other suitable volatile organic solvents include volatile fluorinated solvents.

A component of the compositions of the invention may be a polymer added specifically for its film-forming ability. The film-forming polymer can be chosen from cellulose polymers, such as nitrocellulose, cellulose acetate, cellulose acetate butyrate, cellulose acetate propionate or ethyl cellulose, or alternatively polyurethanes, acrylic polymers, vinyl polymers, polyvinylbutyrals, alkyd resins, resins resulting from aldehyde condensation products, such as aryl-sulfonamide-formaldehyde resins, for example toluene-sulfonamide-formaldehyde resin, or arylsulfonamide-epoxy resins. For example, the film-forming polymer may be nitrocellulose RS 1/8 sec.; RS 1/4 sec.; 1/2 sec.; RS 5 sec.; RS 15 sec.; RS 35 sec.; RS 75 sec.; RS 150 sec.; AS 1/4 sec.; AS 1/2 sec.; SS 1/4 sec.; SS 1/2 sec.; SS 5 sec.; sold in particular by Hercules; toluenesulfonamide-formaldehyde resin "Ketjentflex MS80" from Akzo or "Santolite MHP" or "Santolite MS80" from Faconnier or "Resimpol 80" from Pan Americana, alkyd resin "Beckosol ODE 230-70-E" from Dainippon, acrylic resin "Acryloid B66" from Rohm & Haas, or polyurethane resin "Trixene PR 4127" from Baxenden. When present, the film-forming polymer can be present in the composition according to the invention in a content ranging from about 0.1% to 60% by weight with respect to the total weight of the composition, preferably ranging from about 2% to 40% by weight and better still from about 5% to 25% by weight.

In one aspect, the ETPEA-containing composition of the invention contains at least one inert filler. The term "filler" means any particle that is solid at room temperature and atmospheric pressure, used alone or in combination, which does not react chemically with the various ingredients of the composition and which is insoluble in these ingredients, even when these ingredients are raised to a temperature above room temperature and in particular to their softening point or their melting point.

The at least one inert filler has a melting point at least greater than 150° C., for example greater than 170° C. and further as for example, greater than 200° C. The at least one inert filler may or may not be absorbent, i.e., capable in particular of absorbing the oils of the composition and also the biological substances secreted by the skin. The absorbent fillers often have the property of making the deposit of composition on the keratin materials matte, which is particularly desired for a foundation and a concealer product. In one embodiment, the at least one inert filler may have an apparent diameter ranging from 0.01 μm to 150 μm, such as from 0.5 μm to 120 μm, for example from 1 μm to 80 μm. An apparent diameter corresponds to the diameter of the circle into which the elementary particle fits along its shortest dimension (thickness for leaflets).

The at least one inert filler may be present in the inventive composition in an amount ranging from 0.1% to 40% relative to the weight of the total composition, such as from 2% to 30%, and, for example, from 5% to 20%.

The at least one inert filler may be mineral or organic, and lamellar, spherical or oblong. The at least one inert filler may be chosen from talc, mica, silica, kaolin, polyamide powders such as Nylon® (Orgasol® from Atochem) powder, poly-β-alanine powder, polyethylene powder, acrylic polymer powder and in particular polymethyl methacrylate (PMMA) powder, for instance the product sold or made by Wacker under the reference Covabead LH-85 (particle size 10-12 μm) or acrylic acid copolymer powder (Polytrap® from Dow Corning), polytetrafluoroethylene (Teflon®) powders, lauroyllysine, boron nitride, starch, hollow polymer microspheres such as those of polyvinylidene chloride/acrylonitrile, for instance Expancel® (Nobel Industrie), hollow polymer microspheres (Tospearl® from Toshiba, for example), precipitated calcium carbonate, magnesium carbonate and hydrocarbonate, hydroxyapetite, hollow silica microspheres (Silica Beads® from Maprecos), glass or ceramic microcapsules and polyester particles. The at least one inert filler may be surface-treated, e.g., to make them lipophilic.

The at least one inert filler may be porous so as to absorb the sweat and/or sebum secreted by the skin. Such inert fillers include silica, polyethylene powder, polyamide (Nylon®) powder, kaolin, starch derivatives and Polytrap®.

In order to minimize the exudation of the composition in cast form, the at least one inert filler used in the composition may contain a chemical group of the same chemical nature as those of the units of the structuring polymer or a chemical group capable of forming physical bonds of the same type as that of the units of the polymer (for example, chosen from self-complementary hydrogen bonds, π interactions between unsaturated rings or filler-transfer interactions, dipolar interactions, and coordination bonds with organometallic derivatives). Thus, for structuring polymers containing units of the amide, urea and/or urethane type, the at least one inert filler used may contain groups capable of forming hydrogen bonds, like these structuring polymers. As fillers capable of forming hydrogen bonds, mention may be made of fillers or particles of acrylic polymer such as PMMA for instance the product sold by Wacker under the reference Covabead LH-85 (particle size 10-12 μm) and Polytrap® sold, or made by Dow Corning, hydrophobic-treated silica, polyamide (Nylon®) powders (Orgasol® from Atochem), and mixtures thereof. For units of the ester type, the fillers used may be of the polyester type.

The surface of the silica may be chemically modified, by hydrophobic chemical treatments, giving rise to a decrease in the number of silanol groups. The hydrophobic groups may be:
 trimethylsiloxyl groups, which are obtained, for example, by treating fumed silica in the presence of hexamethyldisilazane. Silicas thus treated are known as "silica silylate" according to the CTFA (6th edition, 1995). They are sold, or made for example, under the references "Aerosil R812®" by the company Degussa and "CAB-O-SIL TS-530®" by the company Cabot;
 dimethylsilyloxyl or polydimethylsiloxane groups, which are obtained, for example, by treating fumed silica in the presence of polydimethylsiloxane or dimethyldichlorosilane. Silicas thus treated are known as "silica dimethyl silylate" according to the CTFA (6th edition, 1995). They are made or sold, for example, under the references "Aerosil R972®" and "Aerosil R974®" by the company Degussa, and "CAB-O-SIL TS-610®" and "CAB-O-SIL TS-720®" by the company Cabot;
 groups derived from reacting fumed silica with silane alkoxides or siloxanes. These treated silicas are, for example, the products made or sold under the reference "Aerosil R805®" by the company Degussa.

According to the invention, a hydrophobic silica, such as a fumed silica, may be used as lipophilic gelling agent or rheological agent. The use of fumed silica may make it possible to obtain a translucent or even transparent composition, in particular in the form of a stick which does not exude, in the absence of opacifying particles such as waxes, fillers and pigments (including nacres). In one embodiment, the filler is lipophilic or treated to be lipophilic.

In one aspect, a composition according to the present invention may contain at least one fatty compound that is pasty or viscous at room temperature. For the purposes of the invention, the expression "pasty fatty substance" means a fatty substance with a melting point ranging from 20° C. to 55° C., for example from 25° C. to 45° C., and from 25° C. to 40° C., and/or a viscosity at 40° C. ranging from 0.1 to 40 to 400 poises), for example from 0.5 to 25 Pa·s, measured using a Contraves TV or Rheomat 80 viscometer, equipped with a spindle rotating at 240 $min^{-1}$ for supplying with 60 Hz or at 200 $min^{-1}$ for supplying with 50 Hz. A person skilled in the art can select the spindle for measuring the viscosity from the spindles MS-r3 and MS-r4, on the basis of his general knowledge, so as to be able to carry out the measurement of the pasty compound tested.

According to the invention, at least one pasty fatty substance can be used. The at least one pasty fatty substance may be chosen from hydrocarbon-based compounds, optionally of polymeric type; it can also be chosen from silicone compounds and/or fluoro compounds; it may also be in the form of a mixture of hydrocarbon-based compounds and/or silicone compounds and/or fluoro compounds. In the case of a mixture of different pasty fatty substances, the hydrocarbon-based pasty compounds (containing mainly hydrogen and carbon atoms and optionally ester groups) may be used in major proportion.

Among the pasty compounds which may be used in the composition according to the invention, mention may be made of lanolins and lanolin derivatives such as acetylated lanolins or oxypropylenated lanolins or isopropyl lanolate, having a viscosity of from 18 to 21 Pa·s, for instance 19 to 20.5 Pa·s, and/or a melting point of from 30° C. to 55° C. and for example from 30° C. to 40° C., and mixtures thereof. It is also possible to use esters of fatty acids or of fatty alcohols, such as those containing from 20 to 65 carbon atoms (melting point of about from 20° C. to 35° C. and/or viscosity at 40° C. ranging from 0.1 to 40 Pa·s), such as triisostearyl citrate or cetyl citrate; arachidyl propionate; polyvinyl laurate; cholesterol esters, such as triglycerides of plant origin, such as hydrogenated plant oils (hydrogenated castor oil), viscous polyesters such as poly(12-hydroxystearic acid); polydimethylsiloxanes (PDMS) having alkyl or alkoxy pendant chains containing from 8 to 24 carbon atoms, and a melting point of 20-55° C. and form example form 20° C. to 40° C., such as stearyldimethicones (in particular DC2503 and DC25514 from Dow Corning); and mixtures thereof.

The at least one pasty fatty substance may be present in a proportion up to 60% by weight, relative to the total weight of the composition, for example from 0.5% to 45% by weight, and, as a further example, from 2% to 30% by weight, in the composition, if present.

In one aspect, the present invention provides a personal care composition comprising ETPEA and at least one film-forming silicone resin. In one embodiment, the at least one film-forming silicone resin is chosen from silsesquioxanes and siloxysilicates. The use of silicone polymers or derivatives as film-forming agents in cosmetic compositions is known in the art. See, e.g., U.S. Pat. Nos. 5,965,112, 5,800,816, 5,911,974, and 5,959,009. Silicone resin nomenclature is known in the art as "MDTQ" nomenclature, whereby a silicone resin is described according to the various monomeric siloxane repeating units which make up the polymer. Each letter of "MDTQ" denotes a different type of unit. The symbol M denotes the monofunctional unit $(CH_3)_3SiO_{1/2}$. This unit is considered monofunctional because the silicone atom only shares one oxygen for the formation of the chain. At least one of the methyl groups can be replaced, such as, for example, to give a unit with formula $[R(CH_3)_2]SiO_{1/2}$ where R is other than a methyl group. The symbol "D" denotes the difunctional unit $(CH_3)_2SiO_{2/2}$, where two of the available bonds from the silicone atom are used for binding to oxygen for the formation of the polymeric chain. The "D" unit is the major building block of dimethicone oils. The symbol "T" denotes the trifunctional unit, $(CH_3)SiO_{3/2}$, where three of the available bonds from the silicone atom are used for binding to oxygen for the formation of the polymeric chain. As in the "M" unit, any methyl group could be replaced in "D" or T with a group R which is other than methyl. Finally, the symbol "Q" denotes a quadrifunctional unit $SiO_{4/2}$, where all four of the available bonds from the silicone atom are used for binding to oxygen for the formation of the polymeric chain.

The number of different silicones which can be manufactured is staggering. It would be clear to one skilled in the art that the properties of each of the silicones will vary depending on the type of monomer, the type of substitution, the size of the polymeric chain, and the degree of cross linking or size of the side chain. Different properties are attained depending on whether the backbone is a silicone chain with carbon-based side chains or whether the backbone is carbon-based with silicone side chains.

As described above, the at least one film-forming silicone resin may, in one embodiment, be chosen from siloxysilicates and silsesquioxanes. Any siloxysilicates or silsesquioxanes that functions as a film-former is within the practice of the invention. In one embodiment, the at least one film-forming silicone resin is chosen from substituted siloxysilicates and silsesquioxanes. A substituted siloxysilicate or a substituted silsesquioxane may be, for example, a siloxysilicate or a silsesquioxane where a methyl group has been substituted with a longer carbon chain such as an ethane, propane, or butane chain. The carbon chain may be saturated or unsaturated.

In one embodiment, the at least one film-forming silicone resin is chosen from siloxysilicates such as trimethylsiloxy-silicates, which are represented by the following formula: $[(CH_3)_3—Si—O]_x—(SiO_{4/2})_y$ (MQ units), where x and y can have values ranging from 50 to 80. In a further embodiment, a siloxysilicate may be chosen from any combination of M and Q units, such as, for example, $[(R)_3—Si—O]_x—(SiO_{4/2})_y$, where R is chosen from methyl groups and longer carbon chains.

In a further embodiment, the film-forming silicone resin is chosen from silsesquioxanes that are represented by the following formula: $(CH_3SiO_{3/2})_x$ (T units), where x has a value of up to several thousand and the $CH_3$ may be replaced by an R, as described above for T units. In one embodiment, the silsesquioxane is chosen from polymethylsilsesquioxanes, which are silsesquioxanes that do not have a substituent replacing the methyl group. The polymethylsilsesquioxanes useful in the present invention are film-formers and can, for example, have about 500 or less T units, such as, for example, from about 50 to about 500 T units.

In one embodiment of the invention, the film forming silicone resins have a melting point ranging from about 40° C. to about 80° C. These silicone resins are soluble or dispersible in volatile silicones or other organic liquids. In one embodiment, the at least one film-forming silicone resins may be solid at about 25° C. In one embodiment, the at least one film-forming silicone resins may have a molecular weight ranging from 1000 to 10,000 grams/mole. In one embodiment, the at least one film-forming silicone resin is present in the composition in an amount ranging from 0.5% to 20% by weight, relative to the total weight of the composition, such as, for example, ranging from 1% to 10%.

Not all polymethylsilsesquioxanes are film-formers. For example, the highly polymerized polymethylsilsesquioxanes (T Resins), such as Tospearl™ from Toshiba or KMP590 from Shin-Etsu are highly insoluble, and therefore are not effective film-formers. The molecular weight of these polymethylsilsesquioxanes is difficult to determine, and they generally contain a thousand or more T units.

An example of a polymethylsilsesquioxane useful in accordance with the present invention is Belsil PMS MK, also referred to as Resin MK, available from Wacker Chemie. This polymethylsilsesquioxane is a polymer primarily formed of polymerized repeating units of $CH_3SiO_{3/2}$ (T units), and which can also contain up to about 1% (by weight or by mole) of $(CH_3)_2SiO_{2/2}$ (D units). It is believed that the polymers are in a "cage" and "ladder" configuration, as exemplified in the figure below. The weight-average molecular weight of the "cage" unit has been calculated to be 536. The majority of the polymer is in the "ladder" configuration, where the ends are capped with ethoxy ($CH_3CH_2O$) groups. The weight percent of ethoxy present is about 4.5%, and the mole percent is about 7% (silicone units). Since this functionality can react with water, a small and variable amount of SiOH can also be present. The weight-average molecular weight can be, for example, from about 500 to about 50,000, such as about 10,000.

Polymethylsilsesquioxanes suitable for use in the present invention also include KR-220L available from SHIN-ETSU. The structure of KR-220L is made up of mostly silicone T-units ($CH_3SiO_{3/2}$), with Si—OH or silanol end units. There are no D units. Other polymethylsilsesquioxanes that can be useful in the practice of the invention include KR-242A, which has a structure of about 98% methyl T units and about 2% dimethyl D units, with Si—OH or silanol end units, and KR-251, which has a structure of about 88% methyl T units and about 12% dimethyl D units, with Si—OH or silanol end units, both of which are available from SHIN-ETSU.

In one embodiment of the invention, the at least one film-forming silicone resin is chosen from combinations of M, D, T, and Q units comprising at least two units chosen from M, D, T, and Q, which satisfy the relationship $R_nSiO_{(4-n)/2}$ wherein n is a value ranging from 1.0 to 1.50. Some resins of this type are disclosed in U.S. Pat. No. 6,074,654. R may be a methyl group or any carbon chain as long as the silicone resin retains its film-forming properties. Up to 5% of silanol or alkoxy functionality may also be present in the resin structure as a result of processing.

In a further embodiment, the at least one film-forming silicone resin comprises repeating M units and Q units. The ratio of M units to Q units may be, for example, about 0.7:1. The at least one film-forming silicone resin may be chosen, for example, from Wacker 803 and 804, available from Wacker Silicones Corporation and G.E. 1170-002 from General Electric.

In a further embodiment, the at least one film-forming silicone resin is a copolymer, wherein at least one unit of the copolymer is chosen from M, D, T, and Q silicone units, and wherein at least one additional unit of the copolymer is chosen from an ester. The at least one film-forming silicone resin may be chosen from, for example, diisostearoyl trimethylolpropane siloxysilicates, such as SF 1318, available from GE Silicones.

The compositions according to the present invention can additionally comprise at least one additional film-former. The at least one additional film-former may improve, for example, smoothness or spreadability, water-resistance, transfer resistance properties, or other cosmetic or pharmaceutical properties desired by one of skill in the art. The at least one additional film former may be chosen from, for example, polyethylene, vinylpyrrolidone/vinyl acetate (PVP/VA) copolymers such as the Luviskol® VA grades (all ranges) from BASF® Corporation and the PVP/VA series from ISP, acrylic fluorinated emulsion film formers including Foraperle® film formers such as Foraperle® 303 D from Elf Atochem (although Foraperle® may not be appropriate for some cosmetic formulations) GANEX® copolymers such as butylated PVP, PVP/Hexadecene copolymer, PVP/Eicosene copolymer or tricontanyl, Poly(vinylpyrrolidone/diethylaminoethyl methacrylate) or PVP/Dimethylaminoethylmethacrylate copolymers such as Copolymer 845, Resin ACO-5014 (Imidized IB/MA copolymer), other PVP based polymers and copolymers, alkyl cycloalkylacrylate copolymers (See, e.g., WO 98/42298), Mexomere® film formers and other allyl stearate/vinyl acetate copolymers (allyl stearate/VA copolymers), polyolprepolymers such as PPG-12/SMDI copolymer, polyolprepolymers such as PPG-1 2/SM DI copolymer, Poly(oxy-1,2-ethanediyl), α-hydro-ω-hydroxy-polymer with 1,1'-methylene-bis-(4-isocyanatocyclohexane) available from Bamet, Avalure™ AC Polymers (Acrylates Copolymer) and Avalure™ UR polymers (Polyurethane Dispersions), available from B.F. Goodrich.

The at least one additional film former which also may be used within the framework of the invention includes film formers having any film former chemistry known in the art such as, for example, PVP, acrylates, urethane, synthetic polymers of the polycondensate type, free-radical type, or ionic type, polymers of natural origin, and mixtures thereof, as well as any other film former known within the practice of the cosmetic and pharmaceutical arts which one skilled in the art may determine to be compatible.

An appropriate amount of the at least one additional film-former may be determined by one of skill in the art, and can vary considerably based on the application. For example, in one embodiment, the at least one additional film-former may be used in an amount ranging from 0.1% to 20%, such as, for example, ranging from 1% to 10%, by weight, relative to the total weight of the composition.

The amounts of the at least one film-forming silicone resin and of the at least one structuring polymer, e.g., a polyamide polymer, may be chosen according to the desired hardness and desired stability of the compositions, and according to the specific application envisaged. The respective amounts of the at least one structuring polymer, e.g., a polyamide polymer, and of the at least one film-forming silicone resin can be such that a disintegrable solid which does not flow under its own weight is obtained.

In one aspect, the present invention provides a composition comprising, in a physiologically acceptable medium, fibers and ETPEA, the composition being intended in particular for cosmetics. The invention also relates to a cosmetic make-up or care process for keratin materials using the fiber-containing composition. The make-up or care process and composition according to the invention are intended more particularly for the keratin materials of human beings, such as the skin (including the scalp), the nails, keratin fibers, especially substantially long linear keratin fibers, such as the eyelashes, the eyebrows and the hair. In one aspect, the present invention provides a mascara with ETPEA and fibers.

The composition according to the invention can be in the form of a coating composition for the eyelashes (in particular a mascara), an eyeliner, a product for the eyebrows, a product for the lips, a face powder, an eyeshadow, a foundation, a make-up product for the body, a concealer product, a nail varnish, a skincare product, including a product for scalp care, or a hair care product (hair mascara or spray).

It is known practice to use fibers in make-up products, especially for their lengthening effects in mascaras (see JP-A-57/158 714 and JP-A-3-153 613), their moisturizing properties in lipsticks (see document U.S. Pat. No. 5,498,407), to improve the contours of lipstick on the edges of the lips (see document EP-A-0 106 762) or to improve the condition of broken nails (see FR-A-1 529 329) or in skincare products for their velvety feel (see JP-A-7/196 440). The present invention utilizes these fibers in combination with ETPEA to form a cosmetic. In one aspect, the ETPEA is present in the composition according to the invention in a content ranging from 0.01% to 10% by weight, relative to the total weight of the composition, preferably ranging from 0.05% to 5% by weight and better still ranging from 0.1% to 3% by weight.

According to the invention, the composition contains one or more fibers. The term "fiber" means any particle that is solid at room temperature and atmospheric pressure, whose length is greater than its apparent diameter, used alone or in combination, and which is insoluble in the ingredients of the composition, even when these ingredients are raised to a temperature above room temperature and in particular to their softening point or their melting point. These fibers are advantageously chemically inert, i.e., they do not react chemically with the various ingredients of the composition. These fibers have melting points that are at least greater than 170° C. and better still greater than 200° C. They may be absorbent or non-absorbent, i.e., capable in particular of absorbing the oils of the composition and also the biological substances secreted by the skin.

The fibers that can be used in the composition of the invention may be fibers of synthetic or natural, and inorganic or organic origin. They may be short or long, flat, cylindrical or lamellar, individual or organized, for example in bundles, and hollow or solid. They can have any shape, and in particular a circular, elliptic or polygonal (triangular, square, hexagonal or octagonal) cross section depending on the specific application envisaged. In particular they can have blunt and/or rounded ends to prevent injury. Their ends may also be multilobal, in particular trilobal, pointed or rounded. In particular, the fibers have a length ranging from 1 nm to 20 mm, preferably from 10 nm to 5 mm and better still from 0.1 mm to 1.6 mm. Their cross section can be within a circle of diameter D ranging from 2 nm to 150 µm, preferably ranging from 20 nm to 120 µm and better still from 500 nm to 80 µm. The weight or yarn count of the fibers is often given in denier or decitex and represents the weight in grams per 9 km of yarn. The fibers in the composition according to the invention preferably have a yarn count chosen in the range from 0.15 to 30 denier and better still from 0.18 to 18 denier. Advantageously, the fibers have a length L and a diameter D such that L/D is chosen in the range from 1.5 to 2 500, preferably from 3.5 to 500 and better still from 5 to 150.

The fibers can be those used in the manufacture of textiles, and in particular silk, cotton, wool or flax fibers, cellulose fibers extracted in particular from wood, plants or algae, polyamide (Nylon®), cork, sugar cane, rayon or viscose fibers, acetate fibers, in particular rayon acetate or cellulose acetate fibers, poly-(p-phenylene terephthalimide) (or aramide) fibers, in particular Kevlar® fibers, acrylic polymer fibers, in particular polymethyl methacrylate (PMMA) or poly-2-hydroxyethyl methacrylate fibers, polyolefin fibers and in particular polyethylene or polypropylene fibers, glass, silica or carbon fibers, in particular in graphite form, polytetrafluoroethylene (Teflon®), insoluble collagen, polyester, polyvinyl chloride or polyvinylidene chloride, polyvinyl alcohol, polyacrylonitrile, chitosan, polyurethane or polyethylene phthalate fibers, fibers formed from a mixture of polymers such as those mentioned above, for instance polyamide/polyester fibers, and mixtures thereof.

It is also possible to use surgical fibers, such as resorbable synthetic fibers prepared from glycolic acid and from ε-caprolactone ("Monocryl" from Johnson & Johnson), resorbable synthetic fibers such as the copolymer of lactic acid and of glycolic acid ("Vicryl" from Johnson & Johnson), terephthalic polyester fibers ("Ethibond" from Johnson & Johnson) and stainless steel threads ("Steel" from Johnson & Johnson) in particular for use as nail varnishes.

Moreover, the fibers may or may not be surface-treated and may or may not be coated, in particular with a view to making them hydrophobic. As coated fibers which can be used in the invention, mention may be made of polyamide fibers coated with copper sulfide for an antistatic effect (for example the R-STAT fibers from Rhodia) or another polymer allowing a particular organization of the fibers (specific surface treatment) or a surface treatment which induces color/hologram effects ("Lurex" fiber from Sildorex, for example).

Flat multilayer fibers having goniochromatic properties may also be used. Such fibers are disclosed in particular in the document. Multilayer polymer fibers are disclosed in particular in document EP-A-0 921 217. They are formed from alternating layers of polyamide The fibers which can be used in the composition according to the invention are preferably polyamide or poly-(p-phenylene terephthalimide) fibers for a first polymer with a polyamide unit. Their length (L) can range from 0.1 to 5 mm, preferably from 0.25 to 1.6 mm, and their average diameter (D) can range from 5 to 50 µm. In particular, the polyamide fibers sold by Etablissements P. Bonte under the name Polyamide 0.9 Dtex 3 mm, having an average diameter ranging from 15 µm to 20 µm, a weight of about (0.9 dtex) and a length ranging from 0.3 mm to 1.5 mm, can be used. Poly-(p-phenylene terephthalamide) fibers with an average diameter of 12 µm and a length of about 1.5 mm can also be used, such as those sold under the name Kevlar Floc by the company Du Font Fibers.

The fibers may be present in the composition according to the invention in a content ranging from 0.1% to 40% by weight, relative to the total weight of the composition, in particular ranging from 0.5% to 30% by weight, preferably ranging from 1% to 20% by weight and better still from 1% to 10% by weight. Advantageously, the first polymer and the fibers may be present in the composition according to the invention in a fibers/first polymer weight ratio which may range from 0.5 to 4, preferably ranging from 0.9 to 2.5.

In one aspect, the cosmetic composition of the present invention includes ETPEA and a gelling agent, i.e., an agent with gelling ability that is not ETPEA. This at least one gelling agent is chosen from liposoluble and lipodispersible rheological agents, such as agents that are soluble or dispersible in the fatty phase that is liquid at room temperature and atmospheric pressure. The at least one gelling agent may be chosen from gelling agents in polymeric form and gelling agents in mineral form. In one embodiment, the at least one gelling agent may be in mineral form with particle sizes that cause little or no light scattering. Thus, it may be possible to obtain a translucent or even transparent composition. In one embodiment, the at least one gelling agent is not soluble in an aqueous phase or in water.

Fatty-phase gelling agents or rheological agents which can be used in the invention may be chosen from lipodispersible mineral particles such as optionally modified clays and optionally modified silica, for example which have been hydrophobic-treated, as well as polymeric gelling agents such as partially or totally crosslinked elastomeric polyorganosiloxanes of three-dimensional structure; galactomannans comprising from 1 to 6 hydroxyl groups, for example 2 to 4 hydroxyl groups, per saccharide, substituted with a saturated or unsaturated alkyl chain; polymers or copolymers resulting from the polymerization or copolymerization of an ethylenic monomer, comprising one or more ethylenic, preferably conjugated bonds (or dienes); silicone gums; ethylcellulose, such as the products sold under the name Ethocel by Dow Chemical; and mixtures thereof.

As modified clays which can be used, mention may be made of hectorites modified with an ammonium chloride of a $C_{10}$ to $C_{22}$ fatty acid, such as hectorite modified with distearyidimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearylalkylonium bentonites, such as the products sold or made under the names Claytone APA and Claytone AF by the company Southern Clay, and Baragel 24 sold or made by the company Rheox.

As polyorganosiloxanes which can be used in the invention, mention may be made of the crosslinked elastomeric polyorganosiloxanes described in application EP-A-0,295,886, the disclosure of which is incorporated herein by reference. According to that application, they are obtained by addition reaction and crosslinking, in the presence of a platinum-type catalyst, of at least:

(a) a polyorganosiloxane having at least two $C_2$ to $C_6$ lower alkenyl groups per molecule; and (b) a polyorganosiloxane having at least two hydrogen atoms linked to a silicon atom per molecule. It is also possible to use the polyorganosiloxanes described in U.S. Pat. No. 5,266,321, the disclosure of which is incorporated by reference herein. According to that patent, they are chosen in particular from:

i) polyorganosiloxanes comprising $R_2SiO$ and $RSiO_{1.5}$ units and optionally $R_3SiO_{0.5}$ and/or $SiO_2$ units in which the radicals R, independently of each other, are chosen from a hydrogen, an alkyl such as methyl, ethyl or propyl, an aryl such as phenyl or tolyl, an unsaturated aliphatic group such as vinyl, the weight ratio of the units $R_2SiO$ to the units $RsiO_{1.5}$ ranging from 1/1 to 30/1;

ii) polyorganosiloxanes which are insoluble and swellable in silicone oil, obtained by addition of an polyorganohydrogenosiloxane (1) and of a polyorganosiloxane (2) having unsaturated aliphatic groups such that the amount of hydrogen or of unsaturated aliphatic groups in (1) and (2) respectively ranges from 1 to 20 mol % when the polyorganosiloxane is non-cyclic and from 1 to 50 mol % when the polyorganosiloxane is cyclic. Optionally, these polyorganosiloxanes can comprise from 1 to 40 oxyalkylene groups, such as oxypropylene and/or oxyethylene groups.

As examples of polyorganosiloxanes which can be used according to the invention, mention may be made of those sold or made under the names KSG6 from Shin-Etsu, Trefil E-505C or Trefil E-506C from Dow-Corning, Gransil from Grant Industries (SR-CYC, SR DMF10, SR-DC556) or those marketed in the form of preconstituted gels (KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric. A mixture of these commercial products may also be used.

As alkyl galactomannans which can be used in the invention, mention may be made of guar gum or carob gum alkylated with $C_1$ to $C_{-6}$, for example, $C_1$ to $C_3$ alkyl chains, such as ethyl or propyl guar having a degree of substitution of 2 to 3, for example, of about 2.5 to 2.8, as described in document EP-A-708 114 and sold or made by the company Aqualon under the name N-Hance-AG 200® or N-Hance AG 50®.

As polymers or copolymers resulting from the polymerization or copolymerization of an ethylenic monomer, use may be made of vinyl, acrylic or methacrylic copolymers which may be block copolymers, such as diblock or triblock copolymers, or even multiblock or starburst or radial copolymers. The at least one ethylenic gelling agent may comprise, for example, a styrene block (S), an alkylstyrene block (AS), an ethylene/butylene block (EB), an ethylene/propylene block (EP), a butadiene block (B), an isoprene block (I), an acrylate block (A), a methacrylate block (MA) or a combination of these blocks.

In one embodiment, a copolymer comprising at least one styrene block is used as gelling agent or ethylenic rheological agent. A triblock copolymer and in particular those of the polystyrene/polyisoprene or polystyrene/polybutadiene type, such as those sold or made under the name "Luvitol HSB" by BASF and those of the polystyrene/copoly(ethylene-propylene) type or alternatively of the polystyrene/copoly(ethylene/butylene) type, such as those sold or made under the brand name "Kraton" by Shell Chemical Co. or Gelled Permethyl 99A by Penreco, may be used. Styrene-methacrylate copolymers can also be used.

As an ethylenical rheological agent which can be used in the composition of the invention, mention may be made, for example, of Kraton (G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton G1750X (EP) multiarm, Kraton G1765X (EP) multiarm, Kraton D-1101 (SBS), Kraton D-1102 (SBS), Kraton D-1107 (SIS), Gelled Permethyl 99A-750, Gelled Permethyl 99A-753-58 (mixture of starburst block polymer and triblock polymer), Gelled Permethyl 99A-753-59 (mixture of starburst block polymer and triblock polymer), Versagel 5970 and Versagel 5960 from Penreco (mixture of starburst polymer and triblock polymer in isododecane), and OS 129880, OS 129881 and OS 84383 from Lubrizol (styrene-methacrylate copolymer).

As other rheological agents which can be used in the invention, mention may be made of silicone gums. The silicone gum has organic groups ($R_7$, $R_8$, $R_9$, $R_{10}$, $R_{11}$, and $R_{12}$) attached to the silicon atoms, the silicon atoms being separated by oxygen atoms (i.e., X—Si($R_7$)($R_8$)—O—Si($R_9$)($R_{10}$)—O—Si($R_{11}$)($R_{12}$)—X. In general, $R_7$, $R_8$, $R_{11}$, and $R_{12}$ are identical or different, and each is chosen from alkyl radicals comprising from 1 to 6 carbon atoms; $R_9$ and $R_{10}$ are identical or different, and each is chosen from alkyl radicals comprising from 1 to 6 carbon atoms and aryl radicals and X is chosen from alkyl radicals comprising from 1 to 6 carbon atoms, a hydroxyl radical and a vinyl radical. The number of Si(R)(R) units are chosen so as to give the silicone gum a viscosity of greater than 100 000 mPa·s, such as greater than 500 000 mPa·s. In general, the silicon gum has about 3,000 to 8,000 silicon atoms. Suitable silicon gums include the product sold or made under the name SE30 by the company General Electric; the product sold or made under the name AK 500 000 by the company Wacker; the product sold or made under the name Q2-1401 by the company Dow Corning; the product sold or made under the name Q2-1403 by the company Dow Corning, and the product sold or made under the name 761 by the company Rhone-Poulenc (Rhodia Chimie).

As other gelling agents or rheological agents which can be used in the invention, mention may be made of silica, such as fumed silica. The fumed silica may have a particle size which may be nanometric to micrometric, for example ranging from about 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas which have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be:

trimethylsiloxyl groups, which are obtained in particular by treating fumed silica in the presence of hexamethyldisilazane. Silicas thus treated are known as "silica silylate" according to the CTFA (6th edition, 1995). They are sold or made, for example, under the references "Aerosil R812®" by the company Degussa and "CAB-O-SIL TS-530®" by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot;

groups derived from reacting fumed silica with silane alkoxides or siloxanes. These treated silicas are, for example, the products sold or made under the reference "Aerosil R805®" by the company Degussa.

According to the invention, a hydrophobic silica, such as a fumed silica, may be used as lipophilic gelling agent or rheological agent. The use of fumed silica makes it possible to obtain a translucent or even transparent composition, in particular in the form of a stick which does not exude, in the absence of opacifying particles such as waxes, fillers and pigments (including nacres).

The at least one liposoluble rheological agent can allow the exudation of the composition to be limited and can allow its stability to be increased, while at the same time conserving the composition's glossy appearance, which is not possible with waxes such as those used conventionally in cosmetics and dermatology. These gelling agents can be used, for example, at concentrations of from 0.05% to 35% relative to the total weight of the composition, for example from 0.5% to 20% or from 1% to 10%.

The gels of the invention may be formulated into personal care products according to techniques well known in the art. The gel may be combined with ingredients conventionally incorporated into personal care products such as chelating agents, colorants, emulsifiers, fillers, hardeners, perfumes, strengtheners, water and wax, to name a few. Such additives are well known in the art, and are also set forth in, e.g., the following documents, all incorporated by reference herein in their entirety: U.S. Pat. No. 3,255,082 to Barton, U.S. Pat. No. 4,049,792 to Elsnau, U.S. Pat. No. 4,137,306 to Rubino et al., and U.S. Pat. No. 4,279,658 to Hooper et al. See also U.S. Pat. Nos. 3,148,125 and 5,538,718 (describing the formulation of lipstick and other cosmetic sticks). See also European Patent Application Nos. 1 068 855 A1 and 1 068 856 A1, where the disclosure of these two documents is incorporated herein by reference, where these documents provide additional formulation suggestions for incorporating an organic gellant into a cosmetic or other personal care product, where these formulation suggestions may be employed to formulate a corresponding product with the ETPEA gellant of the present invention in place of some or all of the gallants, e.g., the UNICLEAR™ 80 and 100 gellants, disclosed therein.

Personal care products may be prepared from the ETPEA resin of the invention by mixing the various components of the product at an elevated temperature and then cooling in order to form the gelled (solidified) composition. Desirably, any volatile components are added to the mixture at a relatively late stage of the mixing, so as to limit volatilization of the component. Preferably, the liquid and ETPEA gelling agent are mixed and heated so as to fully dissolve the ETPEA in the liquid (e.g., at 80° C.-150° C.). An active ingredient (e.g., active antiperspirant) can be added after the ETPEA fully dissolves, and mixing then takes place. Mixing may continue during cooling, with colorant or other component being added during the cooling stage.

Thus, the present invention provides a personal care product comprising a resin composition prepared by reacting components comprising dibasic acid, diamine, polyol and monoalcohol, wherein at least 50 equivalent percent of the dibasic acid comprises polymerized fatty acid; and at least 50 equivalent percent of the diamine is ethylene diamine. The personal care product preferably further comprises at least one cosmetically active ingredient and/or at least one dermatologically active ingredient. The personal care product may constitute a composition for the care and/or treatment and/or making-up of keratinous substances. Suitable compositions include makeup products for the lips such as lipstick and lip pencils, and also for the care and/or treatment of the skin, including the scalp and lips, such as care creams applied daily, sunscreen for the lips and skin, makeup products for the skin, body hygiene products such as deodorants in particular as sticks, and to eye makeup products such as eye liners, in particular in the form of a pencil or mascaras, notably in the form of a cake.

In addition, the present invention provides a controlled release composition comprising a volatile component and a resin composition prepared by reacting components comprising dibasic acid, diamine, polyol and monoalcohol, wherein at least 50 equivalent percent of the dibasic acid is or comprises polymerized fatty acid; and at least 50 equivalent percent of the diamine is ethylene diamine.

Further, the ETPEA resins of the present invention may be combined with a suitable solvent so as to form a gel, where the gel in combination with a wick forms a candle. Thus, in one aspect, the present invention provides a candle comprising a wick and a resin composition prepared by reacting components comprising dibasic acid, diamine, polyol and monoalcohol, wherein (a) at least 50 equivalent percent of the dibasic acid comprises polymerized fatty acid; (b) at least 50 equivalent percent of the diamine comprises ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol; the candle further comprising a solvent that is gelled by the resin. In one aspect, the candle contains icons. An exemplary icon is a second gelled phase, preferably visually distinct from the gel formed from ETPEA. The icon(s) may be embedded within the candle, or may be on the surface of the candle. The second gelled phase may be, but need not be, ETPEA. In one aspect, the second gelled phase is transparent.

The candle may, in one aspect, contain hydrocarbon, where the hydrocarbon and the ETPEA resin form a gel. The candle may also, in one aspect, contain a fragrance material. Furthermore, the candle may contain an ester.

Methods of using gels to form candles, including wicks, icons, the use of hydrocarbons, suitable fragrance materials, and suitable esters, are well known in the candle-making art, where these methods and components may be used to prepare candles from EPTEA resins.

Again, in regard to the preparation of, and components used in, candles, personal care products, and fragrance-releasing compositions, reference is made U.S. Pat. Nos. 3,615,289, 3,645,705, 6,111,055, 6,129,771 and 6,214,063 (describing the formulation of candles and pigmented objects embedded in candle, which are an example of an "icon"); U.S. Pat. Nos. 3,148,125 and 5,538,718 (describing the formulation of lipstick and other cosmetic sticks); and U.S. Pat. Nos. 4,275,054, 4,937,069, 5,069,897, 5,102,656 and 5,500,209 (describing the formulation of deodorant and/or antiperspirant).

The following examples are set forth as a means of illustrating the present invention and are not to be construed as a limitation thereon.

Methodology

The hardness of a composition may be measured according to a method of penetrating a probe into said composition and in particular using a texture analyzer (for example TA-XT2 from Rheo) equipped with an ebonite cylinder of height 25 mm and diameter 8 mm. The hardness measurement is carried out at 20° C. at the center of 5 samples of said composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is about ±50 g.

Hardness may also be measured by a "cheese wire" method, which involves cutting an 8.1 mm tube of composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may range from 30 g to 150 g, such as from 30 g to 120 g, and further such as from 30 g to 50 g.

The hardness of the composition of the present invention may be such that the compositions are self-supporting and can easily disintegrate to form a satisfactory deposit on a keratinous material. In addition, this hardness may impart good impact strength to the inventive compositions which may be cast in stick form.

Turbidity may be measured using a model 2100 P turbidimeter from Hach at ambient temperature (20 to 25° C.). The tubes used for the measurement are referenced AR 397 A cat 24347-06. The device is calibrated using formazine suspensions with different concentrations. The turbidity is measured in terms of Nephelometric Turbidity Units (NTU).

EXAMPLES

Example A

The following reactants and relative reactant amounts were used to prepare an ETPEA resin:

| Reactant | Equivalents | Weight Percent |
| --- | --- | --- |
| PRIPOL ™ 1015 dimer acid | 100 | 76.7 |
| Stearyl alcohol | 28 | 17.3 |
| Neopentyl glycol | 16 | 2.0 |
| Ethylenediamine | 56 | 4.0 |

The ETPEA was synthesized by charging the PRIPOL™ 1015 dimer acid, steraryl alcohol and neopentyl glycol to a reaction vessel at room temperature, heating the mixture to 100° C., adding the ethylenediamine, heating to 220° C. and holding for 3 hours, and holding under vacuum (8-10 mbar) at 220° C. for 2 hours. The ETPEA had a softening point of 76.7° C. and a color of 596 (APHA).

Example B

The following reactants and relative reactant amounts were used to prepare an ETPEA resin:

| Reactant | Equivalents | Weight Percent |
| --- | --- | --- |
| EMPOL ™ 1008 dimer acid | 100 | 75.8 |
| Stearyl alcohol | 25 | 17.1 |
| Neopentyl glycol | 25 | 3.3 |
| Ethylenediamine | 50 | 3.8 |

The ETPEA was synthesized following the procedure described in Example A, using the relative reactant amounts set forth in the above Table. The product ETPEA has a softening point of 74.7° C. and a color of 238 (APHA).

The following Examples 1-74, which are prophetic, illustrate the incorporation of ETPEA of either of Examples A or B into a personal care product. The following suppliers, provide components that may be included in compositions of the present invention: SCHERCEMOL™ DISM diisostearyl malate may be obtained from Shear Chemical Inc. CERAPHYL™ 45 dioctyl malate may be obtained from ISP. CRISTAL™ O castor oil and Nature Chem PGR propylene glycol ricinoleate may be obtained from Chaschem. PARSOL™ 1789 butyl methoxydibenzoyl methane may be obtained from Givaudan-Roure. Neo Heliopan 303 octylcrylene may be obtained from Haarman & Reimer. ETHOCEL™ ethyl cellulose may be obtained from Dow Chemical. The specific Examples 1-74 also identify various suppliers from which components for personal care products may be obtained.

Example 1

Lip Composition Formulation

ETPEA is solubilized with the aid of a polyglyceryl-2 polyhydroxystearate in parleam oil, at 100° C., followed by addition of pigments. The whole is mixed using a deflocculating turbomixer (Rayneri) and then cast in lipstick molds. A homogeneous stick of lipstick is obtained, where the hardness thereof may be measured using a TA-XT2 texture analyzer at 20° C. In one aspect the lipstick is glossy and non-migrating, as may be confirmed by a test with a panel of experts. In one aspect, the lipstick of the present invention is glossier when applied than a lipstick of the prior art, and migrates less after being worn for 2 hours. Percents (by weight) of the components of the composition reaction mixture are indicated in Table 1.

TABLE 1

| Component | Weight percent |
| --- | --- |
| ETPEA | 25.0 |
| Parleam oil | 56.0 |
| Polyglyceryl-2 polyhydroxystearate | 10.0 |
| Pigments (brown iron oxide + titanium oxide) | 9.0 |

Example 2

Anhydrous Eyeshadow

An eyeshadow in stick form is prepared as in Example 1. In one aspect the eyeshadow is glossy and non-migrating. Percents (by weight) of the components of the composition reaction mixture are indicated in Table 2.

TABLE 2

| Component | Weight percent |
| --- | --- |
| ETPEA | 25.0 |
| Parleam oil | 35.1 |
| Glyceryl oleate | 31.25 |
| Pigments | 8.65 |

Example 3

Mascara

In one aspect, the present invention provides a composition in the form of a mascara. Percents (by weight) of the components of the composition reaction mixture are indicated in Table 3.

TABLE 3

| Component | Weight percent |
| --- | --- |
| ETPEA | 1.0 |
| Carnauba wax | 2.6 |
| Beeswax | 3.3 |
| Paraffin wax | 10.4 |
| Hydrogenated jojoba oil | 0.2 |
| Hydrogenated palm oil | 0.2 |
| 2-Amino-2-methyl-1,3-propanediol | 0.8 |
| Triethanolamine | 2.4 |
| Stearic acid | 6.6 |
| Hydroxyethylcellulose | 0.8 |
| Gum arabic | 0.6 |

TABLE 3-continued

| Component | Weight percent |
| --- | --- |
| Ethyl acrylate/methyl methacrylate copolymer (80/20) as an aqueous dispersion containing 50% AM (Daitosol 5000 AD from Saito) | 7.0 AM |
| Black iron oxide | 5.0 |
| Preserving agents | q.s. |
| Water | q.s. 100.0 |

Example 4

Mascara

In one aspect, the present invention provides a composition in the form of a mascara. Percents (by weight) of the components of the composition reaction mixture are indicated in Table 4.

TABLE 4

| Component | Weight percent |
| --- | --- |
| ETPEA | 1.0 |
| Carnauba wax | 4.6 |
| Rice bran wax | 2.1 |
| Paraffin | 2.2 |
| Beeswax | 8.2 |
| Talc | 1.0 |
| Bentonite | 5.0 |
| Vinyl acetate/allyl stearate copolymer (65/35) (Mexomer PQ from Chimex) | 6.5 |
| Polyvinyl laurate (Mexomere PP from Chimex) | 0.7 |
| Sulphopolyester (AQ 55S from Eastman Chemical) | 0.12 |
| Isododecane | 53.9 |
| Propylene carbonate | 1.6 |
| Pigments | 4.9 |
| Preserving agents | q.s. |
| Water | q.s. 100.0 |

Example 5

Mascara a) In one aspect of the present invention, a dispersion of non-crosslinked copolymer of methyl acrylate and of acrylic acid in a 95/5 ratio, in isododecane, is prepared according to the method of Example 7 of document EP-A-749 747. A dispersion is thus obtained of particles of poly(methyl acrylate/acrylic acid) surface-stabilized in isododecane with a polystyrene/copoly-(ethylene-propylene) diblock block copolymer sold under the name Kraton G1701 (Shell), with a solids content of 24.2% by weight, a mean particle size of 180 nm and a Tg of 20° C. This copolymer can form a film at room temperature.

b) In another aspect, the present invention provides for a composition in the form of a mascara. Percents (by weight) of the components of the composition reaction mixture are indicated in Table 5.

TABLE 5

| Component | Weight percent |
| --- | --- |
| ETPEA | 0.5 |
| Carnauba wax | 4.7 |
| Rice bran wax | 2.1 |

TABLE 5-continued

| Component | Weight percent |
| --- | --- |
| Paraffin | 2.2 |
| Beeswax | 8.2 |
| Talc | 1.0 |
| Bentonite | 5.0 |
| Vinyl acetate/allyl stearate copolymer (65/35) (Mexomer PQ from Chimex) | 6.5 |
| Polyvinyl laurate (Mexomere PP from Chimex) | 0.7 |
| Dispersion of polymer in isododecane according to a) | 10.0 |
| Propylene carbonate | 1.6 |
| Pigments | 4.9 |
| Preserving agents | q.s. |
| Isododecane | q.s. 100.0 |

Example 6

Lip Balm

In one aspect, the present invention provides a composition in the form of a colored transparent lip balm, prepared, for example, in the following manner. A dispersion of pigments is prepared in the presence of dispersing agent. This dispersion is combined with a mixture of ETPEA and octyldodecanol heated to ca. 100° C., while maintaining the mixture under slow stirring over ca. 30 minutes. After casting in molds and cooling to ambient temperatures, a solid composition is obtained. The turbidity of the composition may be measured as described herein, to provide a turbidity value in units of NTU. Percents (by weight) of the components of the composition reaction mixture are indicated in Table 6.

TABLE 6

| Component | Weight percent |
| --- | --- |
| ETPEA | 25.0 |
| Octyldodecanol | 10.0 |
| Iron oxides | 0.0006 |
| SOLSPERSE ® 21000* | 0.00002 |
| Fragrance | 4.0 |
| Parleam oil | q.s. 100.0 |

*Dispersing agent sold by Avecia Pigments and Additifs.

Example 7

Scenting Gel

In one aspect, the present invention provides a composition in the form of a colored transparent anhydrous scenting gel for the body, prepared by mixing the ingredients as indicated in Table 7. The turbidity of the gel may be measured as described herein, in terms of NTU.

TABLE 7

| Component | Weight percent |
| --- | --- |
| ETPEA | 43.0 |
| Pentacyclodimethicone | 43.0 |
| Aluminum lake of brilliant blue FCF on alumina (12/88) (Blue 1 lake) | 0.001 |
| SOLSPERSE ® 21000* | 0.000025 |
| Fragrance | 4.0 |
| Parleam oil | q.s. 100.0 |

*Dispersing agent sold by Avecia Pigments and Additifs.

Example 8

Mascara

In one aspect, the present invention provides a composition in the form of a mascara, prepared by mixing the ingredients as indicated in Table 8. In a preferred aspect, the mascara obtained is easy to apply and adheres well to the eyelashes during and after application, giving the eyelashes a lengthened effect upon application.

TABLE 8

| Component | Weight percent |
| --- | --- |
| ETPEA | 1.0 |
| Carnauba wax | 2.6 |
| Beeswax | 3.3 |
| Paraffin wax | 10.4 |
| Hydrogenated jojoba oil | 0.2 |
| Hydrogenated palm oil | 0.2 |
| 2-Amino-2-methyl-1,3-propanediol | 0.8 |
| Triethanolamine | 2.4 |
| Stearic acid | 6.6 |
| Hydroxyethylcellulose | 0.8 |
| Gum arabic | 0.6 |
| Ethyl acrylate/methyl methacrylate copolymer (80/20) as an aqueous dispersion containing 50% AM (Daitosol 5000 AD from Saito) | 5.0 AM |
| Polyamide fibers (3 mm long, 0.9 Dtex, from the company Paul Bonte) | 1.0 |
| Black iron oxide | 5.0 |
| Preserving agents | q.s. |
| Water | q.s. 100.0 |

Example 9

Mascara

In one aspect, the present invention provides a composition in the form of a mascara, prepared by mixing the ingredients as indicated in Table 9. In a preferred aspect, the mascara obtained adheres well to the eyelashes during application, and allows the eyelashes to be made up quickly.

TABLE 9

| Component | Weight percent |
| --- | --- |
| ETPEA | 1.0 |
| Carnauba wax | 2.6 |
| Beeswax | 3.3 |
| Paraffin wax | 10.4 |
| Hydrogenated jojoba oil | 0.2 |
| Hydrogenated palm oil | 0.2 |
| 2-Amino-2-methyl-1,3-propanediol | 0.8 |
| Triethanolamine | 2.4 |
| Stearic acid | 6.6 |
| Hydroxyethylcellulose | 0.8 |
| Gum arabic | 0.6 |
| Ethyl acrylate/methyl methacrylate copolymer (80/20) as an aqueous dispersion containing 50% AM (Daitosol 5000 AD from Saito) | 5.0 AM |
| Polyamide fibers (3 mm long, 0.9 Dtex, from the company Paul Bonte) | 1.0 |
| Black iron oxide | 5.0 |
| Preserving agents | q.s. |
| Water | q.s. 100.0 |

Example 10

Lipstick

In one aspect, the present invention provides a composition in the form of a lipstick, prepared, for example, in the following manner. Polyamide fibers are predispersed in an ETPEA/isoparaffin (Parleam) mixture using a spatula. In one aspect, the resulting paste is ground in a three-roll mill. A separate reaction vessel is charged with ETPEA, 2-octyldodecanol, Parleam, and pigments, and the charged components are mixed together with stirring, such as with a Raynerie turbomixer, at about 1000 rpm and about 100° C. The reaction vessel is then further charged with the fiber predispersion, and the resulting reaction mixture is stirred at about 800 rpm for about 30 minutes. The resulting preparation is then cast in a lipstick mold, and placed at about −20° C. for about 30 minutes, before being unmolded to yield the final lipstick product. Percents (by weight) of the components of the composition reaction mixture are indicated in Table 10.

TABLE 10

| Component | Weight percent |
| --- | --- |
| ETPEA | 25 |
| 2-Octyldodecanol | 10 |
| Pigments | 5 |
| Polyamide fiber (3 mm long, 0.9 Dtex) | 0 to 10 |
| Hydrogenated isoparaffin (Parleam) | q.s. 100 |

Example 11

Anhydrous Cast Foundations

In one aspect, the present invention provides a composition in the form of an anhydrous cast foundation, prepared, for example, in a manner similar to that of EXAMPLE 10, according to the weight percentage values indicated in Table 11. The presence of fiber reduces the extent to which the composition exudes oil at its surface. The isododecane contributes to the non-transfer properties of the composition.

TABLE 11

| Component | Weight percent |
| --- | --- |
| ETPEA | 25 |
| Isododecane | 15 |
| Pigments | 8 |
| Polyamide fiber (3 mm long, 0.9 Dtex) | 0 to 10 |
| Hydrogenated isoparaffin (Parleam) | q.s. 100 |

Example 12

Anhydrous Foundation

In one aspect, the present invention provides a composition in the form of an anhydrous foundation, prepared, for example, in a manner similar to that of EXAMPLE 10, according to the weight percentage values indicated in Table 12.

TABLE 12

| Component | Weight percent |
| --- | --- |
| ETPEA | 11 |
| Parleam | 10 |
| Pigments | 10 |
| Polyamide fiber (3 mm long, 0.9 Dtex) | 5 |
| Isododecane | q.s. 100 |

Example 13

Eye Shadow

In one aspect, the present invention provides a composition in the form of an eye shadow prepared, for example, in a manner similar to that of EXAMPLE 10, according to the weight percentage values indicated in Table 13. In one aspect, the increased presence of fibers, optionally combined with fillers, improves the transfer-resistance property compared with a composition not containing any fibers. In a further aspect, the combination of spherical fillers with fibers improves the disintegration of the product and thus makes it easier for the make-up to be deposited on the skin.

TABLE 13

| Component | Weight percent |
| --- | --- |
| ETPEA | 11 |
| Parleam | 10 |
| Blue 1 Al lake | 0.1 |
| Polyamide fiber (3 mm long, 0.9 Dtex) | 0 to 5 |
| Nylon-12 powder (spherical filler) | 0 to 10 |
| Isododecane | q.s. 100 |

Example 14

Nail Polish

In one aspect, the present invention provides a composition in the form of a nail polish, prepared by reacting together the ingredients indicated in Table 14. In a preferred aspect, the nail polish product is provided in the form of a structured solid composition, such as a stick.

TABLE 14

| Component | Weight percent |
| --- | --- |
| ETPEA | 20 |
| Nitrocellulose | 8 |
| Pigments | 1 |
| Butyl acetate | q.s. 100 |

Example 15

Transfer Resistant Mascara

In one aspect, the present invention provides a composition in the form of a transfer resistant mascara, prepared by reacting together the ingredients indicated in Table 15, as follows. Phases A, B, and C are each prepared separately by mixing together the ingredients of each phase. The three phases are then combined and in a preferred aspect the mascara composition has transfer resistant properties upon application to eyelashes.

TABLE 15

| Phase | Component | Weight percent |
|---|---|---|
| A | Isododecane | 41.97 |
|  | Alkyl silicone resin with alkyl groups (MK Resin) | 7.00 |
|  | Isododecane gel (VERSAGEL ™ MD 870) | 16.50 |
|  | Quaternium 18 Hectorite | 4.00 |
|  | Black iron oxide | 5.00 |
| B | Propylene carbonate | 1.32 |
| C | Paraffin | 3.00 |
|  | Carnauba wax | 5.20 |
|  | Beeswax | 7.00 |
|  | Synthetic beeswax | 4.00 |
|  | ETPEA | 5.00 |
|  | Phenoxyethanol | 0.01 |

Example 16

Transfer Resistant Mascara

In one aspect, the present invention provides a composition in the form of a transfer resistant mascara, prepared by reacting together the ingredients indicated in Table 16. In one aspect, Phase A is mixed with a homogenizer for 20 minutes at ambient temperature and then heated to about 65° C. for about 15 minutes. In a separate vessel, the components of phase C are combined with propeller mixing and heated to about 85-90° C., before adding phase C to phase A. After homogenizing the mixture for about 5 minutes while maintaining the heat at about 80-85° C., phase B can then be added to the mixture. The mixture can then be further homogenized for about 30 minutes at about 80-85° C. before being cooled to about 30-35° C. using sweep mixing. Preferably, the resulting mascara composition has transfer resistant properties upon application to eyelashes.

TABLE 16

| Phase | Component | Weight percent |
|---|---|---|
| A | Isododecane | 40.4 |
|  | Trimethylsiloxysilicate | 7.0 |
|  | Isododecane with | 14.0 |
|  | a) Styrene-ethylene/butylene-styrene triblock copolymer, and | 1.2 |
|  | b) Styrene-ethylene/propylene radial copolymer | 1.2 |
|  | Distearyldiammonium hectorite | 5.5 |
|  | Iron oxides | 5.0 |
| B | Propylene carbonate | 1.8 |
| C | Allyl stearate/VA copolymer | 5.0 |
|  | Waxes | 16.8 |
|  | Preservatives | 0.01 |
|  | ETPEA | 5.00 |

Example 17

Anhydrous Compact Foundation

In one aspect, the present invention provides a composition in the form of an anhydrous compact foundation prepared, for example, in the following manner. ETPEA is solubilized at about 100° C., in a mixture of melted oils and wax, followed by addition of pigments and fillers. The mixture can then be further mixed using, for example, a deflocculating turbomixer (Raynerie). Preferably the resulting composition has good stability (as indicated by, for example, the absence of exudation at ambient temperature, 45° C., and 47° C., both after one month and after two months. Percents (by weight) of the components of the composition reaction mixture are indicated in Table 17. This composition illustrates, e.g., the use of a solid substance in a composition of the present invention.

TABLE 17

| Component | Weight percent |
|---|---|
| Octyldodecanol | 4.4 |
| PTFE | 4.0 |
| Polymethyl methacrylate | 4.0 |
| ETPEA | 7.5 |
| Polyethylene wax MW 500 (weight average molecular weight) | 5.7 |
| Titanium dioxide treated with dimethicone | 5.0 |
| Kaolin | 3.0 |
| Talc | 8.3 |
| Methylparaben | 0.2 |
| Titanium dioxide anatase form | 10.6 |
| Iron oxides | 3.4 |
| Isononyl isononanoate | 15.0 |
| Isostearyl neopentanoate | q.s. 100.0 |

Example 18

Lipstick

In one aspect, the present invention provides a composition in the form of a lipstick prepared, for example, in the following manner. ETPEA is solubilized at about 100° C., in a mixture of melted oils and wax, followed by addition of pigments and fillers. The mixture can then be further mixed using, for example, a deflocculating turbomixer (Raynerie), before being encased in lipstick molds. Preferably the resulting composition has good stability (as indicated by, for example, the absence of exudation at ambient temperature, 45° C., and 47° C., both after one month and after two months. Percents (by weight) of the components of the composition reaction mixture are indicated in Table 18. This composition illustrates, e.g., the use of a solid substance in a composition of the present invention.

TABLE 18

| Component | Weight percent |
|---|---|
| Rosin/Colophonium | 0.6 |
| Barium sulfate | 0.6 |
| Titanium dioxide | 1.2 |
| Red 7 Lake | 1.8 |
| Nylon-12 | 4.0 |
| Iron oxides | 4.0 |
| Polyglyceryl-2 diisostearate | 5.9 |
| Polyethylene wax | 12.0 |
| Diisostearyl malate | 12.0 |
| ETPEA | 15.0 |
| Isononyl isononanoate | q.s. 100.0 |

Example 19

Lipstick

In one aspect, the present invention provides a composition in the form of a lipstick, prepared by reacting together the ingredients indicated in Table 19. In one aspect, the lipstick composition is prepared as follows. First, silica gel (phase B) is prepared by charging a reaction vessel with hydrogenated polyisobutene and octyldodecanol, then adding silica gel portionwise to the mixture, with stirring, in a Rayneri stirrer at about 60° C. In a separate reaction vessel, ground pigmentary material (phase C) can be prepared by first charging the reaction vessel with lanolin, hydrogenated poly isobutene, and octyldodecanol, heating the mixture to about 60° C., mixing pigment into the mixture, then grinding the mixture (for example, about three times in a three-roll mill). Phases B and C can then be combined, heated to about 100° C., and homogenized with stirring.

ETPEA and the oils of phase A can then be introduced into a separate heating vessel. The mixture of phase A can then be placed under magnetic stirring and then heated in a first stage to about 100° C. (or at such temperature warm enough to liquefy the ETPEA). The mixture containing phases B and C can then be introduced to the heating vessel. The resulting product can then be placed in a heated mold (about 45° C.) with stirring and, once setting begins, can then be placed in a freezer (about −21° C.) for about 15 minutes.

The hardness of the lipstick may be measured using the "cheese wire" test described herein. The fragility of the composition may be determined by a method such as wherein the stick is submitted to several back-and-forth movements on a support for about 3 minutes at a speed of about 60 back-and-forth movements per minute, at about 20° C., with the index of fragility defined as that percentage of sticks that break upon undergoing the test conditions. This composition illustrates, e.g., the use of a solid substance in a composition of the present invention.

TABLE 19

| Phase | Component | Weight percent |
| --- | --- | --- |
| A | ETPEA | 16.00 |
|   | Carnauba wax | 13.00 |
|   | Isononyl isononanoate | 13.00 |
|   | Diisostearylmalate | 9.00 |
| B | Hydrophobic silica | 3.00 |
|   | Hydrogenated polyisobutene | 10.36 |
|   | Octyldodecanol | 3.52 |
| C | Pigments | 12.00 |
|   | Liquid lanolin | 14.00 |
|   | Hydrogenated poly isobutene | 4.64 |
|   | Octyldodecanol | 1.48 |

Example 20

Lipstick

In one aspect, the present invention provides a composition in the form of a lipstick, prepared by reacting together the ingredients indicated in Table 20. In one aspect, the lipstick composition is prepared as follows. First, silica gel (phase B) is prepared by charging a reaction vessel with hydrogenated polybutene and isononyl isononanoate, then adding silica gel portionwise to the mixture, with stirring, in a Rayneri stirrer at about 60° C. In a separate reaction vessel, ground pigmentary material (phase C) can be prepared by first charging the reaction vessel with hydrogenated polybutene, heating the mixture to about 60° C., mixing pigment into the mixture, then grinding the mixture (for example, about three times in a three-roll mill). In one aspect, phases B and C can then be combined, heated to about 100° C., and homogenized with stirring.

ETPEA and the oils of phase A can then be introduced into a separate heating vessel. The mixture of phase A can then be placed under magnetic stirring and then heated in a first stage to about 100° C. (or at such temperature warm enough to liquefy the ETPEA). The mixture containing phases B and C can then be introduced to the heating vessel. In one aspect, the whole mixture can then be mixed using, for example, a deflocculating turbomixer (Raynerie) with stirring for about 90 minutes. The resulting product can then be placed in a mold (optionally heated to about 45° C.) with stirring and, once setting begins, can optionally be placed in a freezer (about −21° C.) for about 15 minutes.

In one aspect the sticks of lipstick have a diameter of about 8-13 mm. The hardness of the stick may be measured using the "cheese wire" test described herein. Preferably the lipsticks of the present invention have good staying power, and are glossy and non-greasy. Also preferably the lipsticks of the present invention are stable and do not exude at ambient temperature or at about 47° C., for about 2 months. These sticks illustrate, e.g., the use of at least one inert filler in a composition of the present invention.

TABLE 20

| Phase | Component | Weight percent |
| --- | --- | --- |
| A | ETPEA | 18 |
|   | Diisononyl isononanoate | 5 |
|   | Diisostearylmalate | 17 |
|   | Hydrogenated polybutene (Parleam) | 4 |
| B | Hydrophobic silica (Aerosil R972) | 3 |
|   | Hydrogenated polybutene | 25 |
|   | Isononyl isononanoate | 12 |
| C | Pigments | 7 |
|   | Hydrogenated polybutene | 9 |

Examples 21-23

Cast Foundations

In one aspect, the present invention provides a composition in the form of a cast foundation, prepared by reacting together the ingredients indicated in Table 21. In one aspect, the cast foundation composition is prepared as follows. A heating vessel is charged with ETPEA and isononyl isononanoate, the mixture is heated to 110° C., and stirred with a Rayneri mixer for about 10 minutes, until the ETPEA has fully dissolved. This mixture can be designated "Phase A."

In parallel, a pigmentary phase can be prepared by incorporating pigments (for example, iron oxide+titanium oxide) into isododecane, followed by milling using a three-roll mill. This pigmentary phase ("Phase B") can then be introduced into phase A and the mixture can be stirred until completely homogeneous, in one aspect for about 30 minutes at about 110° C. The temperature of the mixture can then be lowered to about 95° C., before adding isododecane ("Phase D") to the mixture. After stirring the resulting mixture for about 15 minutes, the filler ("Phase C") can be incorporated with stirring for about 20 minutes more. The final mixture can then be cast in foundation molds (in one aspect preheated to about 45° C.), and the mixture can be left to cool to ambient temperature. Preferably, the composition exhibits good stability (i.e., no phase separation) at about 4° C., ambient temperature, and about 45° C., over a length of time spanning about one month, and more preferably about two months. Also preferably, the composition is easy to spread and has a pleasant, non-greasy, light and fondant feel on the fingers. The composition also preferably provides a homogeneous, smooth, natural, and light make-up effect. These sticks illustrate, e.g., the use of at least one inert filler in a composition of the present invention.

TABLE 21

| Phase | Component | Weight percent | | |
|---|---|---|---|---|
| | | Ex. 21 | Ex. 22 | Ex. 23 |
| A | ETPEA | 11 | 11 | 11 |
| | Isononyl isononanoate | 10 | 10 | 10 |
| B | Coated yellow iron oxide* | 2.2 | 2.2 | 2.2 |
| | Coated red iron oxide* | 0.5 | 0.5 | 0.5 |
| | Coated black iron oxide* | 0.3 | 0.3 | 0.3 |
| | Titanium oxide* | 7.0 | 7.0 | 7.0 |
| C | Silica beads (Tospearl 145A) | 10 | — | — |
| | Nylon particles | — | 10 | — |
| | PMMA particles (10 to 12 µm, Wackherr COVABEAD ® LH-85) | — | — | 10 |
| D | Isododecane | q.s. 100.0 | q.s. 100.0 | q.s. 100.0 |

*The coating is aluminum stearoylglutamate.

Example 24

Cast Foundation

In one aspect, the present invention provides a composition in the form of a cast foundation, prepared by reacting together the ingredients indicated in Table 22 in a manner similar to that described in EXAMPLES 21-23. In one aspect, the cast foundation composition has the same cosmetic properties as those of EXAMPLES 21-23. These sticks illustrate, e.g., the use of at least one inert filler in a composition of the present invention.

TABLE 22

| Component | Weight percent |
|---|---|
| Octyldodecanol | 4.4 |
| Polytetrafluoroethylene wax (particle size 8 µm, MW: 75,000*) | 4.0 |
| Hollow polymethyl methacrylate microspheres (particle size: 10 to 12 µm) | 4.0 |
| ETPEA | 7.4 |
| Polyethylene wax MW: 500* | 3.7 |
| Nano-titanium oxide (particle size 2 nm) coated with PDMS | 5.0 |
| Kaolinite (hydrated aluminum silicate) | 3.0 |
| Talc (particle size 2 µm) | 8.3 |
| Methyl p-hydroxybenzoate | 0.2 |
| Titanium oxide (untreated anatase) | 10.6 |
| Black iron oxide | 1.0 |
| Yellow iron oxide | 2.1 |
| Isononyl isononanoate | 15.0 |
| Isostearyl neopentanoate | q.s. 100.0 |

*MW: number-average molecular mass.

Example 25

Mascara

In one aspect, the present invention provides a composition in the form of a mascara, prepared by mixing the ingredients as indicated in Table 23. In a preferred aspect, the mascara obtained is easy to apply, adheres well to the eyelashes during and after application, and allows the eyelashes to be made up quickly.

TABLE 23

| Component | Weight percent |
|---|---|
| ETPEA | 1.0 |
| Carnauba wax | 2.6 |
| Beeswax | 3.3 |
| Paraffin wax | 10.4 |
| Hydrogenated jojoba oil | 0.2 |
| Hydrogenated palm oil | 0.2 |
| 2-Amino-2-methyl-1,3-propanediol | 0.8 |
| Triethanolamine | 2.4 |
| Stearic acid | 6.6 |
| Hydroxyethylcellulose | 0.8 |
| Gum arabic | 0.6 |
| Ethyl acrylate/methyl methacrylate copolymer (80/20) as an aqueous dispersion containing 50% AM (Daitosol 5000 AD from Saito) | 5.0 AM |
| Black iron oxide | 7.0 |
| Preserving agents | q.s. |
| Water | q.s. 100.0 |

Example 26

Mascara

In one aspect, the present invention provides a composition in the form of a mascara, prepared by mixing the ingredients as indicated in Table 24. In a preferred aspect, the mascara obtained adheres well to the eyelashes during and after application, gives the eyelashes instantaneous loading, and allows the eyelashes to be made up quickly.

TABLE 24

| Component | Weight percent |
|---|---|
| ETPEA | 1.0 |
| Carnauba wax | 4.6 |
| Rice bran wax | 2.1 |
| Beeswax | 8.2 |
| Paraffin | 2.2 |
| Talc | 1.0 |
| Bentonite | 5.0 |
| Vinyl acetate/allyl stearate copolymer (65/35) (MEXOMER ™ PQ from Chimex) | 6.5 |
| Polyvinyl laurate (MEXOMER ™ PP from Chimex) | 0.7 |
| Sulfopolyester (AQ 55S from Eastman Chemical) | 0.12 |
| Isododecane | 53.9 |
| Propylene carbonate | 1.6 |
| Pigments | 4.9 |
| Preserving agents | q.s. |
| Water | q.s. 100.0 |

Examples 27-39

Clear Anhydrous Sunscreen Stick (Optionally with an Oil-Soluble Cationic Polymer)

In one aspect, the present invention provides a composition in the form of a clear anhydrous sunscreen stick, prepared by reacting together the ingredients indicated in Table 25. In one aspect, the sunscreen stick composition is prepared as follows. The ingredients of phase A are added to a main vessel and heated to about 110° C.-115° C. while mixing with the aid of an impeller mixer. Then phase B is added to phase A with continued mixing. ETPEA from phase B is allowed to dissolve, and the mixture is then cooled to about 80° C.-82° C. Phases C, D, and E are then added to the mixture while maintaining the temperature at about 80° C.-82° C. with slow impeller mixing. Compositions are mixed until homogenous (in one aspect, about one minute), then are used to fill a suitable container or mold.

In certain aspects, the resulting compositions acquire a fine to moderate uniform oil coat covering the composition surface. Preferably, the resulting compositions are firm at ambient temperature, while the overall structure and stick characteristics remain unchanged when the temperature is elevated to about 45° C.

The compositions of these examples illustrate, e.g., a personal care product comprising ETPEA as a structuring polymer, and at least two components selected from (a) at least one oil-soluble ester comprising at least one free hydroxy group; (b) at least one oil-soluble cationic surfactant; and (c) at least one oil-soluble polymer chosen from alkyl celluloses and alkylated guar gums. The compositions may be, e.g., in the form of a fluid anhydrous gel, a rigid anhydrous gel, a fluid simple emulsion, a rigid simple emulsion, a fluid multiple emulsion, and a rigid multiple emulsion. The composition may contain at least one oil, such as a polar oil or an apolar oil. The composition may contain at least one non-volatile oil. The composition may contain at least one salt of a fatty amine. Examples of oil-soluble esters comprising at least one free hydroxy group include propylene glycol ricinoleate, isopropyl hydroxystearate, triisocetyl citrate, diisostearyl malate, octyl hydroxystearate, triisoarachidyl citrate, cetyl lactate, dioctyl malate, octyldodecyl hydroxystearate, di-isostearyl malate, and di-isostearyl lactate. The composition may include a fatty alcohol, e.g., a C8-C26 fatty alcohol.

Examples 40-41

Lipsticks with an Oil-Soluble Cationic Polymer

In one aspect, the present invention provides a composition in the form of a lipstick with an oil-soluble cationic polymer and/or an oil-soluble ester, prepared, for example, by mixing the ingredients as indicated in Table 26. In one aspect, the composition is mixed until homogeneous, then poured into a suitable container or mold. Preferably the compositions have good stability and no exudation, even at elevated temperatures such as about 47° C.

TABLE 26

| | Weight percent | |
|---|---|---|
| Component | Ex. 40 | Ex. 41 |
| Hydroxyhydrocinnamate | 0.05 | 0.05 |
| Rosin/Colophonium tetradibutyl pentaerythrityl | 0.6 | 0.6 |
| Barium sulfate | 0.6 | 0.6 |
| Titanium dioxide | 1.2 | 1.2 |
| Red 7 Lake | 1.8 | 1.8 |
| Nylon-12 | 3.0 | 4.0 |
| Iron oxides | 4.0 | 4.0 |
| Polyethylene | 3.0 | 12.0 |
| ETPEA | 15.0 | 15.0 |
| Polyglycerol-2 diisostearate | 5.9 | 5.9 |
| Octyldodecanol | 10.0 | — |
| Isononyl isononanoate | 5.9 | q.s. 100.0 |
| Diisostearyl malate | q.s. 100.0 | 12.0 |

TABLE 25

| | | Weight percent | | | | | | | | | | | | |
|---|---|---|---|---|---|---|---|---|---|---|---|---|---|---|
| Phase | Component | Ex. 27 | Ex 28 | Ex. 29 | Ex. 30 | Ex. 31 | Ex. 32 | Ex. 33 | Ex. 34 | Ex. 35 | Ex. 36 | Ex. 37 | Ex. 38 | Ex. 39 |
| A | Diisostearyl malate | 11.1 | 11.1 | 10.0 | 10.0 | 10.0 | 10.0 | 10.0 | 10.0 | 10.0 | 10.0 | 10.0 | 10.0 | 10.0 |
| | Dioctyl malate | 11.1 | 11.1 | 20.0 | 20.0 | 20.0 | 20.0 | 20.0 | 20.0 | 20.0 | 20.0 | 20.0 | 20.0 | 20.0 |
| | Castor oil | 36.7 | 36.6 | 30.6 | 29.9 | 29.0 | 28.9 | 27.9 | 29.4 | 26.15 | 24.15 | 22.9 | 23.9 | 23.15 |
| | Propylene glycol ricinoleate | 11.7 | 11.7 | 10.5 | 10.5 | 10.5 | 10.5 | 10.5 | 10.5 | 10.5 | 10.5 | 10.5 | 10.5 | 10.5 |
| | Lauryl methyl glyceth-10 hydroxypropyl diammonium chloride | — | — | — | — | — | 1.0 | 2.0 | 0.5 | — | — | — | — | — |
| | N-Hance-AG-50 ($C_1$–$C_5$ alkyl galactomannan) | — | — | — | — | — | — | — | — | — | — | 2.0 | — | — |
| | N-Hance-AG-200 ($C_1$–$C_5$ alkyl galactomannan) | — | — | — | — | — | — | — | — | — | — | — | 3.0 | — |
| | Ethocell 100 (Ethyl cellulose) | — | — | — | — | — | — | — | — | — | — | — | 2.0 | — |
| | Ethocell 7 (Ethyl cellulose) | — | — | — | — | — | — | — | — | — | — | — | — | 3.0 |
| B | ETPEA | 17.8 | 17.8 | 16.0 | 16.0 | 16.0 | 16.0 | 16.0 | 16.0 | 16.0 | 16.0 | 16.0 | 16.0 | 16.0 |
| C | Cetyl alcohol | — | — | 2.0 | 3.0 | 4.0 | 3.0 | 3.0 | 3.0 | 4.0 | 4.0 | 4.0 | 4.0 | 4.0 |
| | Propyl parraben | — | — | — | — | — | 0.1 | 0.1 | 0.1 | 0.1 | 0.1 | 0.1 | 0.1 | 0.1 |
| D | Benzophenone-3 | 3.3 | 3.3 | 3.0 | 3.0 | 3.0 | 3.0 | 3.0 | 3.0 | — | — | — | — | — |
| | Octyl methoxycinnamate | 8.3 | 8.3 | 7.5 | 7.5 | 7.5 | 7.5 | 7.5 | 7.5 | — | — | — | — | — |
| | Butyl methoxydibenzoyl methane | — | — | — | — | — | — | — | — | 3.0 | 3.0 | 3.0 | 3.0 | 3.0 |
| | Octocrylene | — | — | — | — | — | — | — | — | 10.0 | 10.0 | 10.0 | 10.0 | 10.0 |
| E | Others* | — | 0.06 | 0.4 | 0.1 | — | — | — | — | 0.25 | 0.25 | 0.5 | 0.5 | 0.25 |

*Others: preservatives, masking agents, colorants, vitamins, oil-soluble actives, antioxidants, dermatological actives, flavoring oils, etc.

Examples 42-44

Anhydrous Gel Lip Compositions

In one aspect, the present invention provides a composition in the form of an anhydrous gel lip composition prepared, for example, by mixing the ingredients as indicated in Table 27. In one aspect, the composition is mixed until homogeneous, then poured into a suitable container or mold. Preferably the compositions have good stability at ambient temperature, as well as good sunscreen properties.

TABLE 27

| Component | Weight percent | | |
|---|---|---|---|
| | Ex. 42 | Ex. 43 | Ex. 44 |
| ETPEA | 25.0 | 25.0 | 25.0 |
| Hydrogenated polyisobutene | 62.0 | 58.0 | 55.5 |
| Octyldodecanol | 10.0 | 10.0 | 10.0 |
| Hydrogenated polyisobutene (45%) Polyhydroxystearic acid (5%) Yellow 5 Lake (50%) | 0.01 | 0.01 | 0.01 |
| Ethylhexyl methoxycinnamate | 1.0 | 5.0 | 7.5 |
| Fragrance | 2.0 | 2.0 | 2.0 |

Example 45

Lipstick

In one aspect, the present invention provides a composition in the form of a lipstick, prepared by reacting together the ingredients indicated in Table 28. In one aspect, the lipstick composition can be prepared as follows. First, silica (phase B) is charged to a heating vessel and then dispersed using a Rayneri stirrer in the mixtures of oils of phase B, heated to about 60° C. When the resulting gel is homogeneous, Bentone can then be added. The mixture can then be stirred until a homogeneous preparation is obtained, corresponding to phase B. Phase C can be prepared by grinding pigment in hydrogenated polybutene using, for example, a three-roll mill.

ETPEA (phase A) can then be added to phase B and the mixture can be heated to about 100° C. When the resulting mixture becomes homogeneous, the ground material C can then be added, and the resulting mixture can then be heated for about 90 minutes with stirring. The preparation can then be discharged into molds for lipsticks in stick form.

In one aspect, the produced sticks of lipstick have a diameter of about 8.1 mm. In preferred aspects, the sticks of lipstick do not exude at ambient temperature for several months, and at about 37° C. or 47° C. for about one month; and the sticks deposit a glossy film with good staying power and no migration. The composition of this example illustrates the inclusion of a gelling agent (in this case, Bentone 38V, a modified clay) in a personal care composition.

TABLE 28

| Phase | Component | Weight percent |
|---|---|---|
| A | ETPEA | 18.0 |
| B | Bentone 38 V | 3.0 |
| | Diisostearyl malate | 16.3 |
| | Isononyl isononanoate | 2.3 |
| | Hydrogenated polybutene | 36.4 |
| | Hydrophobic silica (Aerosil R972) | 3.0 |

TABLE 28-continued

| Phase | Component | Weight percent |
|---|---|---|
| C | Pigments | 7.0 |
| | Isononyl isononanoate | 14.0 |

Example 46

Lipstick

In one aspect, the present invention provides a composition in the form of a lipstick, prepared by reacting together the ingredients indicated in Table 29. In one aspect, the lipstick composition can be prepared as follows. First, ETPEA, GP-1, and the oils of phase A can be introduced into a heating vessel. The mixture can then be placed under magnetic stirring and heated in a first stage to about 100° C. (or at such temperature warm enough to liquefy the ETPEA), then to a temperature required to obtain a transparent homogeneous liquid. The mixture can then be heated to a temperature about 10° C. above that which is required to obtain a transparent homogeneous liquid; before being combined with a mixture comprising phases B and C (prepared according to EXAMPLE 20). The whole mixture can then be stirred for about 1 hour before being cast in a mold (optionally heated to about 45° C. Once the composition begins to set, the charged mold can then be optionally placed in a freezer (about −21° C.) for about 15 minutes. In one aspect, the sticks of lipstick composition have a diameter of about 12.7 mm The hardness of the composition may be measured (for example) with a "cheese wire." Preferably the sticks of the lipstick composition of the present invention do not break during measurement of dynamic fragility.

The composition of this Example illustrates a composition of the present invention comprising an organogelator. Organogelators as a group are defined, e.g., in PCT International Publication No. WO 02/055030, the disclosure of which is incorporated herein by reference.

TABLE 29

| Phase | Component | Weight percent |
|---|---|---|
| A | ETPEA | 18.0 |
| | GP-1 (from Ajinomoto) | 5.0 |
| | Isononyl isononanoate | 3.3 |
| | Diisostearyl malate | 15.3 |
| | Hydrogenated polybutene (Parleam) | 2.3 |
| B | Hydrophobic silica | 3.0 |
| | Hydrogenated polybutene (Parleam) | 25.0 |
| | Isononyl isononanoate | 12.0 |
| C | Pigments | 7.0 |
| | Hydrogenated polybutene (Parleam) | 9.0 |

Example 47

Lipstick

In one aspect, the present invention provides a composition in the form of a lipstick, prepared by reacting together the ingredients indicated in Table 30. In one aspect, the lipstick composition can be prepared as follows. First, ETPEA, trans-diaminocyclohexane derivative, and the oils of phase A can be introduced into a heating vessel. The mixture can then be placed under magnetic stirring and heated in a first stage to about 100° C. (or at such temperature warm enough to liquefy the ETPEA), then to a temperature required to obtain a transparent homogeneous liquid. The mixture can then be heated to a temperature about 10° C. above that which is required to obtain a transparent homogeneous liquid; before being combined with a mixture comprising phases B and C (prepared according to EXAMPLE 20). The whole mixture can then be stirred for about 1 hour before being cast in a mold (optionally heated to about 45° C. Once the composition begins to set, the charged mold can then be optionally placed in a freezer (about −21° C.) for about 15 minutes. In one aspect, the sticks of lipstick composition have a diameter of about 12.7 mm and a hardness that can be measured (for example) with a "cheese wire." In preferred aspects, the sticks of the lipstick composition of the present invention do not break during measurement of dynamic fragility; the sticks of the lipstick composition do not exude; and the sticks of the lipstick composition deposit a glossy make-up on the lips. The composition of this Example illustrates a composition of the present invention comprising an organogelator. Organogelators as a group are defined, e.g., in PCT International Publication No. WO 02/055030, the disclosure of which is incorporated herein by reference.

TABLE 30

| Phase | Component | Weight percent |
|---|---|---|
| A | ETPEA | 18.0 |
|   | Trans-N,N'=bis(dodecanoyl)-1,2-diaminocyclohexane | 5.0 |
|   | Isononyl isononanoate | 3.3 |
|   | Diisostearyl malate | 15.3 |
|   | Hydrogenated polybutene (Parleam) | 2.3 |
| B | Hydrophobic fumed silica | 3.0 |
|   | Hydrogenated polybutene (Parleam) | 25.0 |
|   | Isononyl isononanoate | 12.0 |
| C | Pigments | 7.0 |
|   | Hydrogenated polybutene (Parleam) | 9.0 |

Examples 48-49

Lipstick

In one aspect, the present invention provides a composition in the form of a lipstick, prepared by reacting together the ingredients indicated in Table 31. In one aspect, the lipstick composition can be prepared as follows. First, phase A can be introduced into a heating vessel, placed under magnetic stirring and heated to a temperature required to obtain a transparent homogeneous liquid. The mixture can then be heated to a temperature about 10° C. above that which is required to obtain a transparent homogeneous liquid, before being combined with pigments ground in a three-roll mill (phase B) followed by phase C. The whole mixture can then be stirred for about 90 minutes before being cast in a mold (optionally heated to about 45° C. Once the composition begins to set, the charged mold can then be optionally placed in a freezer (about −21° C.) to carry out tempering. In one aspect, the sticks of lipstick composition have a diameter of about 12.7 mm and a hardness of about 150 to 204 gf, measured (for example) with a "cheese wire." In preferred aspects, the sticks of the lipstick composition of the present invention do not break during measurement of dynamic fragility; do not exude; and are glossy in appearance; and the deposit on the lips from the sticks of the lipstick composition is comfortable and glossy.

The composition of this Example illustrates a composition of the present invention comprising an organogelator. Organogelators as a group are defined, e.g., in PCT International Publication No. WO 02/055030, the disclosure of which is incorporated herein by reference.

TABLE 31

| | | Weight percent | |
|---|---|---|---|
| Phase | Component | Ex. 48 | Ex. 49 |
| A | ETPEA | 18.00 | 18.00 |
|   | GP-1 (Ajinomoto) | 5.00 | — |
|   | Trans-N,N'=bis(dodecanoyl)-1,2-diaminocyclohexane | — | 5.00 |
|   | Polyethylene wax MW: 500* | 3.00 | 3.00 |
|   | Liquid lanolin | 5.00 | 5.00 |
|   | BHT | 0.07 | 0.07 |
|   | Octyl dodecanol | 8.25 | 8.25 |
|   | Phenyl silicone (20 cSt at 25° C.) | 4.58 | 4.58 |
|   | Hydrogenated polybutene (Parleam) | 22.24 | 22.24 |
| B | POLYTRAP ® (Dow Corning) | 3.00 | 3.00 |
|   | Hydrogenated polybutene (Parleam) | 20.00 | 20.00 |
|   | Pigments | 8.66 | 8.66 |
| C | Fragrance | 0.20 | 0.20 |

*MW: weight-average molecular mass.

Example 50

Scenting Composition

In one aspect, the present invention provides a composition in the form of a lipstick, prepared by reacting together the ingredients indicated in Table 32. In one aspect, the lipstick composition can be prepared as follows. The constituents, except for the perfume extract, can be mixed under hot conditions (e.g., about 80° C.) and the perfume extract is subsequently added. The mixture can then be stirred, and then cast while cooling to ambient temperature. In preferred aspects, the resulting product is a visually perfect transparent stick; and the product is highly scenting, the fragrance persisting for a long time after application to the skin.

TABLE 32

| Component | Weight percent |
|---|---|
| ETPEA | 25 |
| Perfume extract | 4 |
| Perfume oil | 61 |
| Octyldodecanol | 10 |

Example 51

Balm for the Lips Scented with Violet

In one aspect, the present invention provides a composition in the form of a balm for the lips scented with violet, prepared by reacting together the ingredients indicated in Table 33. In one aspect, the lipstick composition can be prepared in a manner similar to that described in EXAMPLE 50. In preferred aspects, the resulting product is transparent; the resulting product is violet in color; and the resulting product pleasantly scents the lips.

TABLE 33

| Component | Weight percent |
|---|---|
| ETPEA | 25 |
| "Violine" fragrance | 4 |
| Parleam oil | 60.998 |
| Octyldodecanol | 10 |
| D&C Violet No. 2 dye | 0.002 |

Example 52

Scenting Stick

In one aspect, the present invention provides a composition in the form of a scenting stick, prepared by reacting together the ingredients indicated in Table 34. In one aspect, the lipstick composition can be prepared in a manner similar to that described in EXAMPLE 50. In a preferred aspect, the resulting product is transparent.

TABLE 34

| Component | Weight percent |
|---|---|
| ETPEA | 25 |
| Fragrance | 2 |
| Octyldodecanol | 73 |

Example 53

Scenting Cast Product

In one aspect, the present invention provides a composition in the form of a scenting cast product, prepared by reacting together the ingredients indicated in Table 35. In one aspect, the lipstick composition can be prepared in a manner similar to that described in EXAMPLE 50.

TABLE 35

| Component | Weight percent |
|---|---|
| ETPEA | 25 |
| Fragrance | 2 |
| Octyldodecanol | 73 |

Example 54

Scenting Cast Product

In one aspect, the present invention provides a composition in the form of a scenting cast product, prepared by reacting together the ingredients indicated in Table 36. In one aspect, the lipstick composition can be prepared in a manner similar to that described in EXAMPLE 50.

TABLE 36

| Component | Weight percent |
|---|---|
| ETPEA | 20 |
| Fragrance | 2 |
| Octyldodecanol | 78 |

Examples 55-56

Foundation

In one aspect, the present invention provides a composition in the form of cosmetic foundation, prepared by reacting together the ingredients indicated in Table 37. In one aspect, the cosmetic foundation composition can be prepared as follows. First, a reaction vessel is charged with phase B, and the reaction mixture can be heated to about 120° C., optionally with agitation, then homogenized, for example, with a deflocculating turbomixer (Raynerie). The reaction can then be further charged with phase A, followed by pigments ground in a three-roll mill (phase C), and the resulting mixture is brought to about 100° C. The reaction vessel can then be further charged with phase D and phase E in a gradual steady manner, with the aid of a homogenizer. The reaction mixture is allowed to react for about 10 minutes before being discharged into product containers.

In various aspects, the resulting product is solid, held easily on a finger, and has a hardness strength of about 35 to 50 g. In another aspect the cosmetic foundation composition is moist and preferably spreads out well, forming a uniform, light deposit on the skin. In a preferred aspect, the resulting cosmetic product is natural and satiny.

TABLE 37

| | | Weight percent | |
|---|---|---|---|
| Phase | Component | Ex. 55 | Ex. 56 |
| A | Sorbitan isostearate (Uniqema ARLACEL ™ 987) | 4.50 | 4.50 |
| | Preservative | 0.20 | 0.20 |
| B | ETPEA | 15.00 | 17.00 |
| | Octyl-2-dodecanol | 3.60 | 3.60 |
| | Hydrogenated isoparaffin (Parleam) | 11.00 | 11.00 |
| C | Titanium dioxide | 4.10 | 4.10 |
| | Hydrogenated isoparaffin (Parleam) | 7.00 | 7.00 |
| | Iron oxide | 1.30 | 1.30 |
| D | Perfume | 0.65 | 0.65 |
| E | Propylene glycol | 3.00 | 3.00 |
| | Magnesium sulfate | 0.70 | 0.70 |
| | Preservative | 0.30 | 0.30 |
| | Water | q.s. 100.00 | q.s. 100.00 |

Example 57

Solid Foundation

In one aspect, the present invention provides a composition in the form of solid cosmetic foundation, prepared by reacting together the ingredients indicated in Table 38. In one aspect, the cosmetic foundation composition can be prepared in a manner similar to that described in EXAMPLES 55-56. In one aspect, the resulting product has a nice solid texture and exhibits properties similar to those of the product composition of EXAMPLES 55-56.

TABLE 38

| Phase | Component | Weight percent |
|---|---|---|
| A | Sorbitan isostearate (Uniqema ARLACEL ™ 987) | 4.50 |
|   | Preservative | 0.20 |
| B | ETPEA | 15.00 |
|   | Octyl-2-dodecanol | 3.60 |
|   | Isododecane | 5.00 |
|   | Hydrogenated isoparaffin (Parleam) | 6.00 |
| C | Titanium dioxide | 4.10 |
|   | Hydrogenated isoparaffin (Parleam) | 7.00 |
|   | Nylon powder | 8.00 |
|   | Iron oxide | 1.30 |
| D | Perfume | 0.65 |
| E | Propylene glycol | 3.00 |
|   | Magnesium sulfate | 0.70 |
|   | Preservative | 0.30 |
|   | Water | q.s. 100.00 |

Example 58

Foundation

In one aspect, the present invention provides a composition in the form of solid cosmetic foundation, prepared by reacting together the ingredients indicated in Table 39. In one aspect, the cosmetic foundation composition can be prepared in a manner similar to that described in EXAMPLES 55-56. In one aspect, the resulting product has a fine solid texture and exhibits properties similar to those of the product composition of EXAMPLES 55-56.

TABLE 39

| Phase | Component | Weight percent |
|---|---|---|
| A | Sorbitan isostearate (Uniqema ARLACEL ™ 987) | 6.00 |
|   | Preservative | 0.20 |
| B | ETPEA | 15.00 |
|   | Octyl-2-dodecanol | 3.60 |
|   | Isododecane | 22.50 |
|   | Cyclohexadimethylsiloxane (8 cSt) (Dow Corning DC246) | 5.00 |
|   | Hydrogenated isoparaffin (Parleam) | 11.00 |
| C | Titanium dioxide | 4.10 |
|   | Hydrogenated isoparaffin (Parleam) | 3.30 |
|   | Nylon powder | 4.00 |
|   | Iron oxide | 10.70 |
| D | Perfume | 0.65 |
| E | Magnesium sulfate | 0.70 |
|   | Preservative | 0.20 |
|   | Water | q.s. 100.00 |

Examples 59-60

Lipstick

In one aspect, the present invention provides a composition in the form of lipstick, prepared by reacting together the ingredients indicated in Table 40. In one aspect, the lipstick composition can be prepared as follows. First, the pigmentary phase (B) is ground with the aid of a three-roll mill, and is then introduced into the oily phase A. This mixture can then be heated to about 100° C., optionally with stirring, until homogeneous. The temperature of the mixture can then be reduced to about 85° C. before adding volatile phase C. The whole reaction mixture can then be allowed to react for about 10 minutes before discharging into lipstick molds. In one aspect, the resulting lipstick composition deposits a glossy and non-transferable film.

TABLE 40

| | | Weight percent | |
|---|---|---|---|
| Phase | Component | Ex. 59 | Ex. 60 |
| A | ETPEA | 18 | 18 |
|   | Castor oil | 7 | 8 |
|   | Hydrogenated isoparaffin | 4 | 5 |
|   | Isononyl isononanoate | 4 | 5 |
|   | Phenyl trimethylsiloxy trisiloxane | 8 | 8 |
|   | Copolymer vinylpyrrolidone/1-eicosene | 2 | 2 |
| B | Pigments | 10 | 10 |
|   | Hydrogenated isoparaffin | 5 | 5 |
|   | liquid lanolin | 5 | 5 |
|   | Poly(12-hydroxystearic) acid | 2 | 2 |
| C | Isododecane | 25 | 27 |
|   | Decamethyl tetrasiloxane | 10 | 5 |

Example 61

Lipstick

In reference to Table 41, the pigmentary phase (B), ground with the aid of a three-roll mill, is introduced into the oily phase A (heated to about 100° C. prior to mixing), and the mixture is allowed to react until completely homogeneous. After reducing the heat of the reaction mixture to about 85° C., the volatile phase C can then be added to the mixture. The resulting reaction mixture is then allowed to react for about 10 minutes before being poured into lipstick molds, affording a stick bi-product. In one aspect the bi-product is a stick with two tips which presents two options: one tip is glossy in color and can deposit a glossy colored film on the lips, while a second tip can deposit on the lips a film with reduced cling and reduced transferability. Preferably, the stick does not exude at ambient temperature for a period lasting at least about 2 months.

In one aspect, the stick product essentially provides 3 different types of lipstick to the user: 1) a single-coat lipstick with reduced transferability, 2) a glossy single-coat lipstick, and 3) a double-coat lipstick containing the properties of lipstick types 1 and 2. In one aspect of the double-coat lipstick, the base coat (i.e., the coat in direct contact with the lips) is the coat with reduced transferability, while the superior coat (i.e., the coat applied over the base coat) is the glossy coat. In another aspect of the double-coat lipstick, the two coats are applied in the order reverse to the foregoing. In other aspects, the resulting makeup is comfortable, non-clinging, glossy, and of high quality.

TABLE 41

| Phase | Component | Weight percent |
|---|---|---|
| A | ETPEA | 18 |
|   | Fluorinated silicone (Shin Etsu X22819) | 5 |
|   | Castor oil | 2 |
|   | Hydrogenated isoparaffin | 4 |
|   | Isononyl isononanoate | 4 |
|   | Phenyl trimethylsiloxytrisiloxane | 8 |
|   | Copolymer vinylpyrrolidone/1-eicosene | 2 |
| B | Pigments (iron oxide) | 10 |
|   | Hydrogenated isoparaffin | 5 |
|   | Liquid lanolin | 5 |
|   | Poly(12-hydroxystearic) acid (Avecia SOLSPERSE ™ 21 000) | 2 |
| C | Isododecane | 25 |
|   | Decamethyltetrasiloxane | 10 |

Example 62

Lipstick

In reference to Table 42, the pigmentary phase (B), ground with the aid of a three-roll mill, is introduced into the oily phase A (heated to about 100° C. prior to mixing), and the mixture is allowed to react until completely homogeneous. After reducing the heat of the reaction mixture to about 85° C., the volatile phase C can then be added to the mixture. The resulting reaction mixture is then allowed to react for about 10 minutes before being poured into lipstick molds, affording a stick bi-product. In one aspect the bi-product is a stick with two tips which presents two options: one tip is glossy in color and can deposit a glossy colored film on the lips, while a second tip can deposit on the lips a film with reduced cling and reduced transferability. Preferably, the stick does not exude at ambient temperature for a period lasting at least about 2 months.

In one aspect, the stick product essentially provides 3 different types of lipstick to the user, either single-coat or double-coat.

TABLE 42

| Phase | Component | Weight percent |
|---|---|---|
| A | ETPEA | 18 |
|   | Castor oil | 8 |
|   | Hydrogenated isoparaffin | 5 |
|   | Isononyl isononanoate | 5 |
|   | Phenyl trimethylsiloxytrisiloxane | 8 |
|   | Copolymer vinylpyrrolidone/1-eicosene | 2 |
| B | Pigments (iron oxide) | 10 |
|   | Hydrogenated isoparaffin | 5 |
|   | Liquid lanolin | 5 |
|   | Poly(12-hydroxystearic) acid (Avecia SOLSPERSE ™ 21 000) | 2 |
| C | Isododecane | 22 |
|   | Nonafluoromethoxybutane | 5 |
|   | Decamethyltetrasiloxane | 5 |

Example 63

Lipstick

Utilizing the components and amounts set forth in Table 43, a cosmetic composition was prepared following the procedure of Examples 61 and 62. In one aspect the resulting stick product is a mono-product, one that deposits a single film that is, in various aspects, glossy, with reduced clinging properties, and with reduced transferability properties. Preferably, the stick does not exude at ambient temperature for a period lasting at least about 2 months.

TABLE 43

| Phase | Component | Weight percent |
|---|---|---|
| A | ETPEA | 18.0 |
|   | Fluorinated silicone (Shin Etsu X22819) | 5.0 |
| B | Pigments (iron oxide) | 10.0 |
|   | Poly(12-hydroxystearic) acid (Avecia SOLSPERSE ™ 21 000) | 1.3 |
| C | Parleam | 13.8 |
|   | Isononyl isononanoate | q.s. 100.0 |

Example 64

Mascara

A mascara composition is prepared by blending the components and amounts set forth in Table 44. In one aspect, the mascara composition of the present invention adheres well to the eyelashes during and after application. In another aspect, the mascara composition of the present invention gives good instantaneous loading of the eyelashes.

TABLE 44

| Component | Weight percent |
|---|---|
| Beeswax | 7.1 |
| Hydrogenated jojoba oil | 7.1 |
| ETPEA | 0.5 |
| Polybutylene | 1.0 |
| Copolymer hydroxyethylcellulose/diallyl dimethyl ammonium chloride (National Starch CELQUAT ™ LOR) | 3.8 |
| Glycerol mono- and distearate (Goldschmidt TEGIN ™ M) | 2.1 |
| PEG-30 glyceryl monostearate (Goldschmidt TAGAT ™ S) | 5.5 |
| Black iron oxide | 7.0 |
| Preservatives | q.s. |
| Water | q.s. 100.0 |

Example 65

Mascara (A) A microdispersion of carnauba wax is prepared having the composition indicated in Table 45:

TABLE 45

| Component | Weight percent |
|---|---|
| Carnauba wax | 27.00 |
| PEG-30 glyceryl monostearate (Goldschmidt TAGAT ™ S) | 6.75 |
| Ethanol | 10.00 |
| Water | q.s. 100.00 |

The wax and surfactant (PEG-30 glyceryl monostearate) are heated to 90° C. while homogenizing the mixture under moderate agitation. One can then add water heated to 90° C. to the mixture, with continued agitation. After cooling the mixture down to ambient temperature, ethanol is added to obtain a microdispersion of wax, the particles of which have an average diameter of about 170 nm in one aspect.

(B) A mascara is prepared having the composition provided in Table 46.

TABLE 46

| Component | Weight percent |
|---|---|
| Wax microdispersion of (A) above | 5.0 |
| Carnauba wax | 1.5 |
| Beeswax | 3.6 |
| Paraffin wax | 11.5 |
| Hydrogenated jojoba oil | 0.2 |
| Hydrogenated palm oil | 0.2 |
| ETPEA | 0.5 |
| 2-Amino-2-methyl-1,3-propanediol | 0.8 |
| Triethanolamine | 2.4 |
| Stearic acid | 6.6 |

TABLE 46-continued

| Component | Weight percent |
| --- | --- |
| Hydroxyethylcellulose | 0.8 |
| Gum arabic | 0.6 |
| Copolymer ethyl acrylate/methyl methacrylate (80/20) as an aqueous dispersion containing 50% AM (Saito DAITOSOL ™ 5000 AD) | 5.0 AM |
| Black iron oxide | 7.0 |
| Preservatives | q.s. |
| Water | q.s. 100.00 |

Example 66

Mascara

A mascara composition is prepared by blending the components and amounts set forth in Table 47.

TABLE 47

| Component | Weight percent |
| --- | --- |
| Carnauba wax | 2.9 |
| Beeswax | 3.6 |
| Paraffin wax | 11.5 |
| Hydrogenated jojoba oil | 0.2 |
| Hydrogenated palm oil | 0.2 |
| ETPEA | 2.0 |
| 2-Amino-2-methyl-1,3-propanediol | 0.8 |
| Triethanolamine | 2.4 |
| Stearic acid | 6.6 |
| Hydroxyethylcellulose | 0.8 |
| Gum arabic | 0.6 |
| Copolymer ethyl acrylate/methyl methacrylate (80/20) as an aqueous dispersion containing 50% AM (Saito DAITOSOL ™ 5000 AD) | 2.5 AM |
| Black iron oxide | 7.0 |
| Preservatives | q.s. |
| Water | q.s. 100.00 |

Example 67

Anhydrous Lipstick with an Opaque Base

With reference to the ingredients in Table 48, a lipstick can be prepared as follows. ETPEA, waxes and oils are charged to a reaction vessel and the mixture is heated until homogeneous. The reaction vessel is further charged with colorant, and the reaction mixture is further homogenized under magnetic agitation for about 1 hour. The reaction composition is then poured into a mold kept at an elevated temperature (e.g., about 45° C.) to form a stick product. Once the stick product begins to take shape, the product is allowed to congeal by resting at about −21° C. for about 15 minutes.

The transmittance at 530 nm (i.e., the $\lambda_{max}$ of coloring) of a sample (about 10 μm thick) of the composition of the lipstick above is measured. In one aspect the lipstick has an opaque appearance and gives a transparent cosmetic deposit conferring a pink fuchsia color to the lips. In one aspect the color deposited is very intense.

TABLE 48

| Component | Weight percent |
| --- | --- |
| Propoxylated beeswax | 14.5 |
| Microcrystalline wax | 3.0 |
| Propoxylated lanolin wax | 2.0 |
| Sesame oil | 10.0 |
| Arara oil | 18.0 |
| Lanolin | 20.0 |
| Acetylated lanolin | 6.0 |
| Phytocos MMB RED ® Complex 33/3 colorant | 0.2 (active colorant matter) |
| ETPEA | q.s. |
| Oleyl erucate | q.s. 100.0 |

Example 68

Anhydrous Lipstick with a Transparent Base

With reference to the ingredients in Table 49, a lipstick can be prepared as follows. ETPEA and oils are charged to a reaction vessel and the mixture is heated until the ETPEA is melted and the reaction mixture becomes transparent and homogeneous. The reaction vessel is further charged with colorant, and the reaction mixture is further homogenized under magnetic agitation for about 1 hour. The reaction composition is then poured into a mold kept at an elevated temperature (e.g., about 45° C.) to form a stick product. Once the stick product begins to take shape, the product is allowed to congeal by resting at about −21° C. for about 15 minutes.

The transmittance at 530 nm (i.e., the $\lambda_{max}$ of coloring) of a sample (about 10 μm thick) of the composition of the lipstick above is measured. In one aspect the resulting lipstick composition is translucent, and when the stick is applied to a substrate, deposits a transparent streak of pink color

TABLE 49

| Component | Weight percent |
| --- | --- |
| ETPEA | 25.0 |
| Octyldodecanol | 10.0 |
| Phytocos MMB RED ® Complex 33/3 colorant | 0.2 (active colorant matter) |
| Parleam oil | q.s. 100.0 |

Example 69

Lipstick

Using the components identified in Table 50, a lipstick composition can be prepared as follows. ETPEA and oil are charged to a reaction vessel and the mixture is heated until the ETPEA is melted and the reaction mixture becomes transparent and homogeneous. The reaction vessel is further charged with colorant, and the reaction mixture is further homogenized under magnetic agitation for about 1 hour. The reaction composition is then poured into a mold kept at an elevated temperature (e.g., about 45° C.) to form a stick product. Once the stick product begins to take shape, the product is allowed to congeal by resting at about −21° C. for about 15 minutes.

The transmittance at 498 nm (i.e., the $\lambda_{max}$ of coloring) of a sample (about 10 μm thick) of the composition of the lipstick above is measured. In one aspect the resulting lipstick composition is translucent, and when the stick is applied to a substrate, deposits a transparent streak of orange color

TABLE 50

| Component | Weight percent |
|---|---|
| ETPEA | 25.0 |
| Octyldodecanol | 10.0 |
| ROCOU ® colorant* | 0.2 (active colorant matter) |
| Parleam oil | q.s. 100.0 |

*ROCOU ® is a solution at 4% of rocou seeds in soybean oil, from Warner-Jenkinson.

Example 70

Mascara

A mascara composition is prepared by blending the components and amounts set forth in Table 51.

TABLE 51

| Component | Weight percent |
|---|---|
| ETPEA | 0.5 |
| Carnauba wax | 2.9 |
| Beeswax | 3.6 |
| Paraffin wax | 11.4 |
| 2-Amino-2-methyl-1,3-propanediol | 0.5 |
| Triethanolamine | 2.4 |
| Stearic acid | 5.8 |
| Non-ionic hydrosoluble polymers | 4.3 |
| Sodium polymethacrylate (Vanderbilt DARVAN ™ 7) | 0.25 AM |
| JR 400 modified hydroxyethylcellulose (Union Carbide) | 0.1 |
| Pigments | 5.4 |
| Preservatives | q.s. |
| Water | q.s. 100.0 |

Example 71

Waterproof Mascara

A mascara composition is prepared by blending the components and amounts set forth in Table 52.

TABLE 52

| Component | Weight percent |
|---|---|
| ETPEA | 0.5 |
| Carnauba wax | 4.7 |
| Beeswax | 4.9 |
| Paraffin wax | 2.3 |
| Sodium deoxyribonucleate | 0.2 |
| Bentonite | 5.3 |
| Propylene carbonate | 1.7 |
| Copolymer vinylpyrrolidone/1-eicosene | 2.0 |
| Sodium polymethacrylate (Vanderbilt DARVAN ™ 7) | 0.25 AM |
| JR 400 modified hydroxyethylcellulose (Union Carbide) | 0.1 |
| Copolymer vinyl acetate/allyl stearate (65/35) (Chimex MEXOMERE ™ PQ) | 2.2 |
| Vinyl polylaurate (Chimex MEXOMERE ™ PP) | 0.7 |
| Rice starch | 1.5 |
| Pigments | 4.2 |

TABLE 52-continued

| Component | Weight percent |
|---|---|
| Water | 8.4 |
| Ethyl alcohol | 2.0 |
| Preservatives | q.s. |
| Isododecane | q.s. 100.00 |

Example 72

Lipstick

With reference to Table 53, ETPEA is dissolved in octyldodecanol and parleam oil, at about 100° C., before adding pigments and fillers. This mixture is then combined with a preheated mixture of the waxes and oils (preheated to about 90° C.). All other ingredients are added, and the entire mixture is mixed with the aid of a deflocculating (Raynerie) turbine, then poured into lipstick molds.

TABLE 53

| Component | Weight percent |
|---|---|
| ETPEA | 22.6 |
| Parleam oil | 32.7 |
| Octyldodecanol | 11.3 |
| Poly(12-hydroxystearic) acid | 2.5 |
| Pigments | 10.9 |
| Lanolin (pasty) | 6.3 |
| Waxes | 3.8 |
| Fillers | 3.8 |
| Phenyl silicone (oil) | 6.3 |

Example 73

Lipstick

With reference to the components and amounts set forth in Table 54, ETPEA is dissolved in polyglyceryl-2 polyhydroxystearate and parleam oil, at about 100° C., before adding pigments. This mixture is mixed with the aid of a deflocculating (Raynerie) turbine, then poured into lipstick molds. The hardness of the product may be measured using a texture analyzer TA-XT2 at 20° C.

TABLE 54

| Component | Weight percent |
|---|---|
| ETPEA | 25 |
| Parleam oil | 56 |
| Polyglyceryl-2 polyhydroxystearate | 10 |
| Pigments (brown iron oxide + titanium oxide) | 9 |

Example 74

Anhydrous Eye Shadow

Following the procedure of Example 73, but using the components of Table 55, an anhydrous eye shadow was prepared.

TABLE 55

| Component | Weight percent |
|---|---|
| ETPEA | 25.00 |
| Parleam oil | 35.10 |
| Glyceryl oleate | 31.25 |
| Pigments | q.s. 100.00 |

Throughout the present specification, where resins or reaction mixtures are described as including or comprising specific components or materials, it is contemplated by the inventors that the resins or reaction mixtures of the present invention also consist essentially of, or consist of, the recited components or materials. Accordingly, throughout the present disclosure any described composition (resin or reaction mixture) of the present invention can consist essentially of, or consist of, the recited components or materials.

All publications and patent applications mentioned in this specification are herein incorporated by reference to the same extent as if each individual publication or patent application was specifically and individually incorporated by reference. This includes the parent application, U.S. application Ser. No. 09/855,737 filed May 14, 2001.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A personal care composition, comprising
i) a resin composition prepared by reacting components comprising dibasic acid, diamine, polyol and monoalcohol, wherein
   (a) at least 50 equivalent percent of the dibasic acid comprises polymerized fatty acid;
   (b) at least 50 equivalent percent of the diamine comprises ethylene diamine;
   (c) 10-60 equivalent percent of the total of the hydroxyl and amine equivalents provided by diamine, polyol and monoalcohol are provided by monoalcohol; and
   (d) no more than 50 equivalent percent of the total of the hydroxyl and amine equivalents provided by diamine, polyol and monoalcohol are provided by polyol; and
ii) a non-aqueous liquid.

2. The composition according to claim 1, wherein the non-aqueous liquid comprises is a low polarity liquid.

3. The composition according to claim 1, wherein the non-aqueous liquid comprises a liquid fatty phase.

4. The composition according to claim 1, further comprising water.

5. The composition according to claim 1, comprising
i) a resin composition prepared by reacting components comprising dibasic acid, diamine, polyol and monoalcohol, wherein
   (a) at least 50 equivalent percent of the dibasic acid comprises polymerized fatty acid;
   (b) at least 50 equivalent percent of the diamine comprises ethylene diamine;
   (c) 10-60 equivalent percent of the total of the hydroxyl and amine equivalents provided by diamine, polyol and monoalcohol are provided by stearyl alcohol; and
   (d) no more than 50 equivalent percent of the total of the hydroxyl and amine equivalents provided by diamme, poiyol and monoalcohol are provided by at least one polyol selected from the group consisting of ethylene glycol, propylene glycol, butylene glycol, neopentyl glycol, glycerol, trimethylolpropane, and pentaerythritol.

6. The composifion according to claim 5, wherein the composition is a lipstick composition comprising
a colorant; and
at least one oil that is selected from the group consisting of a hydrocarbon oil, synthetic oil, mineral oil, animal oil, plant oil, and ester-containing oil.

7. The composition according to claim 5, wherein the composition is a lipstick composition comprising
at least one amphiphilic compound having an HLB value that is less than 16;
a colorant; and
at least one oil that is selected from the group consisting of a hydrocarbon oil, synthetic oil, mineral oil, animal oil, plant oil, and ester-containing oil.

8. The composition according to claim 5, wherein the composition is a lipstick composition comprising
at least one silicone oil;
at least one amphiphilic compound having an HLB value that is less than 16;
a colorant; and
at least one oil that is selected from the group consisting of a hydrocarbon oil, synthetic oil, mineral oil, animal oil, plant oil, and ester-containing oil.

9. The composition according to claim 5, wherein the composition is an antisun or sunscreen composition that is an oil-in-water emulsion comprising
a sunscreen agent;
at least one surfactant; and
water.

10. The composition according to claim 9, wherein the sunscreen agent is at least one member selected from the group consisting of benzophenone-3, octyl methoxycinnamate, and butyl methoxydibenzoyl methane.

11. The composition according to claim 5, wherein the composition is an antisun or sunscreen composition that is an oil-in-water emulsion comprising
at least one oil that is selected from the group consisting of a hydrocarbon oil, synthetic oil, mineral oil, animal oil, plant oil, and ester-containing oil;
a sunscreen agent;
at least one surfactant; and
water.

12. The composition according to claim 11, wherein the sunscreen agent is at least one member selected from the group consisting of benzophenone-3, octyl methoxycinnamate, and butyl methoxydibenzoyl methane.

13. The composition according to claim 5, wherein the composition is an antisun or sunscreen composition that is a cream, a paste, a dispersion, or a water-in-oil emulsion comprising
at least one silicone oil;
a sunscreen agent; and
water.

14. The composition according to claim 5, wherein the composition is an antisun or sunscreen composition that is anhydrous or an anhydrous gel comprising
at least one oil that is selected from the group consisting of a hydrocarbon oil, synthetic oil, mineral oil, animal oil, plant oil, and ester-containing oil; and
a sunscreen agent.

15. The composition according to claim 5, wherein the composition is a mascara that is a dispersion, a paste, or an oil-in-water emulsion comprising
- at least one colorant;
- at least one oil that is selected from the group consisting of a hydrocarbon oil, synthetic oil, mineral oil, animal oil, plant oil, and ester-containing oil; and
- water.

16. The composition according to claim 5, wherein the composition is a mascara that is a dispersion, a paste, or an oil-in-water emulsion comprising
- at least one wax;
- at least one colorant;
- at least one oil that is selected from the group consisting of a hydrocarbon oil, synthetic oil, mineral oil, animal oil, plant oil, and ester-containing oil; and
- water.

17. The composition according to claim 5, wherein the composition is a mascara that is a dispersion, a paste, or an oil-in-water emulsion comprising
- at least one amphiphilic compound having an HLB value that is less than 16;
- at least one colorant;
- at least one oil that is selected from the group consisting of a hydrocarbon oil, synthetic oil, mineral oil, animal oil, plant oil, and ester-containing oil; and
- water.

18. The composition according to claim 5, wherein the composition is a mascara that is a dispersion, a paste, or an oil-in-water emulsion comprising
- at least one amphiphilic compound having an HLB value that is less than 16;
- at least one wax;
- at least one colorant;
- at least one oil that is selected from the group consisting of a hydrocarbon oil, synthetic oil, mineral oil, animal oil, plant oil, and ester-containing oil; and
- water.

19. The composition according to claim 5, wherein the composition is a mascara that is anhydrous, an anhydrous gel, or a paste comprising
- at least one colorant; and
- at least one oil that is selected from the group consisting of a hydrocarbon oil, synthetic oil, mineral oil, animal oil, plant oil, and ester-containing oil.

20. The composition according to claim 5, wherein the composition is a mascara that is anhydrous, an anhydrous gel, or a paste comprising
- at least one wax;
- at least one colorant; and
- at least one oil that is selected from the group consisting of a hydrocarbon oil, synthetic oil, mineral oil, animal oil, plant oil, and ester-containing oil.

21. The composition according to claim 5, wherein the composition is a foundation that is an oil-in-water emulsion comprising
- at least one colorant;
- at least one filler that is in powder form;
- at least one surfactant;
- water; and
- at least one oil that is selected from the group consisting of a hydrocarbon oil, synthetic oil, mineral oil, animal oil, plant oil, and ester-containing oil.

22. The composition according to claim 5, wherein the composition is a foundation that is an oil-in-water emulsion comprising
- at least one silicone oil;
- at least one colorant;
- at least one filler that is in powder form;
- at least one surfactant;
- water; and
- at least one oil that is selected from the group consisting of a hydrocarbon oil, synthetic oil, mineral oil, animal oil, plant oil, and ester-containing oil.

23. The composition according to claim 5, wherein the composition is a foundation that is an water-in-oil emulsion or a dispersion comprising
- at least one colorant;
- at least one filler that is in powder form;
- water; and
- at least one oil that is selected from the group consisting of a hydrocarbon oil, synthetic oil, mineral oil, animal oil, plant oil, and ester-containing oil.

24. The composition according to claim 5, wherein the composition is a foundation that is an water-in-oil emulsion or a dispersion comprising
- at least one silicone oil;
- at least one colorant;
- at least one filler that is in powder form;
- water; and
- at least one oil that is selected from the group consisting of a hydrocarbon oil, synthetic oil, mineral oil, animal oil, plant oil, and ester-containing oil.

25. The composition according to claim 5, wherein the composition is a foundation that is anhydrous, an anhydrous gel, a powder, or a dispersion comprising
- at least one colorant;
- at least one filler that is in powder form; and
- at least one oil that is selected from the group consisting of a hydrocarbon oil, synthetic oil, mineral oil, animal oil, plant oil, and ester-containing oil.

* * * * *